US012570607B2

(12) United States Patent
Wang et al.

(10) Patent No.: US 12,570,607 B2
(45) Date of Patent: Mar. 10, 2026

(54) COMPOUND AS CYCLIN-DEPENDENT KINASE 9 INHIBITOR AND USE THEREOF

(71) Applicant: CSPC Zhongqi Pharmaceutical Technology (Shijiazhuang) Co., Ltd., Shijiazhuang (CN)

(72) Inventors: Zhenyu Wang, Shijiazhuang (CN); Yan Zhang, Shijiazhuang (CN); Yongzhao Mu, Shijiazhuang (CN); Jianqiao Guo, Shijiazhuang (CN); Hui An, Shijiazhuang (CN); Na Gao, Shijiazhuang (CN); Chaozai Zhang, Shijiazhuang (CN); Jia Wang, Shijiazhuang (CN)

(73) Assignee: CSPC Zhongqi Pharmaceutical Technology (Shijiazhuang) Co., Ltd., Shijiazhuang (CN)

( * ) Notice: Subject to any disclaimer, the term of this patent is extended or adjusted under 35 U.S.C. 154(b) by 918 days.

(21) Appl. No.: 17/783,863

(22) PCT Filed: Dec. 9, 2020

(86) PCT No.: PCT/CN2020/134966
§ 371 (c)(1),
(2) Date: Jun. 9, 2022

(87) PCT Pub. No.: WO2021/115335
PCT Pub. Date: Jun. 17, 2021

(65) Prior Publication Data

US 2023/0102081 A1 Mar. 30, 2023

(30) Foreign Application Priority Data

Dec. 9, 2019 (CN) ........................ 201911252575.1

(51) Int. Cl.

| | |
|---|---|
| ***C07D 213/74*** | (2006.01) |
| ***A61P 35/02*** | (2006.01) |
| ***C07D 213/81*** | (2006.01) |
| ***C07D 401/04*** | (2006.01) |
| ***C07D 401/12*** | (2006.01) |
| ***C07D 405/04*** | (2006.01) |
| ***C07D 405/12*** | (2006.01) |
| ***C07D 409/12*** | (2006.01) |
| ***C07D 413/12*** | (2006.01) |
| ***C07D 417/12*** | (2006.01) |
| ***C07D 471/04*** | (2006.01) |

(52) U.S. Cl.
CPC ............ *C07D 213/74* (2013.01); *A61P 35/02* (2018.01); *C07D 213/81* (2013.01); *C07D 401/04* (2013.01); *C07D 401/12* (2013.01); *C07D 405/04* (2013.01); *C07D 405/12* (2013.01); *C07D 409/12* (2013.01); *C07D 413/12* (2013.01); *C07D 417/12* (2013.01); *C07D 471/04* (2013.01)

(58) Field of Classification Search
CPC .. C07D 213/74; C07D 213/81; C07D 401/04; C07D 401/12; C07D 405/04; C07D 405/12; C07D 409/12; C07D 413/12; C07D 417/12; C07D 471/04; A61P 35/02
See application file for complete search history.

(56) References Cited

U.S. PATENT DOCUMENTS

| | | | |
|---|---|---|---|
| 9,067,888 | B2 | 6/2015 | Zeitmann et al. |
| 9,650,358 | B2 | 5/2017 | Mastracchio et al. |
| 9,845,331 | B2 | 12/2017 | Barlaam et al. |
| 2011/0130380 | A1 | 6/2011 | Barsanti et al. |
| 2012/0157433 | A1 | 6/2012 | Pfister et al. |

(Continued)

FOREIGN PATENT DOCUMENTS

| | | | |
|---|---|---|---|
| CA | 2901334 A1 | 10/2014 | |
| CN | 102471310 A | 5/2012 | |

(Continued)

OTHER PUBLICATIONS

Anshabo, Frontiers in Oncology, vol. 11, May 10, 2021 (Year: 2021).*

(Continued)

*Primary Examiner* — Andrew D Kosar
*Assistant Examiner* — Phillip Matthew Rzeczycki
(74) *Attorney, Agent, or Firm* — Buchanan Ingersoll & Rooney PC

(57) ABSTRACT

Disclosed is a compound as shown in formula (I) or a pharmaceutically acceptable salt, a stereoisomer, an isotope derivative or a prodrug thereof. The compound has an excellent activity as a cyclin-dependent kinase 9 (CDK9) inhibitor for treating hyperproliferative diseases. The experimental research on in vitro inhibition of cell proliferation and in vivo suppression of tumors shows that such compounds have a relatively strong inhibitory effect on MV4;11 cells and in vivo tumor models, and have a good selectivity and a low toxicity and few side effects, thereby possessing a good clinical value as novel anti-tumor drugs.

(I)

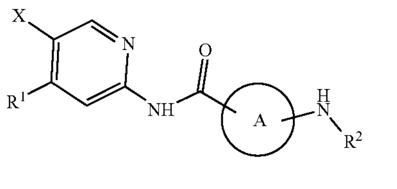

8 Claims, No Drawings

(56) References Cited

U.S. PATENT DOCUMENTS

| | | | | |
|---|---|---|---|---|
| 2012/0165306 | A1 | 6/2012 | Barsanti et al. | |
| 2016/0376287 | A1 * | 12/2016 | Barlaam .............. | C07D 487/04 514/214.02 |
| 2022/0324830 | A1 | 10/2022 | Lu et al. | |

FOREIGN PATENT DOCUMENTS

| | | | | |
|---|---|---|---|---|
| CN | 102482265 | A | 5/2012 | |
| CN | 102498107 | A | 6/2012 | |
| CN | 102834380 | A | 12/2012 | |
| CN | 107873028 | B | 2/2021 | |
| CN | 114786673 | A | 7/2022 | |
| JP | 2018522869 | A | 8/2018 | |
| WO | 2009047359 | A1 | 4/2009 | |
| WO | 2011026917 | A1 | 3/2011 | |
| WO | WO-2011026904 | A1 * | 3/2011 | .............. A61P 35/00 |
| WO | WO-2011026911 | A1 * | 3/2011 | ........... C07D 401/04 |
| WO | 2011110612 | A1 | 9/2011 | |
| WO | 2011116951 | A1 | 9/2011 | |
| WO | 2014076091 | A1 | 5/2014 | |
| WO | 2014160017 | A1 | 10/2014 | |
| WO | 2017001354 | A1 | 1/2017 | |
| WO | 2021050824 | A1 | 3/2021 | |

OTHER PUBLICATIONS

Hernandes Current Drug Targets, Mar. 2010, 11(3): 303-314 (Year: 2010).*

Cao et al., BMC Evolutionary Biology 14.1 (2014): 1-16.

De Falco et al., Journal of Cellular Physiology 177.4 (1998): 501-506.

Ding et al., International Journal of Molecular Sciences 21.6 (2020): 1960, 28 pages.

Fu et al., Journal of Biological Chemistry 274.49 (1999): 34527-34530.

Grana et al., Proceedings of the National Academy of Sciences 91.9 (1994): 3834-3838.

International Preliminary Report on Patentability for International Application No. PCT/CN2020/134966, dated May 17, 2022, 8 pages.

International Search Report and Written Opinion for International Application No. PCT/CN2020/134966, dated Mar. 10, 2021, 10 pages.

Kushner et al., Can. J. Physiol. Pharmacol., 77, (1999); 79-88.

Wang et al., European Journal of Medicinal Chemistry 158 (2018): 896-916.

Blake et al.. "Studies with Deuterated Drugs," Journal of Pharmaceutical Sciences, 64(3), Mar. 1975, 367-391.

Brickner et al., "Synthesis and Antibacterial Activity of U-100592 and U-100766, Two Oxazolidinone Antibacterial Agents for the Potential Treatment of Multidrug-Resistant Gram-Positive Bacterial Infections", J Med Chem, 39(3), 673-679 (1996).

Kato et al., "Synthesis of Deuterated Mosapride Citrate," Journal of Labelled Compounds and Radiopharmaceuticals, 36(10):927-932 (1995).

Mallesham et al., "Highly Efficient Cul-Catalyzed Coupling of Aryl Bromides with Oxazolidinones Using Buchwald's Protocol: A Short Route to Linezolid and Toloxatone," Organic Letters, 5(7), 963-965 (2003).

* cited by examiner

COMPOUND AS CYCLIN-DEPENDENT KINASE 9 INHIBITOR AND USE THEREOF

CROSS-REFERENCE TO RELATED APPLICATIONS

This application is a U.S. national phase application of International Application No. PCT/CN2020/134966, filed Dec. 9, 2020, claiming the benefit of Chinese Application No. 201911252575.1, filed Dec. 9, 2019, the contents of each of which are incorporated herein by their entireties for all purposes.

TECHNICAL FIELD

The present invention relates to the field of medical technology, in particular, to a novel compound, having the activity as a cyclin-dependent kinase 9 (CDK9) inhibitor, or a pharmaceutically acceptable salt thereof, or a stereoisomer, isotope derivative, or prodrug thereof, and use thereof as a prodrug.

BACKGROUND TECHNOLOGY

Cyclin-dependent kinases (CDKs) are a group of serine/threonine protein kinases that play key roles in regulating the cell cycle and transcription. Up to now, about 20 CDKs and approximately 30 cyclin genes are present in humans (Cao et al. 2014). These CDKs can be activated by cyclins and play different biological functions. Among them, CDK1, CDK2, CDK3, CDK4, and CDK6 directly intervene in the cell cycle. CDK5 does not regulate the cell cycle but plays a key role in the complex migration of post-mitotic neurons. Whereas CDK7 acts only indirectly as an activator of these CDKs. In addition, CDK9, CDK7, and CDK8 are involved in the control of the RNA polymerase II (RNAPII)-mediated transcription. CDK9 was originally discovered in the 1990s and characterized by the Pro-Ile-Thr-Ala-Leu-Arg-Glu motif, and it was identified as a CDC2-related kinase called PITALRE (Grana et al, 1994). With further research, it was found that it should be a cell cycle-dependent protein kinase, and there are two isozymes, CDK9-42 (372 aa, 42 kDa) and CDK9-55 (489 aa, 55 kDa), which bind to four cyclins: cyclin T1, cyclin T2a, cyclin T2b and cyclin K (Fu et al, 1999). CDK9 is not involved in the cell cycle regulation but plays a crucial role in the transcriptional regulation (de Falco & Giordano 1998). CDK9 and its regulatory subunit cyclin T or cyclin K (Fu et al. 1999) are major components of what is known as positive transcription elongation factor b (P-TEFb). CDK9 and cyclin T form the P-TEFb complex, which allows the phosphorylation of the C-terminal domain (CTD) of RNA polymerase II (RNAPII) and activates the productive elongation of mRNA transcripts. CDK9 is a catalytic subunit of positive-transcription elongation factors. When negative transcription elongation factors (NELF, NELFs) are involved in the negative regulation of cellular transcription, the transcription is inhibited, and P-TEFb is recruited to a system in which the transcription elongation is inhibited by the negative transcription elongation factors, it catalyzes the phosphorylation at the C-terminal of RNAPII, and concurrently catalyzes the phosphorylation of the SPT5 subunit of NELFs and the RD subunit of NELF, resulting in the disengagement of the negative transcription elongation factors from the transcription complex, thereby allowing the transcription to continue. Therefore, by inhibition of CDK9 to block the phosphorylation of P-TEFb at the C-terminal region of RNAPII, the transcription is inhibited, and the levels of intracellular mRNA and proteins with short half-lives decrease rapidly, which can cause the tumor cell to apoptosis.

Tumors are usually caused by the expression loss of cyclin-dependent kinase inhibitors (CDKI) or the overexpression of cyclins, making cells unregulated and excessively proliferating. CDK9 inhibitors prevent the phosphorylation at the C-terminal of RNAPII by CDK9, further hinder the departure of NEFL, strengthen the negative inhibition, and ultimately bring about the transcriptional arrest. CDK9 has become a potential protein target for the development of effective cancer therapy, so targeting the inhibition of CDK9 will be beneficial to the treatment of human diseases. Recently, pharmaceutical companies have launched studies on the use of CDK9 inhibitors in the treatment of cancer, including AZD4573, which is now under phase I clinical trial by AstraZeneca, for the treatment of relapsed hematological malignancies, including acute myeloid leukemia (AML) and non-Hodgkin's lymphoma. In addition, Bayer is also studying the application of CDK9 inhibitor BAY-1251152 in advanced solid tumors and hematomas, which is currently in phase I clinical trial.

It is shown according to the published data: WO2009047359 relates to polycyclic amide derivatives that can be used to treat hyperproliferative diseases, WO2014076091 relates to 5-fluoro-N-(pyridin-2-yl)pyridin-2-amine derivatives containing a sulfoximine group (for treating and/or preventing diseases, particularly hyperproliferative diseases, viral-induced infectious diseases and/or cardiovascular diseases) and a preparation process thereof, WO2011116951 discloses substituted triazine derivatives as selective CDK9 inhibitors, WO2011110612 discloses a protein kinase inhibitor for anti-inflammation, having the effect of selectively inhibiting CDK9. Thus, inhibiting CDK9 can theoretically provide therapeutic benefits for the above-mentioned diseases.

Although some small molecule CDK9 inhibitors have been disclosed at the present, it is still necessary to develop new compounds with higher efficacy and less toxicity, and more favorable for drug formation. Through continuous exploration, a compound with the structure shown in the general formula (I) is designed, and in vitro and in vivo experiments show that the compound with the structure shows excellent effects and functions, particularly the in vivo efficacy activity is obviously higher than that of similar molecules in the prior art, and the compound with the structure has a higher possibility of becoming a drug.

SUMMARY OF THE INVENTION

Technical Problems

The present invention aims to solve one of the following technical problems:

- providing a small molecule compound with a novel structure, that is a CDK9 inhibitor with excellent CDK9 inhibitory activity, selectivity, and tumor cell inhibitory activity;
- providing a small molecule compound, which is a CDK9 inhibitor that has better in vivo antitumor activity compared with the known compound, and maintains relatively good CDK9 inhibitory activity, selectivity, and tumor cell inhibitory activity;
- providing a small molecule compound, which is a CDK9 inhibitor that has better safety compared with the known compound, and maintains relatively good CDK9 inhibitory activity, selectivity, and tumor cell inhibitory activity;

providing a small molecule compound, which is a CDK9 inhibitor that has better in vivo antitumor activity and better safety compared with known compounds; and providing a small molecule compound, which is a CDK9 inhibitor that has better in vivo antitumor activity and better safety compared with known compounds, and maintains relatively good CDK9 inhibitory activity, selectivity, and tumor cell inhibitory activity.

Technical Solutions to the Present Disclosure

The present disclosure aims to provide a compound or a pharmaceutically acceptable salt thereof, or a stereoisomer, isotope derivative, or prodrug thereof, and also provides use of the compound or a pharmaceutically acceptable salt thereof, or a stereoisomer, isotope derivative, or prodrug thereof as a cyclin-dependent kinase 9 (CDK9) inhibitor.

Specifically, the present disclosure provides a compound represented by formula (I) or a pharmaceutically acceptable salt thereof, or a stereoisomer, isotope derivative, or prodrug thereof,

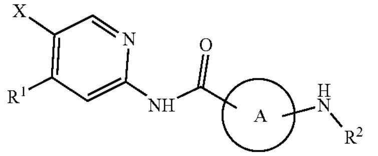

(I)

wherein,

X is Cl or F, preferably F;

$R^1$ is a substituted or unsubstituted aryl or a substituted or unsubstituted heteroaryl; the term "substituted" in $R^1$ refers to being substituted by 1, 2, 3, 4, or 5 group(s) each independently selected from —F, —Cl, —Br, $—NH_2$, —OH, —SH, —CN, $—NO_2$, $—N_3$, —C≡CH, —COOH, $—R^3$, $—(CH_2)_wO(CH_2)_nR^3$, $—(CH_2)_wNH(CH_2)_nR^3$, $—(CH_2)_wNR^3(CH_2)_nR^4$, $—(CH_2)_wS(CH_2)_nR^3$, $—(CH_2)_wC(O)(CH_2)_nR^3$, $—(CH_2)_wC(O)O(CH_2)_nR^3$, $—(CH_2)_wOC(O)(CH_2)_nR^3$, $—(CH_2)_wC(O)NH(CH_2)_nR^3$, $—(CH_2)_wNHC(O)(CH_2)_nR^3$, $—(CH_2)_wC(O)NR^3(CH_2)_nR^4$, $—(CH_2)_wNR^3C(O)(CH_2)_nR^4$, $—(CH_2)_wOS(O)_2(CH_2)_nR^3$ and $—(CH_2)_wS(O)_2O(CH_2)_nR^3$; wherein w and n, at each occurrence, are each independently selected from 0, 1, 2, 3 and 4; $R^3$ and $R^4$ are each independently selected from a substituted or unsubstituted aryl, a substituted or unsubstituted heteroaryl, a substituted or unsubstituted $C_{1-6}$alkyl, a substituted or unsubstituted $C_{1-6}$haloalkyl, a substituted or unsubstituted $C_{2-6}$alkenyl, a substituted or unsubstituted $C_{2-6}$alkynyl, a substituted or unsubstituted $C_{1-6}$alkyloxy, a substituted or unsubstituted $C_{1-6}$haloalkyloxy, a substituted or unsubstituted cycloalkyl, and a substituted or unsubstituted heterocycloalkyl, or when $R^3$ and $R^4$ are both attached to the same nitrogen atom, $R^3$, $R^4$ and the nitrogen atom to which they are attached together form a substituted or unsubstituted heterocycloalkyl; the term "substituted" in $R^3$ and $R^4$ refers to being substituted by 1, 2 or 3 group(s) each independently selected from —F, —Cl, —Br, $—NH_2$, —OH, —SH, —CN, $—NO_2$, $—N_3$, —C—CH, —COOH, $C_{1-6}$alkyl, $C_{1-6}$haloalkyl, $C_{1-6}$alkyloxy, $C_{1-6}$haloalkyloxy and the like;

Ring A is a substituted or unsubstituted cycloalkyl or a substituted or unsubstituted heterocycloalkyl; the term "substituted" in ring A refers to being substituted by 1, 2, 3, 4, or 5 group(s) each independently selected from —F, —Cl, —Br, OH, $NH_2$, SH, CN, $NO_2$, $—N_3$, —C—CH, COOH, $R^5$, OR, $—NHR^5$, $—NR^5R^6$, —SR, $—NHCOR^5$, $—CONHR^5$, $—NHS(O)_2R^5$, $—S(O)_2NHR^5$, $—NR^5S(O)_2R^6$, and $—S(O)_2NR^5R^6$, or one, two or more $—CH_2—$ group(s) in the structure of ring A may optionally be substituted by —C(O)— group(s); wherein $R^5$ and $R^6$ are independently $C_{1-6}$alkyl or $C_{1-6}$haloalkyl;

$R^2$ is selected from H, $R^7$, $—(CH_2)_xR^7$, $—(CH_2)_xNH(CH_2)_yR^7$, $—(CH_2)_xO(CH_2)_yR^7$, $—(CH_2)_xNR^7(CH_2)_yR^8$, $—(CH_2)_xC(O)(CH_2)_yH$, $—(CH_2)_xC(O)(CH_2)_yR^7$, $—(CH_2)_xS(O)_2(CH_2)_yR^7$, $—(CH_2)_xC(O)C(O)(CH_2)_yR^7$, $—(CH_2)_xS(O)_2NH_2$, $—(CH_2)_xNHS(O)_2H$, $—(CH_2)_xS(O)_2NH(CH_2)_yR^7$, $—(CH_2)_xNHS(O)_2(CH_2)_y R^7$, $—(CH_2)_xS(O)_2NR^7(CH_2)_yR^8$, $—(CH_2)_xNR^7S(O)_2(CH_2)_yR^8$, $—(CH_2)_xC(O)O(CH_2)_yR^7$, $—(CH_2)_xOC(O)(CH_2)_yR^7$, $—(CH_2)_xC(O)NH_2$, $—(CH_2)_xNHC(O)H$, $—(CH_2)_xC(O)NH(CH_2)_yR^7$, $—(CH_2)_xNHC(O)(CH_2)_yR^7$, $—(CH_2)_xC(O)NR^7(CH_2)_yR^8$ and $—(CH_2)_xNR^7C(O)(CH_2)_yR^8$; wherein one, two or more $—CH_2—$ group(s) may optionally be substituted by —C(O)— group(s); x and y, in each occurrence, are each independently selected from 0, 1, 2, 3 and 4;

$R^7$ and $R^8$ are independently selected from the following substituted or unsubstituted groups: $R^9$, $OR^9$, $—R^{10}—O—R^9$, $—R^{10}—NH—R^9$, $—R^{10}—C(O)—R^9$, $—R^{10}—NHC(O)—R^9$, $—R^{10}—C(O)NH—R^9$, $—R^{10}—S—R^9$, $—R^{10}—S(O)—R^9$, $—R^{10}—S—C(O)—R^9$, cycloalkyl, heterocycloalkyl, aryl, heteroaryl, $—R^{10}$-aryl, $—R^{10}$-heteroaryl, $—O—R^{10}$-aryl, $—O—R^{10}$-heteroaryl, $—R^{10}—O$-aryl, $—R^{10}—O$-heteroaryl, -cycloalkyl-aryl, -cycloalkyl-heteroaryl, -heterocycloalkyl-aryl, -heterocycloalkyl-heteroaryl, $C_{2-6}$alkenyl and $C_{2-6}$alkynyl, or when $R^7$ and $R^8$ are both attached to the same nitrogen atom, $R^7$ and $R^8$ and the nitrogen atom to which they are attached together form a substituted or unsubstituted heterocycloalkyl; wherein $R^9$ is $C_{1-6}$alkyl, $R^{10}$ is $C_{1-6}$alkylene, $C_{2-6}$alkenylene or $C_{2-6}$alkynylene; the term "substituted" in $R^7$ and $R^8$ refers to being substituted by 1, 2 or 3 group(s) each independently selected from —F, —Cl, —Br, —OH, $—NH_2$, —SH, —CN, $—NO_2$, $—N_3$, —C—CH, —COOH, $C_{1-6}$alkyl, $C_{1-6}$alkyloxy, $C_{1-6}$haloalkyl, $C_{1-6}$haloalkyloxy, —NHCN, $—NHCONH_2$, $NHC(O)CH_3$, $N(CH_3)_2$, $N(C_2H_5)_2$, $—SC(O)CH_3$, $—OC(O)—C_{1-6}$alkyl and the like; Preferably, the isotope derivative is a derivative in deuterated form.

The definitions of "aryl", "heteroaryl", "cycloalkyl" and "heterocycloalkyl" in the present disclosure are shown in the part "Definitions" as follows.

In preferable embodiments, the aryl preferably contains 6-10 carbon atoms, the cycloalkyl preferably contains 3-6 carbon atoms, the heteroaryl is preferably a 5- to 10-membered heteroaryl, and the heterocycloalkyl is preferably a 3- to 8-membered heterocycloalkyl; the heteroaryl or the heterocycloalkyl preferably contains one, two or three heteroatom(s) each independently selected from N, O and S, with the remainder being carbon atom(s).

As described above, "w", "n", "x", and "y" in the present disclosure can be each independently selected from 0, 1, 2, 3, and 4.

When "w" and "n", or "x" and "y" concurrently exist in a group, specifically, the combinations of numerical values "w" and "n", and "x" and "y" can be selected from (0,0), (0,1), (0,2), (0,3), (0,4), (1,0), (1,1), (1,2), (1,3), (1,4), (2,0), (2,1), (2,2), (2,3), (2,4), (3,0), (3,1), (3,2), (3,3), (3,4), (4,0), (4,1), (4,2), (4,3), and (4,4). The combination of numerical values applies to each relevant group in the definitions of $R^1$ and $R^2$. For example, $—(CH_2)_wO(CH_2)_nR^3$ in the definition of $R^1$ is equivalent to the disclosure of the groups such as $—OR^3$, $—OCH_2R^3$, $—O(CH_2)_2R^3$, $—O(CH_2)_3R^3$, $—O(CH_2)_4R^3$, $—CH_2OR^3$, $—CH_2OCH_2R^3$, $—CH_2O(CH_2)_2$ $R^3$, $—CH_2O(CH_2)_3R^3$, $—CH_2O(CH_2)_4R^3$, $—(CH_2)_2$ $OR^3$, $—(CH_2)_2OCH_2R^3$, $—(CH_2)_2O(CH_2)_2R^3$, $—(CH_2)_2(CH_2)_3$ $R^3$, $—(CH_2)_2O(CH_2)_4R^3$, $—(CH_2)_3OR^3$, $—(CH_2)_3OCH_2R^3$, $—(CH_2)_3O(CH_2)_3R^3$, $—(CH_2)_3O(CH_2)_3$ $R^3$, $—(CH_2)_3O(CH_2)_4R^3$, $—(CH_2)_4OR^3$, $—(CH_2)_4OCH_2R^3$, $—(CH_2)_4O(CH_2)_4R^3$, $—(CH_2)_4O(CH_2)_3R^3$, $—(CH_2)_4O(CH_2)_4R^3$ and the like. Similarly, other relevant groups in $R^1$ and/or $R^2$ also disclose such choices, and will not be described in detail.

Preferably, the present disclosure provides a compound or a pharmaceutically acceptable salt thereof, or a stereoisomer, isotope derivative, or prodrug thereof, wherein ring A is selected from a substituted or unsubstituted 4- to 6-membered cycloalkyl, a substituted or unsubstituted 4- to 6-membered heterocycloalkyl, a substituted or unsubstituted 5- to 6-membered cycloalkyl, and a substituted or unsubstituted 5- to 6-membered heterocycloalkyl; more preferably, ring A is a substituted or unsubstituted 5- to 6-membered cycloalkyl, or a substituted or unsubstituted 5- to 6-membered heterocycloalkyl; still more preferably, ring A is a substituted or unsubstituted 5- to 6-membered cycloalkyl; in another preferable embodiment, ring A is selected from cyclohexanyl, tetrahydropyrrolyl, piperidinyl, piperazinyl, and morpholinyl, more preferably, ring A is cyclohexanyl or tetrahydropyrrolyl.

Further preferably, the present disclosure provides a compound or a pharmaceutically acceptable salt thereof, or a stereoisomer, isotope derivative, or prodrug thereof, the term "substituted" in ring A refers to being substituted by 1, 2, 3, 4, or 5 group(s) each independently selected from —F, —Cl, —Br, OH, $NH_2$, SH, CN, $R^5$, and $OR^5$, wherein, $R^5$ is $C_{1-6}$alkyl or $C_{1-6}$alkyloxy, $R^5$ can further be $C_{1-4}$alkyl or $C_{1-4}$alkyloxy.

Further preferably, the present invention provides a compound or a pharmaceutically acceptable salt thereof, or a stereoisomer, isotope derivative, or prodrug thereof, wherein said compound has a structure shown by formula (II):

(II)

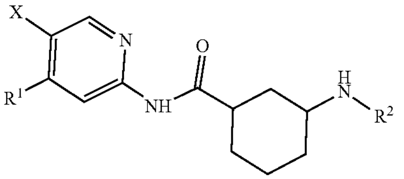

wherein $R^1$, $R^2$, and X are shown in formula (I).

Further preferably, the present disclosure provides a compound or a pharmaceutically acceptable salt thereof, or a stereoisomer, isotope derivative, or prodrug thereof, wherein said compound has a structure shown by formula (IIa):

(IIa)

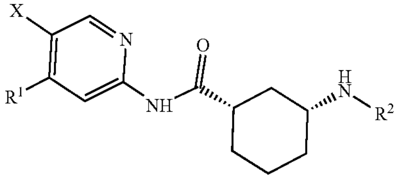

wherein $R^1$, $R^2$, and X are shown in formula (I).

Further preferably, the present disclosure provides a compound or a pharmaceutically acceptable salt thereof, or a stereoisomer, isotope derivative, or prodrug thereof, wherein said compound has a structure shown by formula (III):

(III)

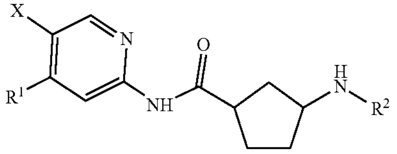

wherein $R^1$, $R^2$, and X are shown in formula (I).

Further preferably, the present disclosure provides a compound or a pharmaceutically acceptable salt thereof, or a stereoisomer, isotope derivative, or prodrug thereof, wherein said compound has a structure shown by formula (IIIa):

(IIIa)

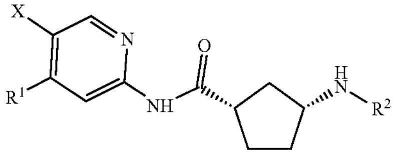

wherein $R^1$, $R^2$, and X are shown in formula (I).

Preferably, the present disclosure provides a compound or a pharmaceutically acceptable salt thereof, or a stereoisomer, isotope derivative, or prodrug thereof, wherein $R^1$ is a substituted or unsubstituted 6- to 10-membered aryl, or a substituted or unsubstituted 5- to 10-membered heteroaryl; the heteroaryl contains 1 or 2 heteroatoms each independently selected from N and O; the number of the substituent is 1, 2, or 3.

Further preferably, the present disclosure provides a compound or a pharmaceutically acceptable salt thereof, a stereoisomer, isotope derivative, or prodrug thereof, wherein $R^1$ is selected from a substituted or unsubstituted benzene ring, a substituted or unsubstituted pyridine ring, a substituted or unsubstituted indole ring, a substituted or unsubstituted indazole ring, a substituted or unsubstituted benzofuran ring, and a substituted or unsubstituted pyrrolopyridine ring; preferably selected from a substituted or unsubstituted benzene ring, a substituted or unsubstituted pyridine ring, a substituted or unsubstituted indole ring, a substituted or unsubstituted benzofuran ring, and a substituted or unsubstituted pyrrolopyridine ring; more preferably selected from a substituted benzene ring, a substituted pyridine ring, an unsubstituted indole ring, an unsubstituted benzofuran ring, and an unsubstituted pyrrolopyridine ring; still more preferably a substituted benzene ring.

Further preferably, the present disclosure provides a compound or a pharmaceutically acceptable salt thereof, or a stereoisomer, isotope derivative, or prodrug thereof, wherein the substituents of said $R^1$ are each independently selected from —F, —Cl, —OH, —$NH_2$, —$R^3$, —$(CH_2)_wO(CH_2)_nR^3$ and —$(CH_2)_wOC(O)(CH_2)_nR^3$; w and n, in each occurrence, are each independently selected from 0, 1 and 2, wherein $R^3$ is defined as described in formula (I). Preferably, the substituents of said $R^1$ are each independently selected from —F, —Cl, —OH, —$R^3$, and —$(CH_2)_wO(CH_2)_nR^3$; further preferably, the substituents of said $R^1$ are each independently selected from —F, —OH, —$R^3$, and —$(CH_2)_wO(CH_2)_nR^3$. For example, when $R^1$ is a substituted benzene ring, the substituent is selected from —F, —OH, and alkoxy, preferably it is substituted by one or two fluorine atoms and one —OH or alkoxy.

Preferably, the present disclosure provides a compound or a pharmaceutically acceptable salt thereof, or a stereoisomer, isotope derivative, or prodrug thereof, wherein $R^3$ and $R^4$ are each independently selected from a substituted or unsubstituted 6-membered aryl, a substituted or unsubstituted 5- to 6-membered heteroaryl, a substituted or unsubstituted $C_{1-3}$alkyl, a substituted or unsubstituted $C_{1-3}$alkyloxy, a substituted or unsubstituted $C_{3-6}$cycloalkyl, and a substituted or unsubstituted $C_{3-6}$heterocycloalkyl, or when $R^3$ and $R^4$ are both attached to the same nitrogen atom, $R^3$, $R^4$ and the nitrogen atom to which they are attached together form a 3- to 7-membered substituted or unsubstituted heterocycloalkyl; the heterocycloalkyl contains one or two heteroatom(s) independently selected from N, O and S; the term "substituted" in $R^3$ and $R^4$ refers to being substituted by 1, 2 or 3 substituent(s) each independently selected from —F, —Cl, —Br, —OH, —$CH_3$, —$C_2H_5$, —$OCH_3$, and —$OC_2H_5$; preferably, $R^3$ and $R^4$ are each independently selected from a substituted or unsubstituted $C_{1-3}$alkyl, and a substituted or unsubstituted $C_{1-3}$alkyloxy.

More preferably, the present disclosure provides a compound or a pharmaceutically acceptable salt thereof, or a stereoisomer, isotope derivative, or prodrug thereof, wherein $R^3$ and $R^4$ are each independently selected from the following substituted or unsubstituted groups: benzene ring, pyridine ring, methyl, ethyl, propyl, isopropyl, methyloxy, ethyloxy, propyloxy, isopropyloxy, cyclopropyl, cyclobutyl, cyclopentyl and cyclohexyl, the term "substituted" in $R^3$ and $R^4$ refers to being substituted by 1, 2 or 3 substituent(s) each independently selected from —F, —Cl, —Br, —OH, —$CH_3$, —$C_2H_5$, —$OCH_3$, and —$OC_2H_5$, preferably, $R^3$ and $R^4$ are each independently selected from the following substituted or unsubstituted groups: methyl, ethyl, isopropyl, methyloxy, ethyloxy, isopropyloxy, cyclopropyl, and pyridine ring; more preferably, $R^3$ and $R^4$ are each independently selected from the following substituted or unsubstituted groups: methyl, ethyl, isopropyl, methyloxy, ethyloxy, and isopropyloxy; still more preferably, $R^3$ and $R^4$ are each independently selected from the following substituted or unsubstituted groups: methyl, and methyloxy.

Preferably, the present disclosure provides a compound or a pharmaceutically acceptable salt thereof, or a stereoisomer, isotope derivative, or prodrug thereof, wherein $R^2$ is selected from $R^7$, —$(CH_2)_xR^7$, —$(CH_2)_xNH(CH_2)_yR^7$, —$(CH_2)_xC(O)(CH_2)_yR^7$, —$(CH_2)_xS(O)_2(CH_2)_yR^7$, —$(CH_2)_x$ $C(O)C(O)(CH_2)_yR^7$, —$(CH_2)_xC(O)O(CH_2)_yR^7$, —$(CH_2)_xC(O)NH(CH_2)_yR^7$, —$(CH_2)_xC(O)NR^7(CH_2)_yR^8$ and —$(CH_2)_xNR^7C(O)(CH_2)_yR^8$, wherein $R^7$ and $R^8$ are as defined in formula (I). More preferably, $R^2$ is selected from $R^7$, —$(CH_2)_xR^7$, —$(CH_2)_xC(O)(CH_2)_yR^7$, —$(CH_2)_xS(O)_2(CH_2)_yR^7$, —$(CH_2)_xC(O)C(O)(CH_2)_yR^7$, —$(CH_2)_xC(O)O(CH_2)_yR^7$, and —$(CH_2)_xC(O)NH(CH_2)_yR^7$; still more preferably, $R^2$ is selected from $R^7$, —$(CH_2)_xR^7$, and —$(CH_2)_xC(O)(CH_2)_yR^7$.

Further preferably, the present disclosure provides a compound or a pharmaceutically acceptable salt thereof, a stereoisomer, isotope derivative, or prodrug thereof, wherein $R^7$ and $R^8$ are each independently selected from the following substituted or unsubstituted groups: $R^9$, $OR^9$, —$R^{10}$—O—$R^9$, —$R^{10}$—NH—$R^9$, —$R^{10}$—C(O)—$R^9$, —$R^{10}$—NHC(O)—$R^9$, —$R^{10}$—C(O)NH—$R^9$, —$R^{10}$—S—$R^9$, —$R^{10}$—S—C(O)—$R^9$, $C_{3-6}$cycloalkyl, 3- to 6-membered heterocycloalkyl, $C_{6-10}$aryl, 5- to 10-membered heteroaryl, —$R^{10}$—$C_{6-10}$aryl, —$R^{10}$-5- to 10-membered heteroaryl, —O—$R^{10}$—$C_{6-10}$aryl, —O—$R^{10}$-5- to 10-membered heteroaryl, —$R^{10}$—O—$C_{6-10}$aryl, —$R^{10}$—O-5- to 10-membered heteroaryl, $C_2$-6alkene and $C_{2-6}$alkyne, or when $R^7$ and $R^8$ are both attached to the same nitrogen atom, $R^7$ and $R^8$ and the nitrogen atom to which they are attached together form a substituted or unsubstituted 3- to 6-membered heterocycloalkyl; wherein $R^9$ is $C_{1-6}$alkyl, $R^{10}$ is $C_{1-6}$alkylene, $C_{2-6}$alkenylene or $C_{2-6}$alkynylene; the term "substituted" in $R^7$ and $R^8$ refers to being substituted by 1, 2 or 3 group(s) each independently selected from —F, —Cl, —Br, —OH, —$NH_2$, —SH, —CN, $C_{1-3}$alkyl, $C_{1-3}$alkyloxy, $C_{1-3}$haloalkyl, $C_{1-3}$haloalkyloxy, —NHCN, —$NHCONH_2$, $NHC(O)CH_3$, $N(CH_3)_2$, $N(C_2H_5)_2$, —$SC(O)CH_3$, —OC(O)—$C_{1-6}$alkyl and the like; preferably, $R^7$ is independently selected from the following substituted or unsubstituted groups: $R^9$, $OR^9$, —$R^{10}$—O—$R^9$, —$R^{10}$—NHC(O)—$R^9$, $C_{3-6}$cycloalkyl, 3- to 6-membered heterocycloalkyl, $C_{6-10}$aryl, 5- to 10-membered heteroaryl, $C_2$-6alkene and $C_{2-6}$alkyne, or when $R^7$ and $R^8$ are both attached to the same nitrogen atom, $R^7$ and $R^8$ and the nitrogen atom to which they are attached together form a substituted or unsubstituted 3- to 6-membered heterocycloalkyl; more preferably, $R^7$ is independently selected from the following substituted or unsubstituted groups: $R^9$, $OR^9$, —$R^{10}$—O—$R^9$, $C_{3-6}$cycloalkyl, 3- to 6-membered heterocycloalkyl, $C_{6-10}$aryl, and 5- to 10-membered heteroaryl; still more preferably, $R^7$ is independently selected from the following substituted or unsubstituted groups: $R^9$, $OR^9$, —$R^{10}$—O—$R^9$, $C_{3-6}$cycloalkyl, and 3- to 6-membered heterocycloalkyl; the term "substituted" in $R^7$ refers to being substituted by 1, 2 or 3 group(s) each independently selected from —F, —Cl, —Br, —OH, —$NH_2$, —SH, —CN, $C_{1-3}$alkyl, $C_{1-3}$alkyloxy, $C_{1-3}$haloalkyl, $C_{1-3}$haloalkyloxy, —NHCN, —$NHCONH_2$, $NHC(O)CH_3$, $N(CH_3)_2$, $N(C_2H_5)_2$, —$SC(O)CH_3$, —OC(O)—$C_{1-6}$alkyl and the like; preferably the term "substituted" in $R^7$ refers to being substituted by 1, 2 or 3 group(s) each independently selected from —F, —OH, —$NH_2$, —SH, —CN, $C_{1-3}$alkyl, $C_{1-3}$alkyloxy, $C_{1-3}$haloalkyl, $NHC(O)CH_3$, $N(CH_3)_2$, —OC(O)—$C_{1-6}$alkyl and like; more preferably, the term "substituted" in $R^7$ refers to being substituted by 1, 2 or 3 group(s) each independently selected from —F, —OH, —$NH_2$, —CN, $C_{1-3}$alkyl, $C_{1-3}$alkyloxy and the like.

Further preferably, the present disclosure provides a compound or a pharmaceutically acceptable salt thereof, a stereoisomer, isotope derivative, or prodrug thereof, wherein $R^7$ and $R^8$ are each independently selected from the following substituted or unsubstituted groups: methyl, ethyl, propyl, isopropyl, butyl, pentyl, methyloxy, ethyloxy, propyloxy, isopropyloxy, —$CH_2OCH_3$, —$CH_2OCH_2CH_3$, —$CH_2CH_2OCH_3$, —$CH_2CH_2OCH_2CH_3$, cyclopropyl, cyclobutyl, cyclopentyl, cyclohexyl, aziridinyl, azetidinyl, pyrrolidinyl, piperidyl, oxiranyl, oxetanyl, oxacyclopentyl, oxacyclohexyl, phenyl, pyridyl, pyrazolyl, oxazolyl, isoxazolyl, thienyl, thiazolyl, benzyl, phenylethyl, vinyl, propenyl, ethynyl, and propynyl. Preferably, $R^7$ is independently selected from the following substituted or unsubstituted groups: methyl, ethyl, methyloxy, ethyloxy, cyclopropyl, cyclobutyl, azetidinyl, piperidyl, oxetanyl, oxacyclohexyl, phenyl, pyridyl, pyrazolyl, isoxazolyl, thienyl, thiazolyl, benzyl, vinyl, propenyl, and ethynyl; more preferably, $R^7$ is independently selected from the following substituted or unsubstituted groups: methyl, ethyl, methyloxy, cyclopropyl, cyclobutyl, piperidyl, oxetanyl, oxacyclohexyl, pyridyl, pyrazolyl, isoxazolyl, vinyl, propenyl, and ethynyl; still more preferably, $R^7$ is independently selected from methyl, ethyl, cyclopropyl, piperidyl, oxetanyl, pyrazolyl, vinyl, propenyl, and ethynyl; further more preferably, $R^7$ is independently selected from methyl, ethyl, and cyclopropyl. The term "substituted" in $R^7$ and $R^8$ refers to being substituted by 1, 2 or 3 group(s) each independently selected from —F, —Cl, —Br, —OH, —$NH_2$, —SH, —CN, $C_{1-3}$alkyl, $C_{1-3}$alkyloxy, $C_{1-3}$haloalkyl, $C_{1-3}$haloalkyloxy, —NHCN, —$NHCONH_2$, $NHC(O)CH_3$, $N(CH_3)_2$, $N(C_2H_5)_2$, —$SC(O)CH_3$, —OC(O)—$C_{1-6}$alkyl and like; preferably, the term "substituted" in $R^7$ and $R^8$ refers to being substituted by 1, 2 or 3 group(s) each independently selected from —F, —OH, —SH, —CN, $C_{1-3}$alkyl, $C_{1-3}$alkyloxy, $C_{1-3}$haloalkyloxy, $NHC(O)CH_3$, $N(CH_3)_2$, $N(C_2H_5)_2$, —OC(O)—$C_{1-6}$alkyl and like; more preferably, the term "substituted" in $R^7$ and $R^8$ refers to being substituted by 1, 2 or 3 group(s) each independently selected from —F, —OH, —$NH_2$, —CN, $C_{1-3}$haloalkyloxy and like; still more preferably, the term "substituted" in $R^7$ and $R^5$ refers to being substituted by 1, 2 or 3 group(s) each independently selected from —F, —OH, —CN and the like.

Further preferably, the present disclosure provides a compound or a pharmaceutically acceptable salt thereof, a stereoisomer, isotope derivative, or prodrug thereof, wherein $R^9$ is $C_{1-4}$alkyl, $R^{10}$ is $C_{1-4}$alkylene.

Preferably, the present disclosure provides a compound or a pharmaceutically acceptable salt thereof, or a stereoisomer, isotope derivative, or prodrug thereof, wherein the compounds have the following structures:

1

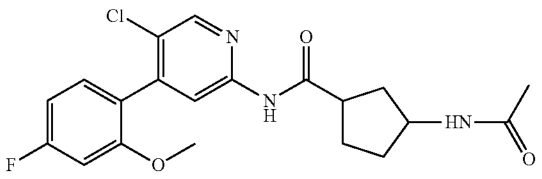

2

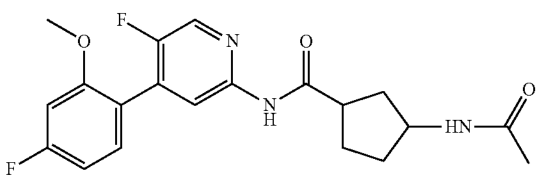

3

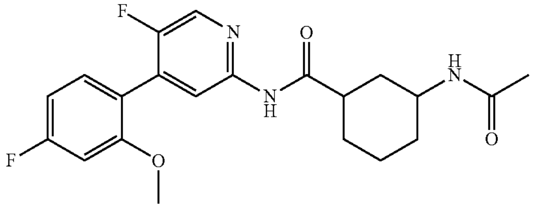

-continued

4

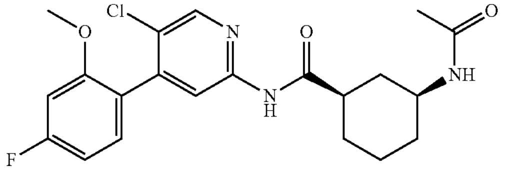

5

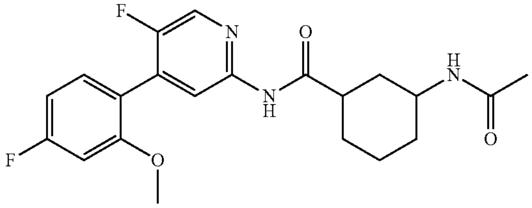

6

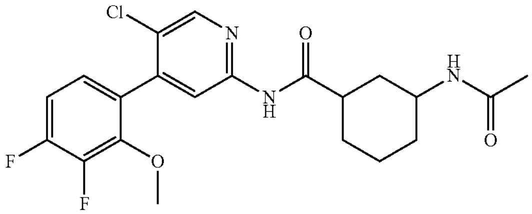

7

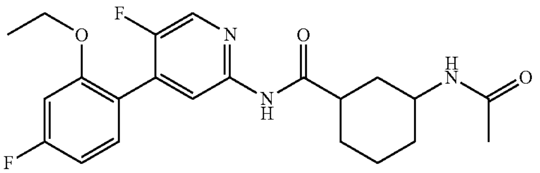

8

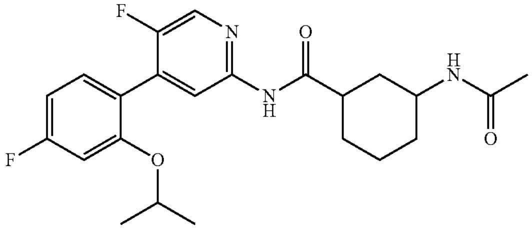

9

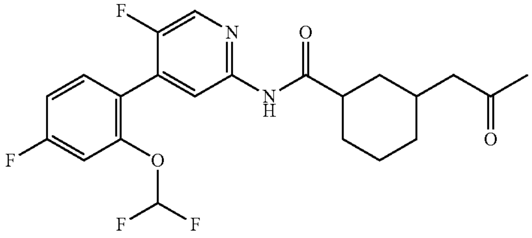

10

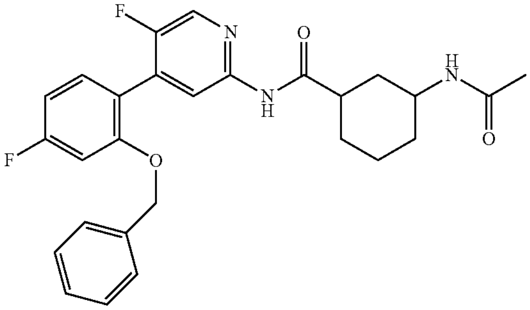

-continued
11
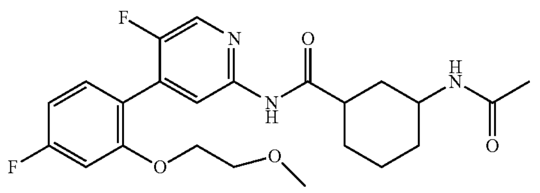
12
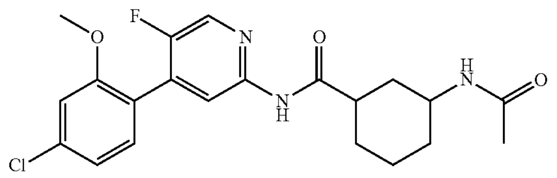
13
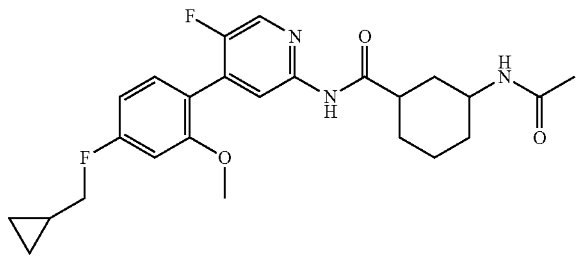
14
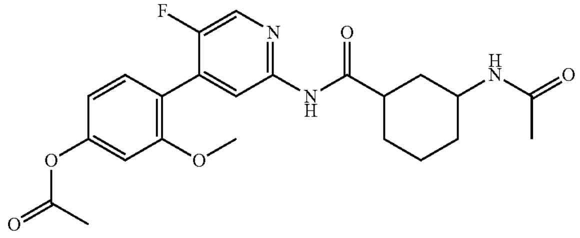
15
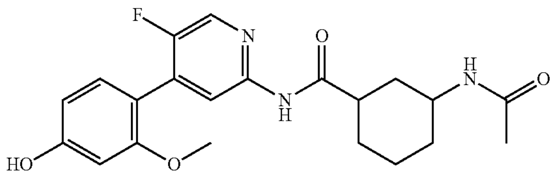
16
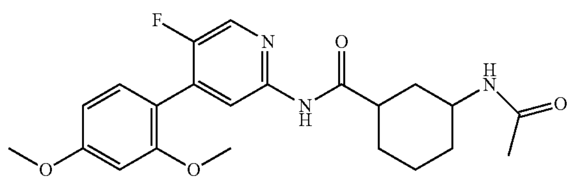
17
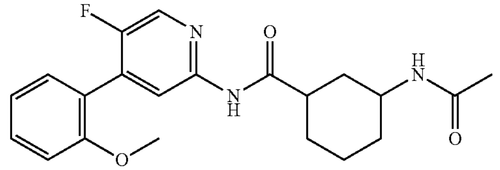
-continued
18
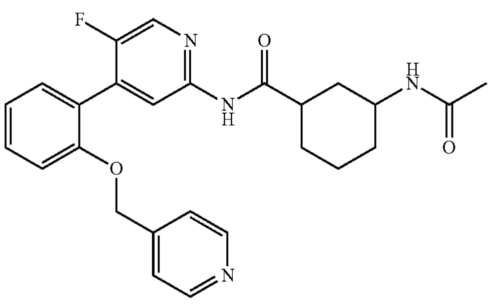
19
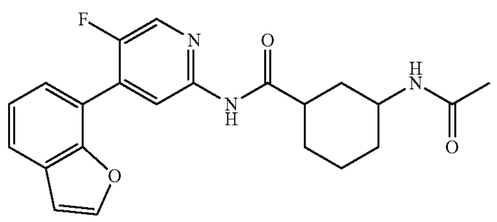
20
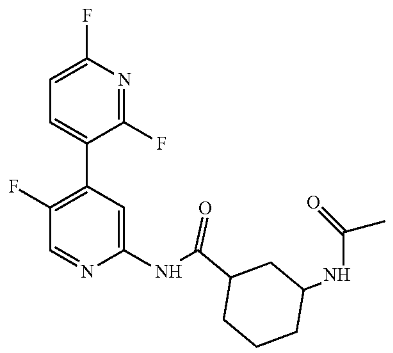
21
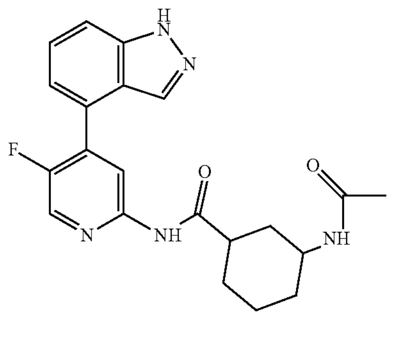
22
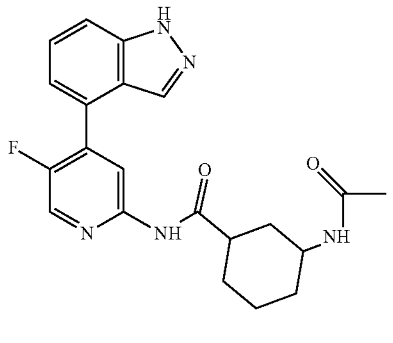

-continued
23
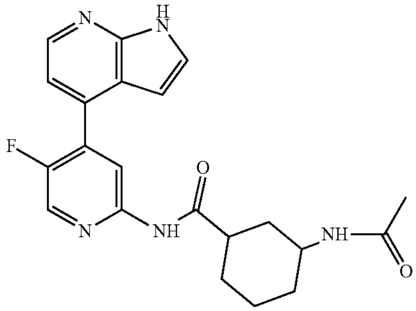
24
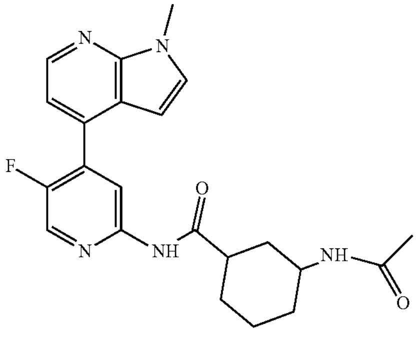
25
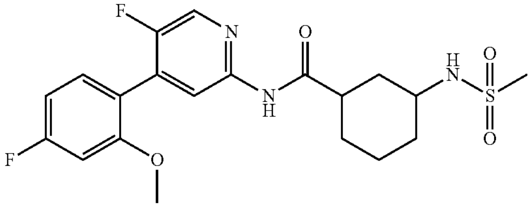
26
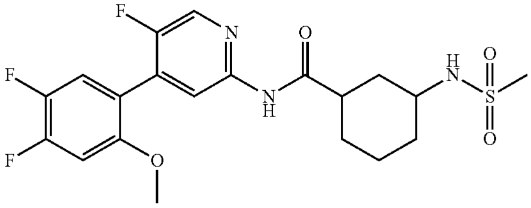
27
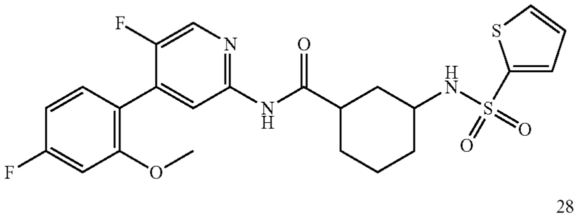
28
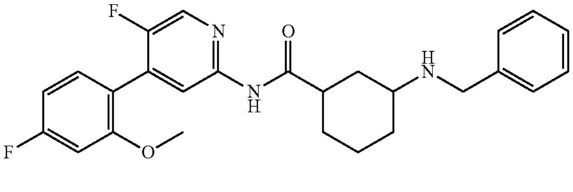
-continued
29
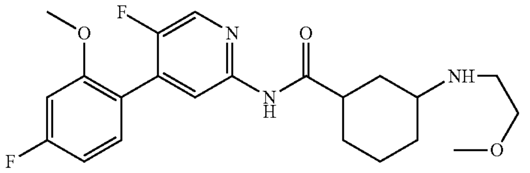
30
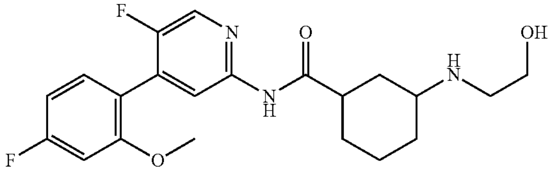
31
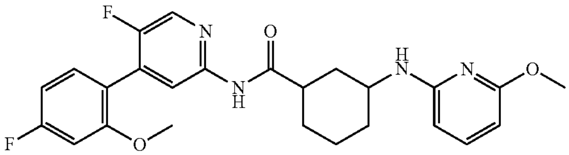
32
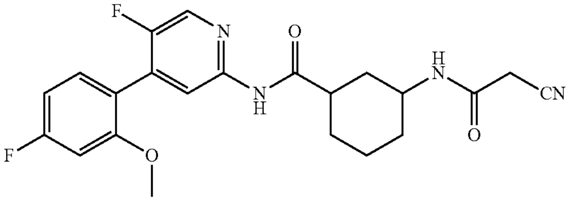
33
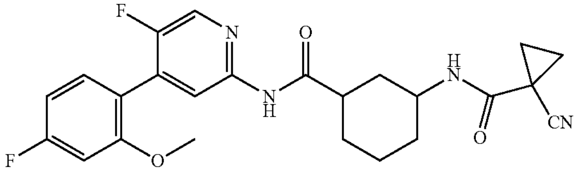
34
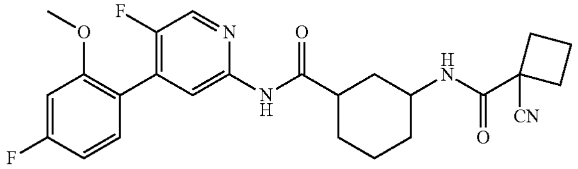
35
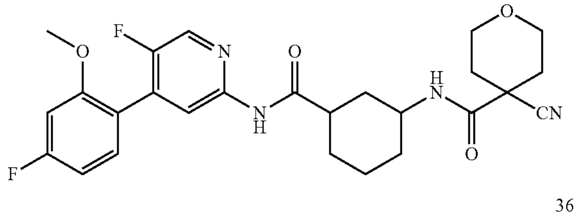
36
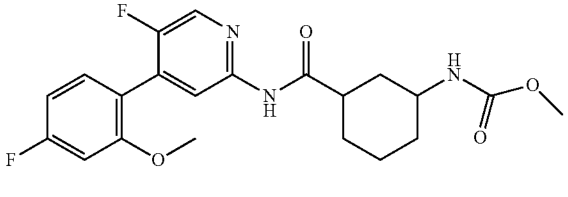

-continued
37
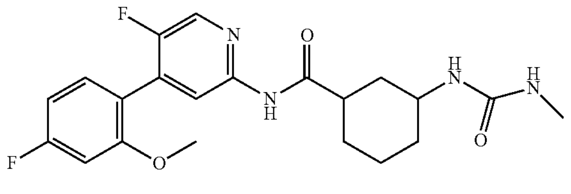
38
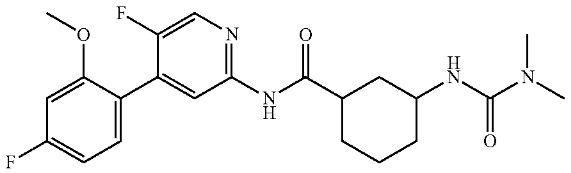
39
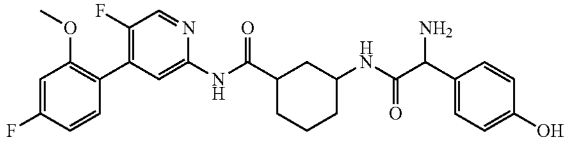
40
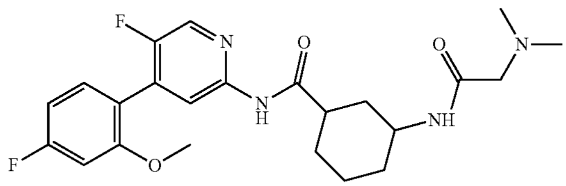
41
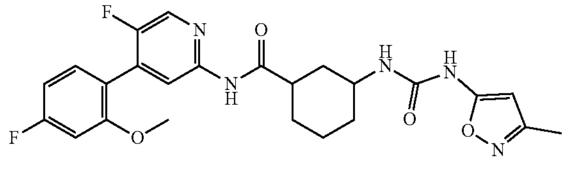
42
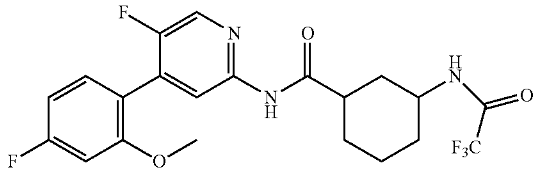
43
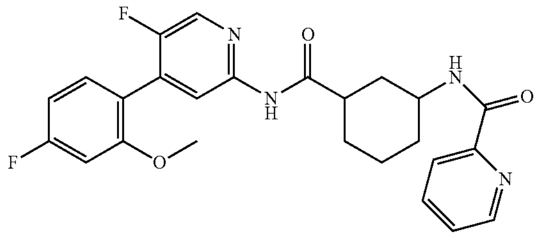
-continued
44
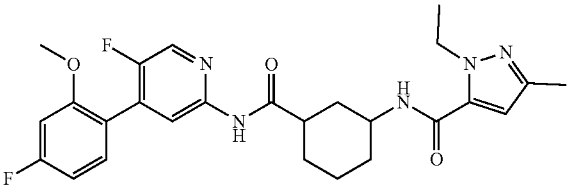
45
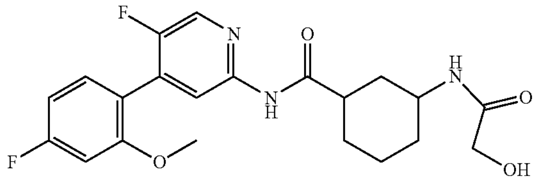
46
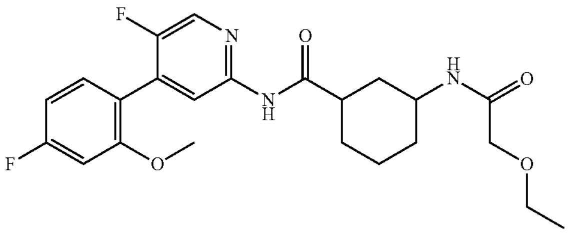
47
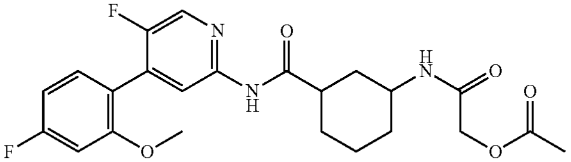
48
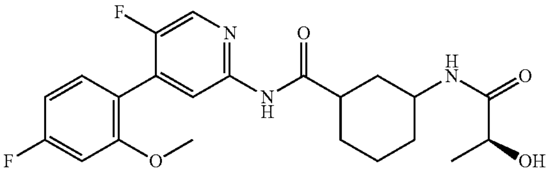
49
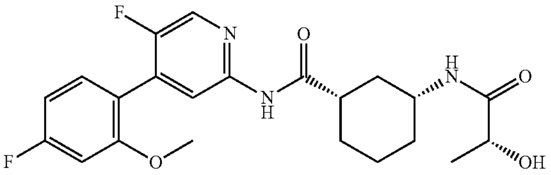
50
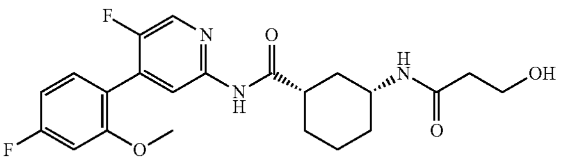

-continued
51
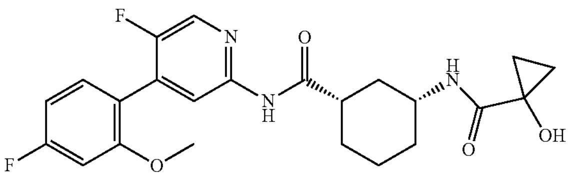
52
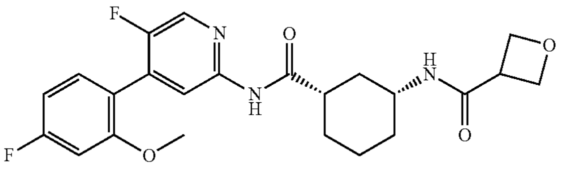
53
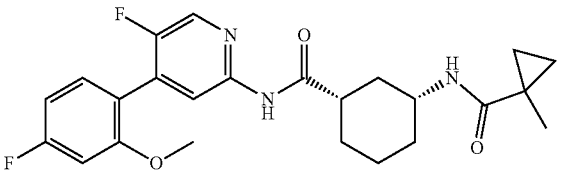
54
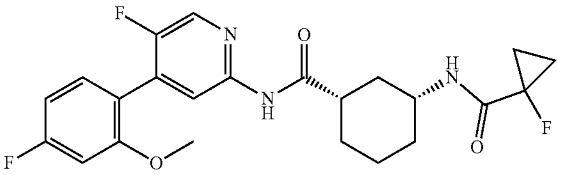
55
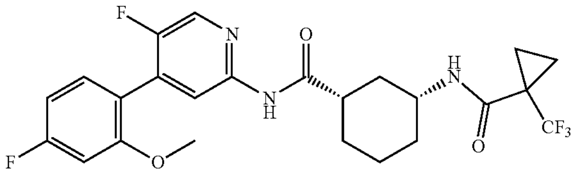
56
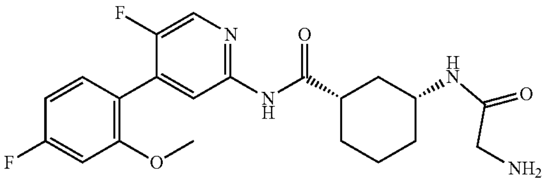
57
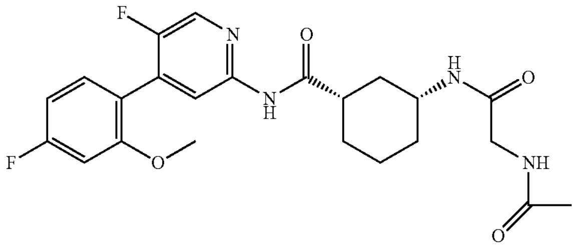
-continued
58
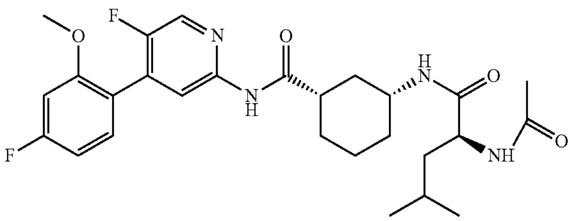
59
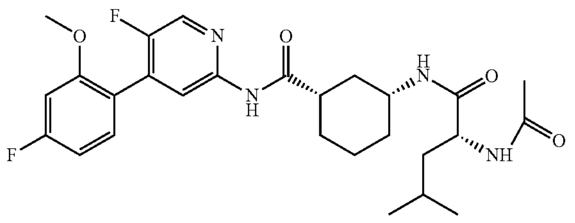
60
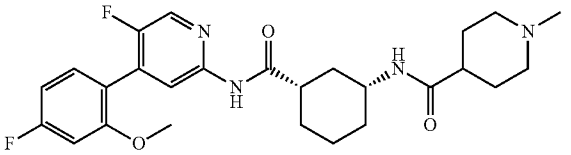
61
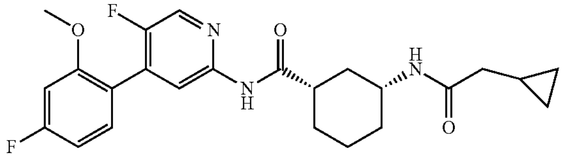
62
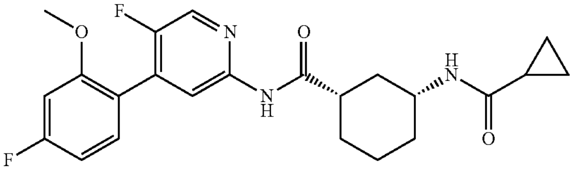
63
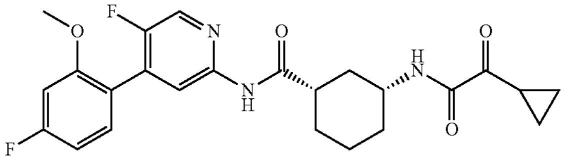
64
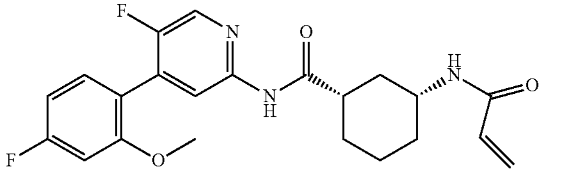

-continued
65
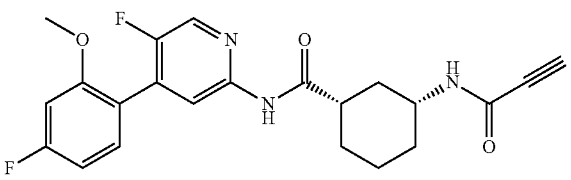
66
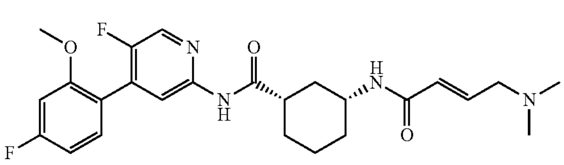
67
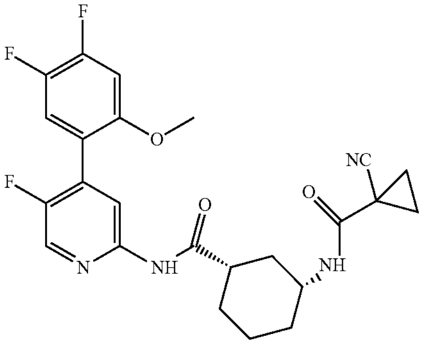
68
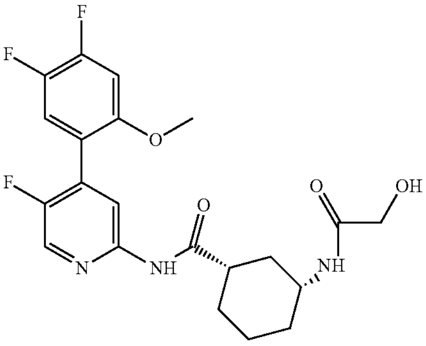
69
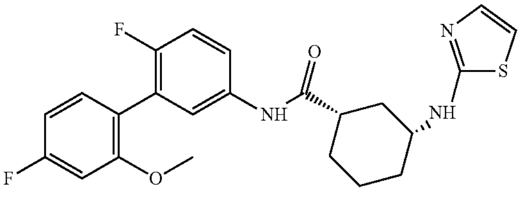
70
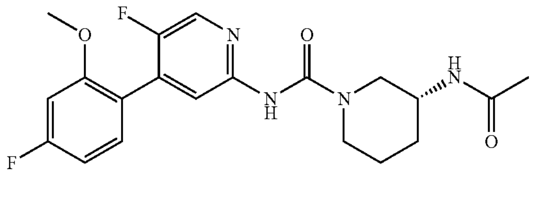
-continued
71
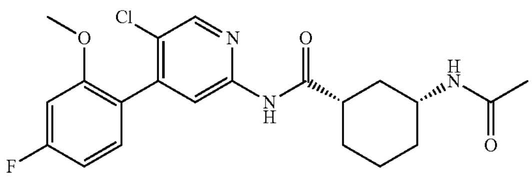
72
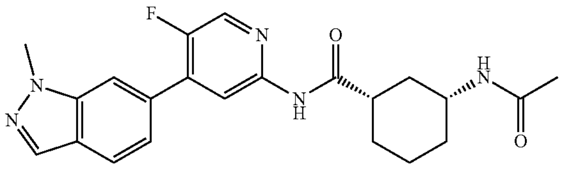
73
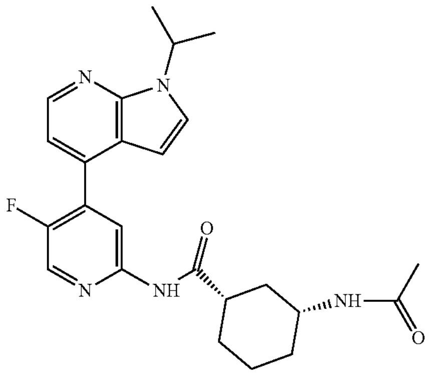
74
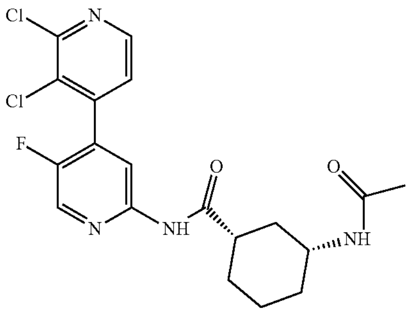
75
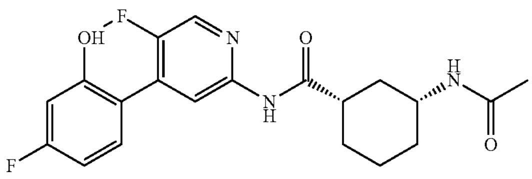
76
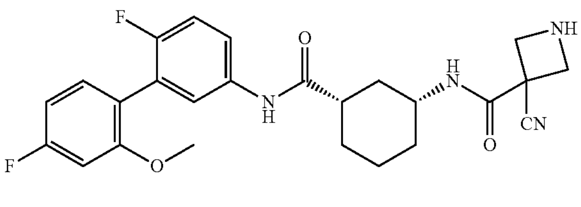

-continued
77
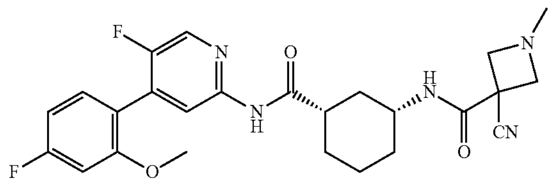
78
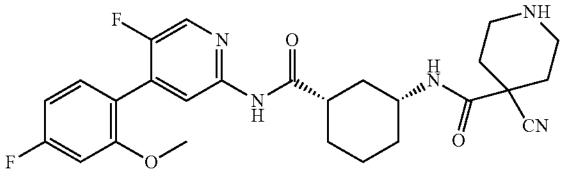
79
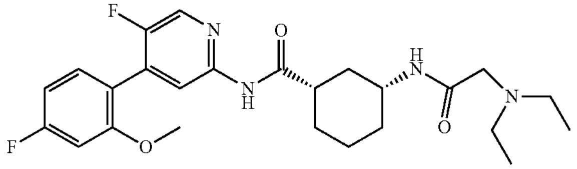
80
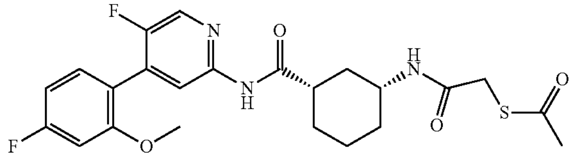
81
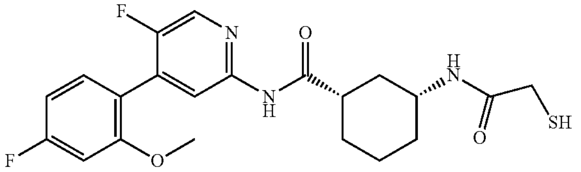
82
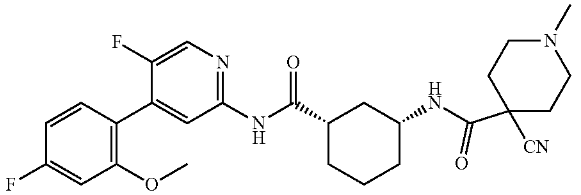
83
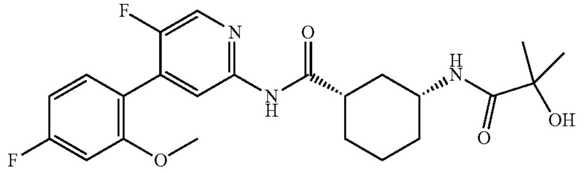
-continued
84
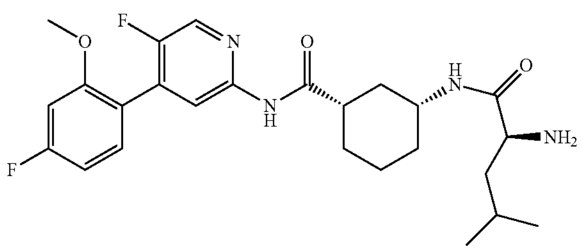
85
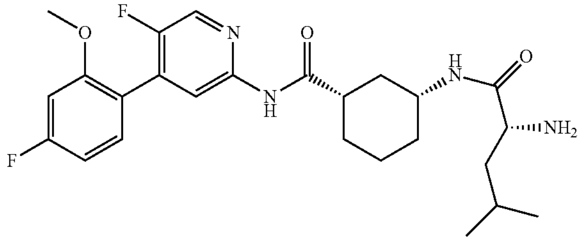
86
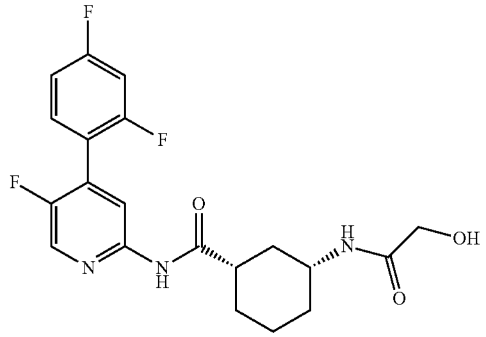
87
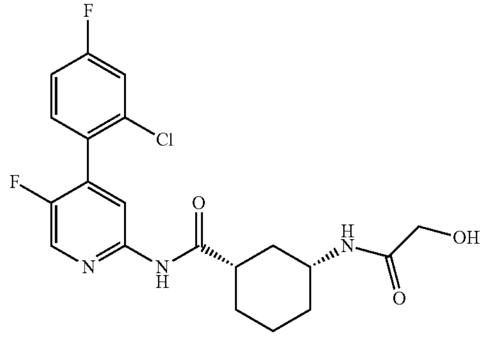
88
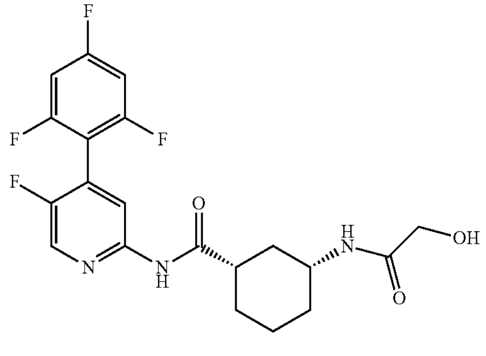

-continued

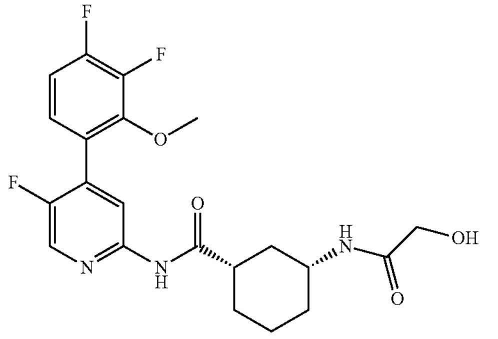

89

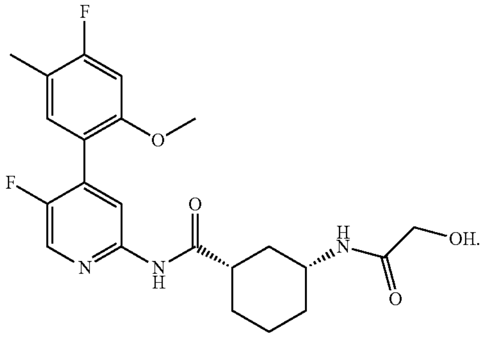

90

Another aspect of the present disclosure also provides a pharmaceutical composition comprising the compound according to the present disclosure or a pharmaceutically acceptable salt thereof, or a stereoisomer, isotope derivative, or prodrug thereof. Another aspect of the present disclosure also provides the use of the compound according to the present disclosure or a pharmaceutically acceptable salt thereof, or a stereoisomer, isotope derivative, or prodrug thereof, or the pharmaceutical composition of the present disclosure in the manufacture of a medicament for preventing and/or treating diseases mediated by the activity of cyclin-dependent kinase 9 (CDK9); preferably, the disease is a hyperproliferative disease or an inflammatory disease; further preferably, the hyperproliferative disease is a hematological tumor or a solid tumor; still more preferably, the hematological tumor is leukemia; still more preferably, the leukemia is acute myeloid leukemia.

Another aspect of the present disclosure also provides the compound according to the present invention or a pharmaceutically acceptable salt thereof, or a stereoisomer, isotope derivative, or prodrug thereof, or the pharmaceutical composition of the present disclosure for use in a medicament.

Further, according to the use in medicament provided by the present disclosure, the medicament is used for treating hyperproliferative diseases or inflammatory diseases.

Further, according to the use in medicament provided by the present disclosure, the hyperproliferative disease is a hematological tumor or a solid tumor; preferably, the hematological tumor is leukemia; more preferably, the leukemia is acute myeloid leukemia.

Another aspect of the present disclosure also provides the use of the compound according to the present disclosure or a pharmaceutically acceptable salt thereof, or a stereoisomer, isotope derivative, or prodrug thereof, or the pharmaceutical composition of the present disclosure for use in preventing and/or treating diseases mediated by the activity of cyclin-dependent kinase 9 (CDK9); preferably, the disease is a hyperproliferative disease or an inflammatory disease; more preferably, the hyperproliferative disease is a hematological tumor or a solid tumor; still more preferably, the hematological tumor is leukemia; further more preferably, the leukemia is acute myeloid leukemia.

Another aspect of the present disclosure also provides the compound according to the present disclosure or a pharmaceutically acceptable salt thereof, or a stereoisomer, isotope derivative, or prodrug thereof, or the pharmaceutical composition of the present disclosure for use in treating hyperproliferative diseases or inflammatory diseases, preferably, the hyperproliferative disease is a hematological tumor or a solid tumor; more preferably, the hematological tumor is leukemia; still more preferably, the leukemia is acute myeloid leukemia.

Another aspect of the present disclosure also provides a method for the treatment of diseases and/or conditions, comprising administering the above-mentioned compound or a pharmaceutically acceptable salt thereof, or a stereoisomer, isotope derivative, or prodrug thereof, or the pharmaceutical composition to a subject in need, said diseases and/or conditions in the subject is diseases mediated by the activity of cyclin-dependent kinase 9 (CDK9); preferably, the disease is a hyperproliferative disease or an inflammatory disease; more preferably, the hyperproliferative disease is a hematological tumor or a solid tumor; still more preferably, the hematological tumor is leukemia; further more preferably, the leukemia is acute myeloid leukemia.

Another aspect of the present disclosure also provides a method for the treatment of diseases and/or conditions, comprising administering the above-mentioned compound or a pharmaceutically acceptable salt thereof, or a stereoisomer, isotope derivative, or prodrug thereof, or the pharmaceutical composition to a subject in need, said disease and/or condition in the subject is a hyperproliferative disease or an inflammatory disease; preferably, the hyperproliferative disease is a hematological tumor or a solid tumor; more preferably, the hematological tumor is leukemia; still more preferably, the leukemia is acute myeloid leukemia.

The compound of the present disclosure can have an optical activity. The compound of the present disclosure may be present as a racemate, an optical isomer, or a mixture thereof. In order to synthesize the optical isomer of the compound of the present disclosure, it may be prepared from the optical isomer of the starting material or may be prepared by separation of the racemate of the compound of the present disclosure.

Definition

The term "alkyl" refers to a monovalent saturated aliphatic hydrocarbon group, a straight or branched chain group containing 1-20 carbon atoms, preferably containing 1-10 carbon atoms (i.e. $C_{1-10}$alkyl), more preferably containing 1-8 carbon atoms ($C_{1-8}$alkyl), still more preferably containing 1-6 carbon atoms (i.e. $C_{1-6}$alkyl). For example, "$C_{1-6}$alkyl" refers to such a group, which is an alkyl group, and the carbon atom number of the carbon chain is between 1 and 6 (specifically 1, 2, 3, 4, 5, or 6). Examples include, but are not limited to, methyl, ethyl, n-propyl, isopropyl, n-butyl, isobutyl, tert-butyl, sec-butyl, n-pentyl, neopentyl, 1,1-dimethylpropyl, 1,2-dimethylpropyl, 2,2-dimethylpropyl, 1-ethylpropyl, 2-methylbutyl, 3-methylbutyl, n-hexyl, n-heptyl, n-octyl, and the like.

The term "cycloalkyl" refers to a monocyclic saturated aliphatic hydrocarbon group having a specified number of carbon atoms, preferably containing 3-12 carbon atoms (i.e.

$C_{3-12}$cycloalkyl), more preferably containing 3-10 carbon atoms ($C_{3-10}$cycloalkyl), still more preferably 3-6 carbon atoms ($C_{3-6}$cycloalkyl), 4-6 carbon atoms ($C_{4-6}$cycloalkyl), and 5-6 carbon atoms ($C_{5-6}$cycloalkyl). Examples include, but are not limited to, cyclopropyl, cyclobutyl, cyclopentyl, cyclohexyl, methylcyclopropyl, 2-ethyl-cyclopentyl, dimethylcyclobutyl, and the like.

The term "alkyloxy" refers to an —O-alkyl group, wherein the alkyl is as defined above, i.e. containing 1-20 carbon atoms, preferably 1-10 carbon atoms, more preferably 1-8 carbon atoms, still more preferably 1-6 carbon atoms (specifically 1, 2, 3, 4, 5 or 6). Representative examples include, but are not limited to methyloxy, ethyloxy, propyloxy, isopropyloxy, butyloxy, 1-methylpropyloxy, 2-methylpropyloxy, tert-butyloxy, pentyloxy, 1-methylbutyloxy, 2-methylbutyloxy, 3-methylbutyloxy, 1,1-dimethylpropyloxy, 1,2-dimethylpropyloxy, 2,2-dimethylpropyloxy, 1-ethylpropyloxy and the like.

The term "halogen" or "halo" refers to F, Cl, Br, and I. The term "haloalkyl" refers to an alkyl group as defined above in which one, two, more, or all of the hydrogen atom(s) is/are replaced by halogen atom(s). Representative examples of haloalkyl include $CCl_3$, $CF_3$, $CHCl_2$, $CH_2Cl$, $CH_2Br$, $CH_2I$, $CH_2CF_3$, $CF_2CF_3$, and the like.

The term "heterocycle group" refers to a saturated or partially unsaturated monocyclic, bicyclic or polycyclic cyclohydrocarbon substituent, which is a non-aromatic structure, containing 3-20 ring atoms (wherein 1, 2, 3, or more ring atom(s) is/are selected from N, O and S and the remaining ring atoms are C), preferably containing 3-12 ring atoms ($C_{3-12}$ heterocycle group), more preferably containing 3-10 ring atoms ($C_{3-10}$ heterocycle group), or 3-8 ring atoms ($C_{3-8}$ heterocycle group), or 3-6 ring atoms ($C_{3-6}$ heterocycle group), or 4-6 ring atoms ($C_{4-6}$ heterocycle group), or 5-6 ring atoms ($C_5$_6 heterocycle group); and preferably having 1-4 heteroatoms, more preferably 1-3 (i.e. 1, 2 or 3) heteroatoms. Examples of monocyclic heterocycle groups include pyrrolidinyl, imidazolidinyl, tetrahydrofuranyl, dihydropyrrolyl, piperidinyl, piperazinyl, pyranyl, and the like. Polycyclic heterocycle groups include spiro, fused, and bridged heterocycle groups.

The term "heterocycloalkyl" refers to a saturated "heterocycle group" as defined above, containing 3-20 ring atoms (wherein 1, 2, 3, or more ring atom(s) is/are selected from N, O, and S and the remaining ring atoms are C), preferably containing 3-12 ring atoms ($C_{3-12}$ heterocycloalkyl), more preferably containing 3-10 ring atoms ($C_{3-10}$ heterocycloalkyl), or 3-8 ring atoms ($C_{3-8}$ heterocycloalkyl), or 3-7 ring atoms ($C_{3-7}$ heterocycloalkyl), or 3-6 ring atoms ($C_{3-6}$ heterocycloalkyl), or 4-6 ring atoms ($C_{4-6}$ heterocycloalkyl), or 5-6 ring atoms ($C_{5-6}$ heterocycloalkyl); and preferably having 1-4 heteroatoms, more preferably 1-3 (i.e. 1, 2 or 3) heteroatoms. Examples include aziridinyl, oxiranyl, thiiranyl, azetidinyl, oxetanyl, thietanyl, pyrrolidinyl, tetrahydrofuranyl, oxacyclohexanyl, piperidinyl, piperazinyl, morpholinyl, thiomorpholinyl, dioxanyl, dithiacyclohexyl, oxazolidinyl, thiazolidinyl, pyrazolidinyl, imidazolidinyl and the like.

The term "aryl" refers to monocyclic, bicyclic, and tricyclic aromatic carbon ring systems containing 6-16 carbon atoms, or 6-14 carbon atoms, or 6-12 carbon atoms, or 6-10 carbon atoms, preferably 6-10 carbon atoms. The term "aryl" may be used interchangeably with the term "aromatic ring". Examples of aryl groups may include but are not limited to, phenyl, naphthalenyl, anthracenyl, phenanthrenyl, pyrenyl, or the like.

The term "heteroaryl" refers to an aromatic monocyclic or polycyclic ring system containing a 5- to 12-membered structure, or preferably a 5- to 10-membered structure, a 5- to 8-membered structure, and more preferably a 5- to 6-membered structure, wherein 1, 2, 3 or more ring atom(s) is/are heteroatom(s) and the remaining atoms are carbon, the heteroatoms are independently selected from O, N, and S, and the number of heteroatom is preferably 1, 2 or 3. Examples of heteroaryl groups include, but are not limited to, furyl, thienyl, oxazolyl, thiazolyl, isoxazolyl, oxadiazolyl, thiadiazolyl, pyrrolyl, pyrazolyl, imidazolyl, triazolyl, tetrazolyl, pyridyl, pyrimidinyl, pyrazinyl, pyridazinyl, thiodiazolyl, triazinyl, phthalazinyl, quinolinyl, isoquinolinyl, pteridyl, purinyl, indolyl, isoindolyl, indazolyl, benzofuranyl, benzothienyl, benzopyridyl, benzopyrimidinyl, benzopyrazinyl, benzimidazolyl, benzophthalazinyl, pyrrolo[2,3-b]pyridyl, imidazo[1,2-a]pyridyl, pyrazolo[1,5-a]pyridyl, pyrazolo[1,5-a]pyrimidinyl, imidazo[1,2-b]pyridazinyl, [1,2,4]triazolo[4,3-b]pyridazinyl, [1,2,4]triazolo[1,5-a]pyrimidyl, [1,2,4]triazolo[1,5-a]pyridyl, and the like.

The term "pharmaceutically acceptable salt" refers to those salts which are, within the scope of sound medical judgment, suitable for use in contact with the tissues of mammals, particularly humans without undue toxicity, irritation, allergic response, and the like, and are commensurate with a reasonable benefit/risk ratio. For example, pharmaceutically acceptable salts of amines, carboxylic acids, and other types of compounds are well known in the art.

The term "salt" includes salts derived from inorganic acids such as hydrochloric acid, sulfuric acid, sulfurous acid, nitric acid, phosphoric acid, hydrobromic acid, and the like, and also includes salts derived from organic acids such as acetic acid, propionic acid, succinic acid, lactic acid, malic acid, tartaric acid, citric acid, methanesulfonic acid, maleic acid, fumaric acid, salicylic acid, and the like. When the compound of the present disclosure is acidic, its corresponding salt can be conveniently prepared from pharmaceutically acceptable non-toxic bases, including inorganic bases and organic bases. Salts derived from such inorganic bases include aluminum salt, ammonium salt, calcium salt, copper (ic and ous) salt, ferric salt, ferrous salt, lithium salt, magnesium salt, zinc salt, and the like. Salts derived from organic non-toxic bases include primary amine salt, secondary amine salt, tertiary amine salt, and the like.

The term "stereoisomer" refers to the isomers produced by the different arrangements of atoms in the molecule in space, including configurational isomers and conformational isomers, wherein configurational isomers in turn include geometrical isomers (or cis-trans isomers) and optical isomers (including enantiomers and diastereomers).

Geometrical isomers may exist in the present compounds. Compounds of this invention may contain carbon-carbon double bonds or carbon-nitrogen double bonds in the E or Z configuration, wherein the term "E" represents higher-order substituents on opposite sides of the carbon-carbon or carbon-nitrogen double bond and the term "Z" represents higher-order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration.

Optical isomers refer to substances with identical molecular structures, similar physical and chemical properties, but different optical rotations.

Compounds of this disclosure may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of the disclosure can exist in isotope-labeled or -enriched form containing one or more atoms having an atomic mass or mass number different from the atomic mass or mass number most abundantly found in nature. Isotopes can be radioactive or nonradioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$), or $^{14}C$ isotopes. Isotope-labeled compounds of this invention can be prepared by the general methods well known to persons having ordinary skills in the art. In this aspect, the relevant literature includes Lizondo, J et al., Drugs Fut, 21(11), 1116 (1996); Brickner, S J et al, J Med Chem, 39(3), 673 (1996); Mallesham, B et al., Org Lett, 5(7), 963 (2003).

Isotope-containing compounds have been used in pharmaceutical research to investigate the in vivo metabolic fate of the compounds by the evaluation of the action mechanism and metabolic pathway of the non-isotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Kushner et al., Can. J. Physiol. Pharmacol., 77, 79-88 (1999); Foster et al., Advances in Drug Research Vol. 14, pp. 2-36, Academic Press, London, 1985; Kato et al., J. Labelled Comp. Radiopharmaceut., 36(10):927-932 (1995)).

In addition, non-radioactive isotope-containing drugs, such as deuterated drugs called "heavy drugs" can be used for the treatment of diseases and conditions. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The substitution with isotopes can be present at any possible site in the molecular structure to obtain isotope derivatives. For example, the substitution with deuterium ($^{2}H$) can be present at any possible site in the molecule to produce derivatives in deuterated form.

Drugs labeled with stable isotopes can alter their physicochemical properties, such as pKa and lipid solubility. If the isotopic substitution affects regions involved in ligand-receptor interactions, then these effects and alterations can affect the pharmacodynamic response of the drug molecule. Although some physical properties of stable-isotope-labeled molecules differ from those of unlabeled molecules, the chemical and biological properties are the same, with one important difference: due to the increased mass of heavy isotopes, the involvement of heavy isotopes and any bond with another atom is stronger than the same bond between the light isotope and that atom. Accordingly, binding an isotope at a site of metabolism or enzymatic transformation can potentially slow the reaction, which can alter pharmacokinetic properties or effects relative to non-isotopic compounds.

Prodrugs are designed derivatives of active drugs that improve some defined, undesirable physical or biological properties. Physical properties are usually related to solubility (too much or insufficient lipid or water solubility) or stability, while problematic biological properties include too fast metabolism or poor bioavailability, which themselves may be related to physicochemical properties.

Prodrugs are usually prepared by: a) formation of ester, hemi-esters, carbonate esters, nitrate esters, amides, hydroxamic acids, carbamates, imines, Mannich bases, phosphates, phosphate esters, and enamines of the active drug, b) functionalizing the drug with azo, glycoside, peptide, and ether functional groups, c) use of aminals, hemi-aminals, polymers, salts, complexes, phosphoramides, acetals, hemiacetals, and ketal forms of the drug. For example, see Andrejus Korolkovas's, "Essentials of Medicinal Chemistry", John Wiley-Interscience Pulications, John Wiley and Sons, New York (1988), pp. 97-118, which is incorporated in its entirety by reference herein. Esters can be prepared from substrates containing either a hydroxyl group or a carboxyl group by general methods known to those skilled in the art. The typical reactions of these compounds are substitutions replacing one of the heteroatoms with another atom. Amides can be prepared from substrates containing either an amino group or a carboxyl group in a similar fashion. Esters can also react with amines or ammonia to form amides. Another way to prepare amides is to heat the carboxylic acid and amine together.

The Beneficial Effects of the Present Disclosure are:

The present disclosure designs a series of compounds with novel structures, which provides a new direction for the treatment of hyperproliferative diseases, especially for treating the development of hematological tumors and solid tumors.

The results of in vitro kinase activity assay and cell assay show that the compounds of the present disclosure have good in vitro kinase inhibitory activities against CDK9, good selectivities for other CDK subunits; and relatively strong inhibitory effect on MV4;11 cells. The preferred compounds of the present disclosure have an $IC_{50}$ below 300 nM, preferably below 200 nM, more preferably below 100 nM, and still more preferably below tens of nM, with respect to the in vitro MV4;11 cell inhibitory activities.

In vitro hERG inhibitory activity assays show that the compounds of the present disclosure have a lower risk of cardiotoxicity.

The in vivo assay results show that, compared with the control compound, the compounds of the present disclosure have better in vivo anti-tumor effect, less toxicity, and a higher possibility of becoming a drug, which provides a better choice for drugs that inhibit the CDK9 target.

The development of the compounds of the present disclosure has expanded the choice of drugs for cancer treatment. In addition, the present disclosure investigates a specific synthesis method, which synthesis method is simple in process, convenient in operation, and conducive to large-scale industrial production and application.

DETAILED DESCRIPTION OF THE DISCLOSURE

The present disclosure is further described below in conjunction with specific examples. It should be understood that these examples are only used to illustrate the present disclosure and not to limit the scope of the present disclosure. The experimental methods without specific conditions in the following examples are performed in accordance with conventional conditions or in accordance with the conditions suggested by the manufacturer. Unless otherwise defined, all professional and scientific terms used herein have the same meanings as those familiar to those skilled in the art. In addition, any methods and materials similar or equivalent to those described herein can be used in the methods of the present disclosure. Preferred implementations and materials shown herein are provided for illustrative purposes only.

Example 1

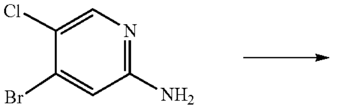

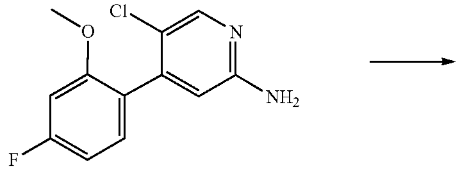

1a

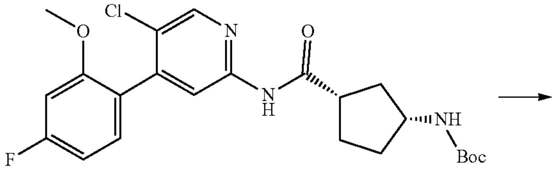

1b

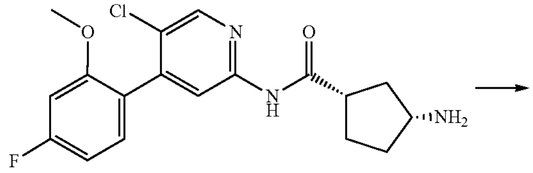

1c

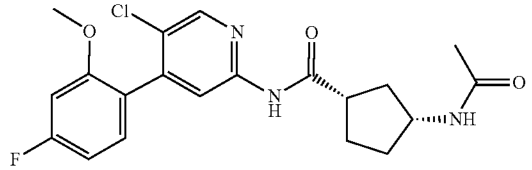

1

Synthesis of Intermediate 1a 4-bromo-5-chloropyridin-2-amine (3.00 g, 14.50 mmol) was dissolved in ethylene glycol dimethyl ether (50 mL) and water (10 mL), followed by adding 4-fluoro-2-methoxyphenylboronic acid (2.50 g, 14.70 mmol), [1,1'-bis(diphenylphosphino)ferrocene]dichloropalladium (1.06 g, 1.45 mmol) and potassium carbonate (6.00 g, 44.10 mmol). The reaction mixture was evacuated and backfilled with N2 (3 times). The reaction mixture was stirred and heated to reflux at 100° C. for 4 hours until no starting material was detected by TLC. The reaction mixture was concentrated under reduced pressure and purified by column chromatography (dichloromethane:methanol=50:1-10:1) to give 1a (3.11 g, yield 85%).

Synthesis of Intermediate 1b 1a (0.89 g, 3.50 mmol) was dissolved in N,N-dimethylformamide (30 mL), and then (1S,3R)-3-[(tert-butyloxycarbonyl)amino]cyclopentanecarboxylic acid (0.85 g, 3.50 mmol), 2-(7-azabenzotriazol-1-yl)-N,N,N',N'-tetramethyluronium hexafluorophosphate (1.60 g, 4.20 mmol) and N,N-diisopropylethylamine (0.91 g, 7.00 mmol) were added. The reaction mixture was stirred overnight at room temperature until no starting material was detected by TLC. To the reaction mixture was added water (100 mL). The mixture was extracted with ethyl acetate (50 mL×3). The organic phases were combined, washed with saturated sodium chloride (50 mL×2), and dried over anhydrous sodium sulfate. The solvent was removed under reduced pressure. The crude product was purified by column chromatography (dichloromethane:methanol=50:1-20:1) to give 1b (0.96 g, yield 59%).

Synthesis of Intermediate 1c 1b (0.96 g, 2.07 mmol) was dissolved in dichloromethane (30 mL), and then trifluoroacetic acid (2 mL) was added in an ice bath. The reaction mixture was stirred overnight at room temperature until no starting material was detected by TLC. To the reaction solution was added water (100 mL). Then the mixture was adjusted with an aqueous saturated sodium bicarbonate solution to a pH of 9-10 and extracted with dichloromethane (50 mL×3). The organic phases were combined, washed with saturated sodium chloride (50 mL×2), and dried over anhydrous sodium sulfate. The solvent was removed under reduced pressure. The crude product was purified by column chromatography (dichloromethane:methanol=50:1-8:1) to give 1c (0.66 g, yield 88%).

Synthesis of Final Product 1

1c (0.66 g, 1.80 mmol) was dissolved in dichloromethane (35 mL), and then acetic anhydride (0.92 g, 9.00 mmol) and triethylamine (0.91 g, 9.00 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride (50 mL×2), and dried over anhydrous sodium sulfate. The solvent was removed under reduced pressure. The crude product was purified by column chromatography (petroleum ether:ethyl acetate=10:1-2:1) to give the final product 1 (0.48 g, yield 64%). MS m/z (ESI): 406.1 $[M+H]^+$. $^1$H NMR (600 MHz, $CDCl_3$) δ 9.16 (s, 1H), 8.28-8.25 (m, 2H), 7.55 (s, 1H), 7.18 (d, J=7.2 Hz, 1H), 6.79-6.71 (m, 2H), 4.44 (s, 1H), 3.80 (s, 3H), 2.98 (t, J=4.8 Hz, 1H), 2.20-2.17 (m, 3H), 1.97 (s, 3H), 1.88-1.82 (m, 3H).

Example 2

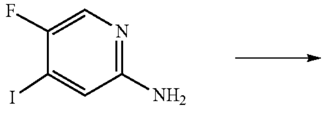

-continued

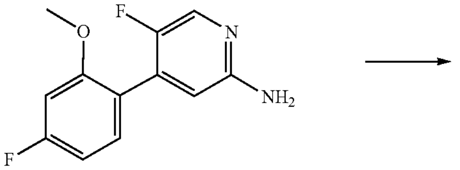

2a

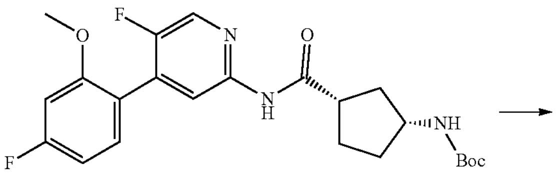

2b

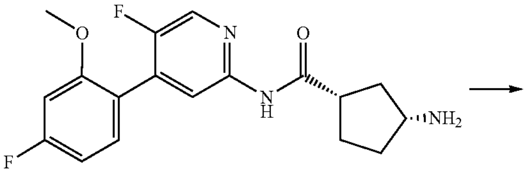

2c

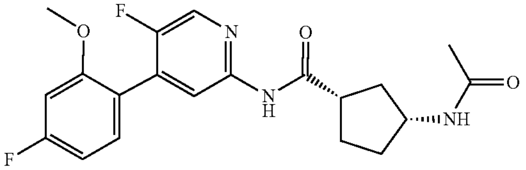

2

Synthesis of Intermediate 2a 5-fluoro-4-iodopyridin-2-amine (1.00 g, 4.20 mmol) was dissolved in ethylene glycol dimethyl ether (20 mL) and water (4 mL), and then 4-fluoro-2-methoxyphenylboronic acid (0.71 g, 4.20 mmol), [1,1'-bis(diphenylphosphino)ferrocene]dichloropalladium (0.31 g, 0.42 mmol) and potassium carbonate (1.70 g, 12.60 mmol) were added. The mixture was evacuated and backfilled with $N_2$ (3 times). The reaction mixture was stirred and brought to reflux at 100° C. for 4 hours. No starting material was detected by TLC. The mixture was concentrated under reduced pressure. The crude product was purified by column chromatography (dichloromethane:methanol=50:1-10:1) to give 2a (0.80 g, yield 81%).

Synthesis of Intermediate 2b 2a (0.80 g, 3.40 mmol) was dissolved in N,N-dimethylformamide (30 mL), and then (1S,3R)-3-[(tert-butyloxycarbonyl)amino]cyclopentanecarboxylic acid (0.83 g, 3.40 mmol), 2-(7-azabenzotriazol-1-yl)-N,N,N',N'-tetramethyluronium hexafluorophosphate (1.56 g, 4.10 mmol) and N,N-diisopropylethylamine (0.88 g, 6.80 mmol) were added. The reaction mixture was stirred overnight at room temperature, and no starting material was detected by TLC. To the reaction solution was added water (100 mL). The mixture was extracted with ethyl acetate (50 mL×3). The organic phases were combined, washed with saturated sodium chloride (50 mL×2), and dried over anhydrous sodium sulfate. The solvent was removed under reduced pressure. The crude product was purified by column chromatography (dichloromethane:methanol=50:1-20:1) to give 2b (0.82 g, yield 54%).

Synthesis of Intermediate 2c 2b (0.82 g, 1.83 mmol) was dissolved in dichloromethane (30 mL), and then trifluoroacetic acid (2 mL) was added in an ice-water bath. The reaction mixture was stirred overnight at room temperature until no starting material was detected by TLC. To the reaction solution was added water (100 mL). Then the mixture was adjusted with an aqueous saturated sodium bicarbonate solution to a pH of 9-10 and extracted with dichloromethane (50 mL×3). The organic phases were combined, washed with saturated sodium chloride (50 mL×2), and dried over anhydrous sodium sulfate. The solvent was removed under reduced pressure. The crude product was purified by column chromatography (dichloromethane:methanol=50:1-8:1) to give 2c (0.59 g, yield 93%).

Synthesis of final product 2

2c (0.59 g, 1.70 mmol) was dissolved in dichloromethane (35 mL), and then acetic anhydride (0.87 g, 8.50 mmol) and triethylamine (0.86 g, 8.50 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride (50 mL×2), and dried over anhydrous sodium sulfate. The solvent was removed under reduced pressure. The crude product was purified by column chromatography (petroleum ether:ethyl acetate=10:1-2:1) to give the final product 2 (0.42 g, yield 63%).

MS m/z (ESI): 390.2 $[M+H]^+$.

$^1H$ NMR (600 MHz, $CDCl_3$) δ 9.20 (s, 1H), 8.32 (s, 1H), 8.12 (s, 1H), 7.30 (d, J=6.6 Hz, 1H), 6.82-6.75 (m, 3H), 4.44 (s, 1H), 3.84 (s, 3H), 2.99 (q, J=3.6 Hz,1H), 2.22-2.15 (m, 3H), 1.99 (s, 3H), 1.89-1.85 (m, 3H).

Example 3

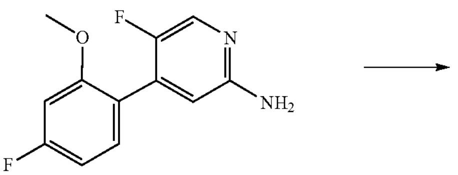

2a

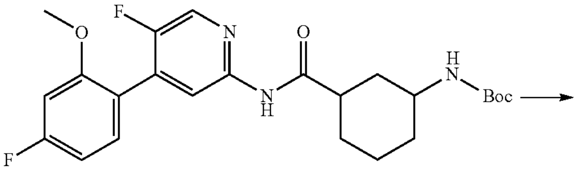

3a

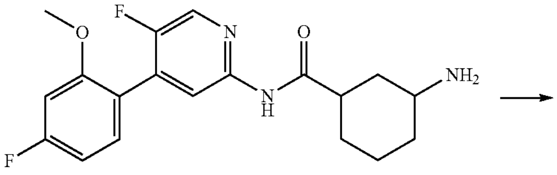

3b

-continued

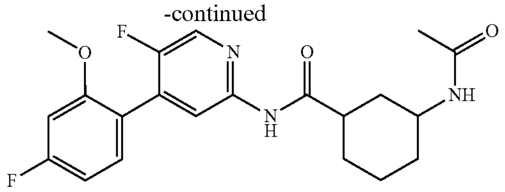

3

Synthesis of Intermediate 3a 2a (0.80 g, 3.40 mmol) was dissolved in N,N-dimethylformamide (30 mL), and then cis-3-[(tert-butyloxycarbonyl)amino]cyclohexanecarboxylic acid (0.83 g, 3.40 mmol), 2-(7-azabenzotriazol-1-yl)-N,N,N',N'-tetramethyluronium hexafluorophosphate (1.56 g, 4.10 mmol) and N,N-diisopropylethylamine (0.88 g, 6.80 mmol) were added. The reaction mixture was stirred overnight at room temperature, and no starting material was detected by TLC. To the reaction solution was added water (100 mL). The mixture was extracted with ethyl acetate (50 mL×3). The organic phases were combined, washed with saturated sodium chloride (50 mL×2), and dried over anhydrous sodium sulfate. The solvent was removed under reduced pressure. The crude product was purified by column chromatography (dichloromethane:methanol=50:1-20:1) to give 3a (0.90 g, yield 57%).

Synthesis of Intermediate 3b 3a (0.90 g, 1.95 mmol) was dissolved in dichloromethane (30 mL), and then trifluoroacetic acid (2 mL) was added in an ice bath. The reaction mixture was stirred overnight at room temperature, and no starting material was detected by TLC. To the reaction solution was added water (100 mL). Then the mixture was adjusted with an aqueous saturated sodium bicarbonate solution to a pH of 9-10 and extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-8:1) to give 3b (0.61 g, yield 87%).

Synthesis of Final Product 3

3b (0.61 g, 1.69 mmol) was dissolved in dichloromethane (35 mL), and then acetic anhydride (0.86 g, 8.40 mmol) and triethylamine (0.85 g, 8.40 mmol) were added. The reaction mixture was stirred at room temperature, and no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=10:1-2:1) to give the final product 3 (0.38 g, yield 56%).

MS m/z (ESI): 404.2 $[M+H]^+$.

$^1H$ NMR (600 MHz, $CDCl_3$) δ 8.88 (s, 1H), 8.29 (s, 1H), 8.10 (s, 1H), 7.28 (s, 1H), 6.77-6.72 (m, 3H), 3.82 (s, 3H), 2.52-2.49 (m, 1H), 2.24-2.22 (m, 1H), 2.00-1.95 (m, 4H), 1.98 (s, 3H), 1.48-1.38 (m, 3H), 1.18-1.13 (m, 1H).

Example 4

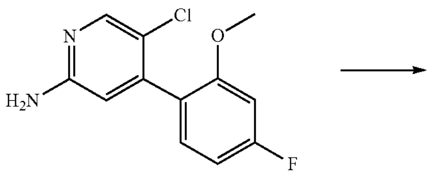

1a

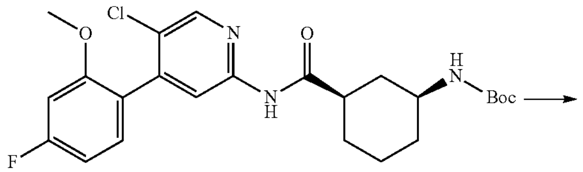

4a

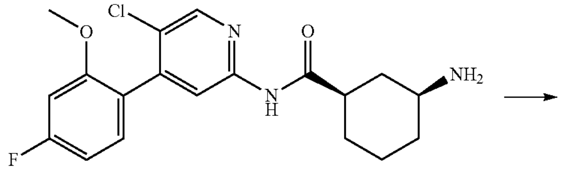

4b

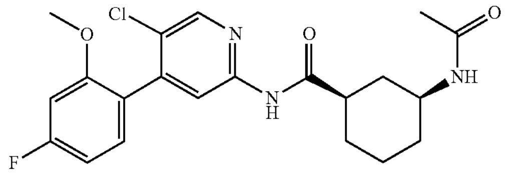

4

Synthesis of Intermediate 4a 1a (0.40 g, 1.58 mmol) was dissolved in N,N-dimethylformamide (30 mL), and then (1R,3S)-3-[(tert-butyloxycarbonyl)amino]cyclohexanecarboxylic acid (0.38 g, 1.58 mmol), 2-(7-azabenzotriazol-1-yl)-N,N,N',N'-tetramethyluronium hexafluorophosphate (0.72 g, 1.90 mmol) and N,N-diisopropylethylamine (0.41 g, 3.16 mmol) were added. The reaction mixture was stirred overnight at room temperature, and no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-20:1) to give 4a (0.45 g, yield 60%).

Synthesis of Intermediate 4b 4a (0.45 g, 0.94 mmol) was dissolved in dichloromethane (30 mL), and then trifluoroacetic acid (2 mL) was added in an ice-water bath. The reaction mixture was stirred overnight at room temperature until no starting material was detected by TLC. To the reaction solution was added water (100 mL). Then the mixture was adjusted with an aqueous saturated sodium bicarbonate solution to a pH of 9-10 and extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-8:1) to give 4b (0.30 g, yield 85%).

Synthesis of Final Product 4

4b (0.30 g, 0.80 mmol) was dissolved in dichloromethane (35 mL), and then acetic anhydride (0.24 g, 2.39 mmol) and triethylamine (0.24 g, 2.39 mmol) were added. The reaction mixture was stirred at room temperature, and no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-10:1) to give the final product 4 (0.17 g, yield 51%).

MS m/z (ESI): 420.14 $[M+H]^+$.

$^1$H NMR (600 MHz, $CDCl_3$) δ 10.69 (s, 1H), 8.41 (s, 1H), 8.05 (s, 1H), 7.78-7.73 (m, 1H), 7.27-7.22 (m, 1H), 7.10-7.08 (m, 1H), 6.91-6.88 (m, 1H), 3.76 (s, 3H), 3.57-3.54 (m, 1H), 2.62-2.59 (m, 1H), 1.86 (d, J=12.6 Hz, 1H), 1.76 (s, 6H), 1.31-1.23 (m, 3H), 1.07-1.05 (m, 1H).

Example 5

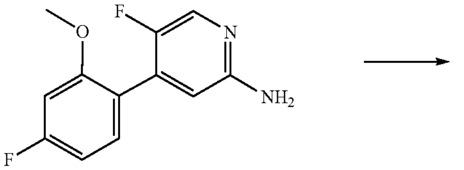

2a

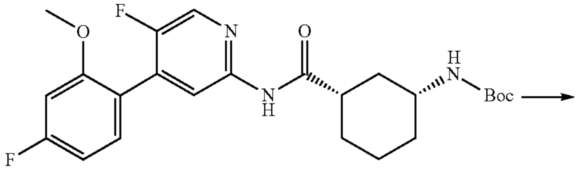

5a

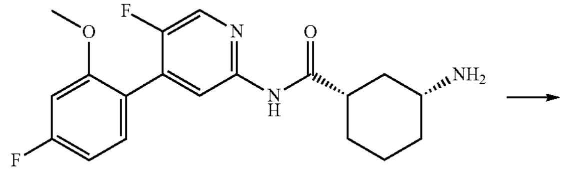

5b

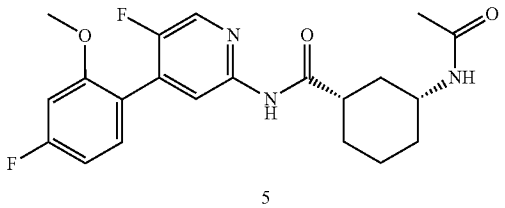

5

Synthesis of Intermediate 5a 2a (0.80 g, 3.40 mmol) was dissolved in N,N-dimethylformamide (30 mL), and then (1S,3R)-3-[(tert-butyloxycarbonyl)amino]cyclohexanecarboxylic acid (0.83 g, 3.40 mmol), 2-(7-azabenzotriazol-1-yl)-N,N,N',N'-tetramethyluronium hexafluorophosphate (1.56 g, 4.10 mmol) and N,N-diisopropylethylamine (0.88 g, 6.80 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-20:1) to give 5a (0.90 g, yield 58%).

Synthesis of Intermediate 5b 5a (0.90 g, 1.95 mmol) was dissolved in dichloromethane (30 mL), and then trifluoroacetic acid (2 mL) was added in an ice-water bath. The reaction mixture was stirred overnight at room temperature until no starting material was detected by TLC. To the reaction solution was added water (100 mL). Then the mixture was adjusted with an aqueous saturated sodium bicarbonate solution to a pH of 9-10 and extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-8:1) to give 5b (0.61 g, yield 87%).

Synthesis of Final Product 5

5b (0.61 g, 1.69 mmol) was dissolved in dichloromethane (35 mL), and then acetic anhydride (0.86 g, 8.40 mmol) and triethylamine (0.85 g, 8.40 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=10:1-2:1) to give the final product 5 (0.38 g, yield 56%).

MS m/z (ESI): 404.2 $[M+H]^+$.

$^1$H NMR (600 MHz, $CD_3OD$) δ 8.18 (s, 1H), 8.09 (s, 1H), 7.33-7.29 (m, 1H), 6.94 (d, J=10.8 Hz, 1H), 6.84-6.81 (m, 1H), 3.83 (s, 3H), 3.76-3.72 (m, 1H), 2.60-2.57 (m, 1H), 2.06 (d, J=12.0 Hz, 1H), 1.96-1.90 (m, 3H), 1.93 (s, 3H), 1.51-1.39 (m, 3H), 1.24-1.21 (m, 1H).

Example 6

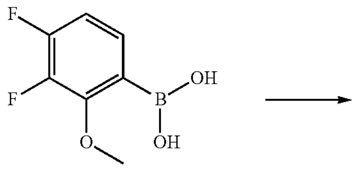

-continued

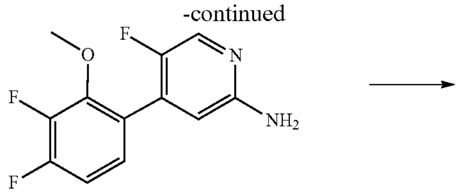

6a

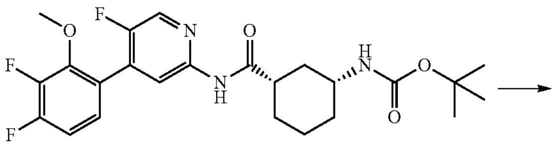

6b

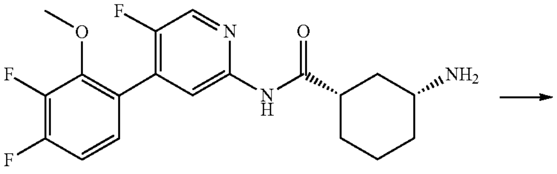

6c

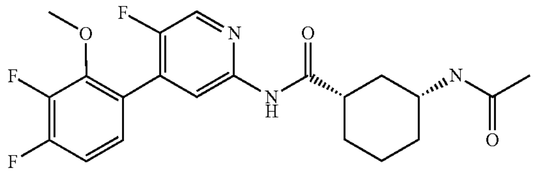

6

Synthesis of Intermediate 6a 3,4-difluoro-2-methoxyphenylboronic acid (0.57 g, 3.03 mmol) was dissolved in dioxane (50 mL), and then 5-fluoro-4-iodopyridin-2-amine (0.60 g, 2.52 mmol), tetrakis(triphenylphosphine)palladium (150 mg, 0.13 mmol) and potassium phosphate trihydrate (1.00 g, 3.78 mmol) were added. The reaction mixture was heated up to 100° C. under nitrogen gas protection and reacted for 4 hours until no starting material was detected by TLC. The reaction solution was cooled down to room temperature. The crude product was purified by column chromatography (petroleum ether: ethyl acetate=10:1-1:1) to give 6a (0.40 g, yield 52%).

Synthesis of Intermediate 6b (1S,3R)-3-[(tert-butyloxycarbonyl)amino]cyclohexanecarboxylic acid (348 mg, 1.43 mmol) was dissolved in dichloromethane (50 mL), and then pyridine (572 mg, 7.24 mmol) and thionyl chloride (300 mg, 2.52 mmol) were added. The resulting mixture was reacted at room temperature for 4 hours, and then 6a (400 mg, 1.57 mmol) was directly added to the above-mentioned reaction solution. The reaction mixture continued to react at room temperature overnight until no starting material was detected by TLC. To the reaction solution was added water (30 mL). The resulting mixture was extracted with ethyl acetate (20 mL×3). The organic phases were combined, washed with saturated sodium chloride solution (20 mL×2), and dried over anhydrous sodium sulfate. The solvent was removed under reduced pressure. The crude product was purified by column chromatography (petroleum ether:ethyl acetate=10:1-2:1) to give 6b (250 mg, yield 33%).

Synthesis of Intermediate 6c 6b (250 mg, 0.52 mmol) was dissolved in dichloromethane (10 mL), and then trifluoroacetic acid (1 mL) was added. The resulting mixture was reacted at room temperature for 1.5 hours until no starting material was detected by TLC. To the reaction solution was added saturated sodium bicarbonate solution (30 mL). The mixture was extracted with dichloromethane (20 mL×3). The organic phases were combined, washed with saturated sodium chloride solution (20 mL×2), and dried over anhydrous sodium sulfate. The solvent was removed under reduced pressure to give 6c (130 mg, yield 65%).

Synthesis of Final Product 6

6c (130 mg, 0.34 mmol) was dissolved in dichloromethane (10 mL), and then acetic anhydride (45 mg, 0.44 mmol) and triethylamine (44 mg, 0.44 mmol) were added. The reaction mixture was reacted at room temperature for 1.5 hours until no starting material was detected by TLC. To the reaction solution was added saturated sodium bicarbonate solution (30 mL). The mixture was extracted with dichloromethane (20 mL×3). The organic phases were combined, washed with saturated sodium chloride solution (20 mL×2), and dried over anhydrous sodium sulfate. The solvent was removed under reduced pressure. The crude product was purified by column chromatography (dichloromethane: methanol=50:1-30:1) to give the final product 6 (120 mg, yield 84%).

MS m/z (ESI): 422.2 $[M+H]^+$.

$^1$H NMR (600 MHz, DMSO-d6) δ 10.68 (s, 1H), 8.43 (s, 1H), 8.20 (s, 1H), 7.78 (d, J=7.8 Hz, 1H), 7.33 (t, J=7.8 Hz, 1H), 7.21 (t, J=7.8 Hz, 1H), 3.95 (s, 3H), 3.59-3.54 (m, 1H), 2.63-2.59 (m, 1H), 1.88-1.84 (m, 1H), 1.80-1.72 (m, 3H), 1.78 (s, 3H), 1.31-1.25 (m, 3H), 1.10-1.04 (m, 1H).

Example 7

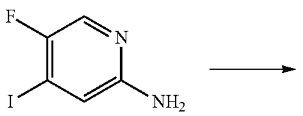

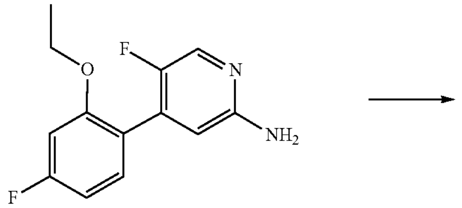

7a

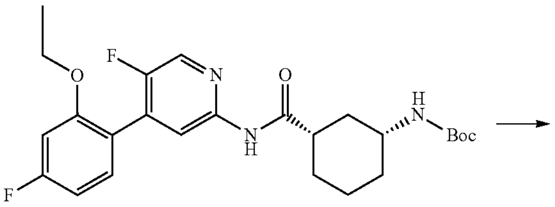

7b

-continued

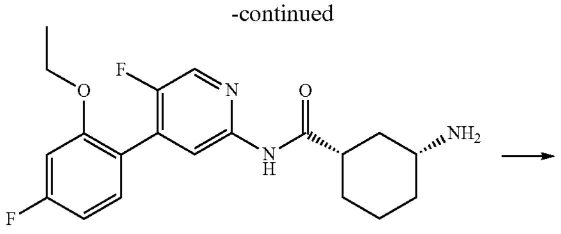

7c

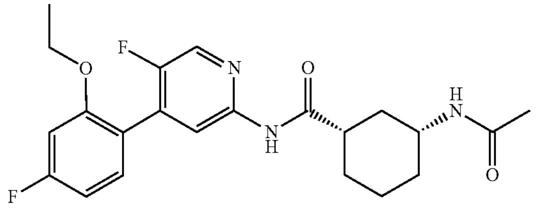

7

Synthesis of Intermediate 7a 2-amino-5-fluoro-4-iodopyridine (0.50 g, 2.10 mmol) and 5-fluoro-2-ethoxyphenylboronic acid (0.46 g, 2.50 mmol) were dissolved in ethylene glycol dimethyl ether (10 mL) and water (2 mL), and then [1,1'-bis(diphenylphosphino) ferrocene]dichloropalladium (71 mg, 0.10 mmol) and potassium carbonate (0.87 g, 6.30 mmol) were added. The mixture was evacuated and backfilled with $N_2$ (3 times). The reaction mixture was reacted at 100° C. for 2 hours. Until no starting material was detected by TLC, the mixture was cooled and then the solvent was removed by concentration. The crude product was purified by column chromatography (petroleum ether:ethyl acetate=10:1-2:1) to give 7a (0.50 g, yield 95%).

Synthesis of Intermediate 7b

The compound (1S,3R)-3-[(tert-butyloxycarbonyl) amino]cyclohexanecarboxylic acid (0.29 g, 1.20 mmol) was dissolved in dichloromethane (10 mL), and pyridine (395 mg, 5.00 mmol) and thionyl chloride (202 mg, 1.70 mmol) were added in an ice bath. The reaction mixture was reacted at room temperature for 2 hours and concentrated to remove the solvent and the redundant thionyl chloride. Then dichloromethane (10 mL) and the compound 7a (250 mg, 1.00 mmol) were added. The reaction mixture was reacted at room temperature overnight until no starting material was detected by TLC. The mixture was concentrated. The crude product was purified by column chromatography (petroleum ether:ethyl acetate=10:1-1:1) to give 7b (100 mg, yield 21%).

Synthesis of Intermediate 7c 7b (47 mg, 0.10 mmol) was dissolved in dichloromethane (5 mL), and trifluoroacetic acid (2 mL) was added. The reaction mixture was reacted at room temperature for 1 hour until no starting material was detected by TLC. The mixture was concentrated to give 7c (50 mg, crude product). The product was not further purified and directly used in the next step reaction.

Synthesis of Final Product 7

7c (37 mg, 0.10 mmol) was dissolved in dichloromethane (2 mL), triethylamine (20 mg, 0.20 mmol) and acetic anhydride (20 mg, 0.20 mmol) were added. The reaction mixture was reacted at room temperature for 1 hour until no starting material was detected by TLC. The mixture was concentrated. The resulting crude product was purified by thin-layer chromatography (dichloromethane:methanol=10:1) to give the final product 7 (30 mg, yield 72%).

MS:(m/z, ESI): 417.2 $[M+H]^+$.

$^1H$ NMR (600 MHz, DMSO-d6) δ 10.57 (s, 1H), 8.33 (s, 1H), 8.11 (d, J=5.4 Hz, 1H), 7.79 (d, J=7.8 Hz, 1H), 7.35 (d, J=7.8 Hz, 1H), 7.09 (d, J=11.4 Hz, 1H), 6.90 (d, J=7.8 Hz, 1H), 4.10-4.07 (m, 2H), 3.57-3.55 (m, 1H), 2.59-2.57 (m, 1H), 1.87-1.84 (m, 1H), 1.77-1.75 (m, 5H), 1.70-1.50 (m, 1H), 1.31-1.26 (m, 3H), 1.24-1.21 (m, 3H), 1.07-1.05 (m, 1H).

Example 8

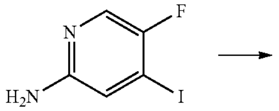

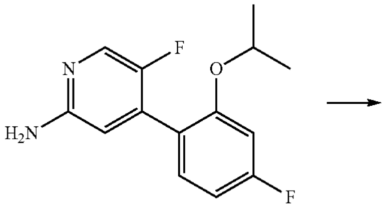

8a

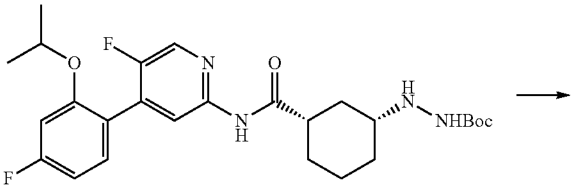

8b

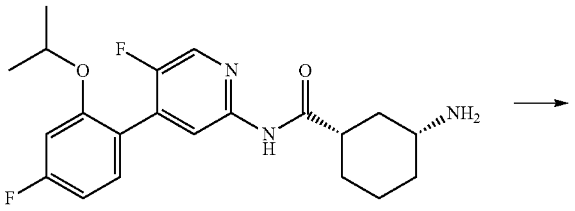

8c

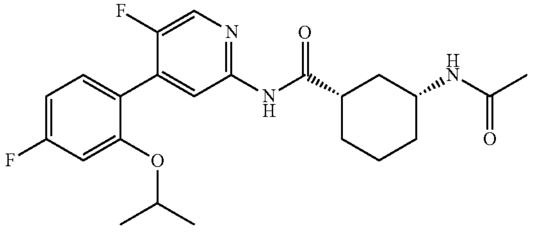

8

Synthesis of Intermediate 8a 5-fluoro-4-iodopyridin-2-amine (1.00 g, 4.20 mmol) was dissolved in ethylene glycol dimethyl ether (20 mL) and water (4 mL), and then 4-fluoro-2-isopropoxyphenylboronic acid (0.83 g, 4.20 mmol), [1,1'-bis(diphenylphosphino)ferrocene]dichloropalladium (0.31 g, 0.42 mmol) and potassium carbonate (1.74 g, 12.60 mmol) were added. The mixture was evacuated and backfilled with $N_2$ (3 times). The reaction mixture was stirred under reflux at 100° C. and reacted for 4 hours until no starting material was detected by TLC. The mixture was concentrated under reduced pressure. The crude product was purified by column chromatography (dichloromethane:methanol=50:1-10:1) to give 8a (0.85 g, yield 77%).

Synthesis of Intermediate 8b 8a (0.85 g, 3.20 mmol) was dissolved in N,N-dimethylformamide (30 mL), and then (1S,3R)-3-[(tert-butyloxycarbonyl)amino]cyclohexanecarboxylic acid (0.78 g, 3.20 mmol), 2-(7-azabenzotriazol-1-yl)-N,N,N',N'-tetramethyluronium hexafluorophosphate (1.44 g, 3.80 mmol) and N,N-diisopropylethylamine (0.83 g, 6.40 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-20:1) to give 8b (0.90 g, yield 57%).

Synthesis of Intermediate 8c 8b (0.90 g, 1.84 mmol) was dissolved in dichloromethane (30 mL), and then trifluoroacetic acid (2 mL) was added in an ice-water bath. The reaction mixture was stirred overnight at room temperature until no starting material was detected by TLC. To the reaction solution was added water (100 mL). Then the mixture was adjusted with an aqueous saturated sodium bicarbonate solution to a pH of 9-10 and extracted with dichloromethane (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-8:1) to give 8c (0.64 g, yield 89%).

Synthesis of Final Product 8

8c (0.64 g, 1.64 mmol) was dissolved in dichloromethane (35 mL), and then acetic anhydride (0.84 g, 8.20 mmol) and triethylamine (0.83 g, 8.20 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=10:1-2:1) to give the final product 8 (0.42 g, yield 59%).

MS:(m/z, ESI): 431.2 $[M+H]^+$.

$^1$H NMR (600 MHz, DMSO-$d_6$) δ 10.57 (s, 1H), 8.32 (s, 1H), 8.12 (s, 1H), 7.78 (d, J=7.8 Hz, 1H), 7.34 (d, J=7.2 Hz, 1H), 7.10 (s, 1H), 6.88 (d, J=8.4 Hz, 1H), 4.72-4.69 (m, 1H), 3.56 (s, 1H), 2.62-2.58 (m, 1H), 1.78 (s, 6H), 1.31-1.23 (m, 4H), 1.20 (s, 6H), 1.09-1.04 (m, 1H).

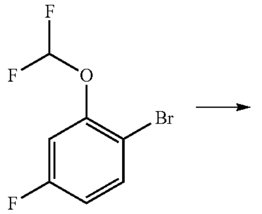

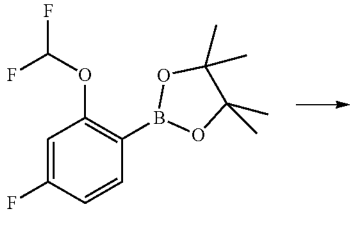

9a

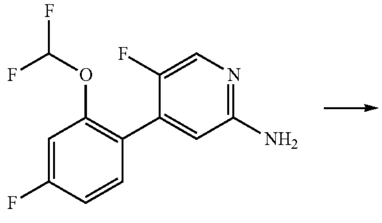

9b

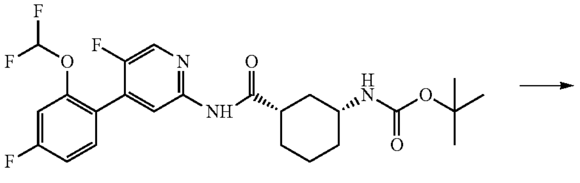

9c

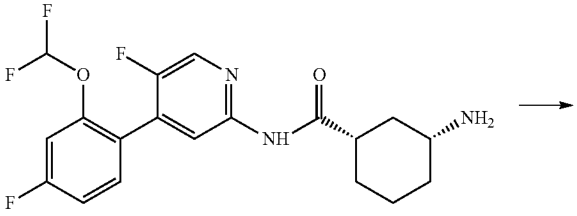

9d

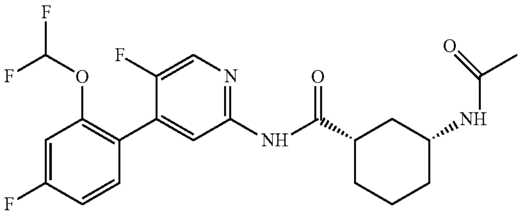

9

Synthesis of Intermediate 9a 1-bromo-2-difluoromethoxy-4-fluorobenzene (1.00 g, 4.15 mmol), bis(pinacolato)diboron (1.26 g, 4.98 mmol), potassium acetate (1.22 g, 12.45 mmol), [1,1'-bis(diphenylphosphino)ferrocene]dichloropalladium (0.24 g, 0.33 mmol), and ethylene glycol dimethyl ether (30 mL) were added to the reactor. The reaction mixture was heated to 100° C. under nitrogen gas protection and reacted for 8 hours until no starting material was detected by TLC. The reaction mixture was cooled to room temperature. The mixture was concentrated under reduced pressure, and the crude product was purified by column chromatography (n-hexane:ethyl acetate=10:1) to give 9a (0.50 g, yield 42%).

Synthesis of Intermediate 9b 9a (0.50 g, 1.74 mmol), 5-fluoro-4-iodo-pyridine-2-amine (0.33 g, 1.39 mmol), tetrakis(triphenylphosphine)palladium (0.12 g, 0.10 mmol), tripotassium phosphate trihydrate (0.60 g, 2.26 mmol), and dioxane (30 mL) were added to the reactor. The reaction mixture was heated to 100° C. under nitrogen gas protection and reacted for 8 hours until no starting material was detected by TLC. The heating was stopped, and the reaction mixture was cooled to room temperature. The mixture was concentrated under reduced pressure, and the crude product was purified by column chromatography (n-hexane:ethyl acetate=1:1) to give 9b (0.39 g, yield 83%).

Synthesis of Intermediate 9c 9b (0.39 g, 1.43 mmol), (1S,3R)-3-[(tert-butyloxycarbonyl)amino]cyclohexanecarboxylic acid (0.35 g, 1.43 mmol), 2-(7-azabenzotriazol-1-yl)-N,N,N',N'-tetramethyluronium hexafluorophosphate (0.65 g, 1.72 mmol), N,N-diisopropylethylamine (0.37 g, 2.86 mmol) and N,N-dimethylformamide (20 mL) were added into the reactor. The reaction mixture was reacted at room temperature for 15 hours until no starting material was detected by TLC. To the reaction solution was added water (30 mL). The mixture was extracted with ethyl acetate (30 mL×3). The organic phases were combined, washed with saturated sodium chloride solution (30 mL×2), and dried over anhydrous sodium sulfate. The solvent was removed under reduced pressure. The crude product was purified by column chromatography (n-hexane:ethyl acetate=1:1) to give 9c (0.16 g, yield 23%).

Synthesis of Intermediate 9d 9c (0.16 g, 0.33 mmol) was dissolved in dichloromethane (20 mL), and then trifluoroacetic acid (4 mL) was added. The reaction mixture was reacted at room temperature for 4 hours until no starting material was detected by TLC. The reaction solution was washed with water (20 mL×3), and the aqueous phases were combined. The combined aqueous phase was adjusted with sodium carbonate to a pH of 8-9 and extracted with dichloromethane (30 mL×3). The organic phases were combined and dried over anhydrous sodium sulfate. The solvent was removed under reduced pressure to give 9d (0.10 g, yield 76%).

Synthesis of Final Product 9

9d (0.10 g, 0.26 mmol) was dissolved in dichloromethane (20 mL), and acetic anhydride (0.05 g, 0.52 mmol) and triethylamine (0.05 g, 0.52 mmol) were added. The reaction mixture was reacted at room temperature for 2 hours until no starting material was detected by TLC. The reaction solution was directly purified by column chromatography (dichloromethane:methanol=25:1) to give the final product 9 (0.05 g, yield 44%).

MS m/z (ESI):440.2 $[M+H]^+$.

$^1H$ NMR (600 MHz, DMSO-$d_6$) δ 10.67 (s, 1H), 8.41 (s, 1H), 8.12 (d, J=5.4 Hz, 1H), 7.78 (d, J=7.2 Hz, 1H), 7.58-7.56 (m, 1H), 7.42 (s, 1H), 7.34-7.28 (m, 1H), 3.57-3.56 (m, 1H), 2.61-2.59 (m, 1H), 1.89-1.78 (m, 4H), 1.77 (s, 3H), 1.31-1.24 (m, 3H), 1.08-1.06 (m, 1H).

Example 10

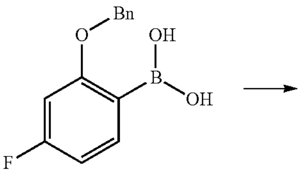

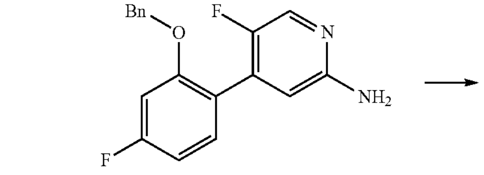

10a

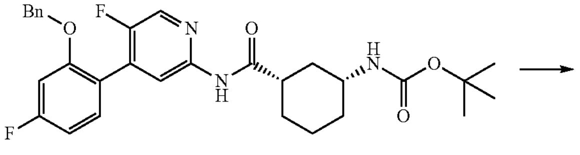

10b

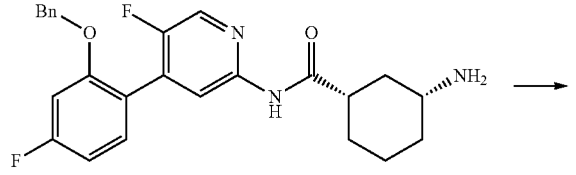

10c

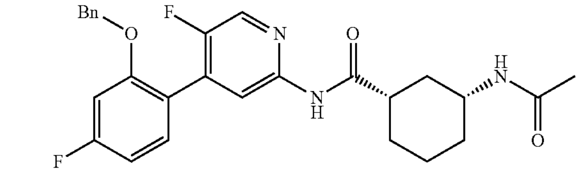

10

Synthesis of Intermediate 10a 5-fluoro-4-iodopyridin-2-amine (500 mg, 2.10 mmol) was dissolved in a mixed solvent of DME (20 mL) and water (4 mL), and then 2-benzyloxy-4-fluorophenylboronic acid (620 mg, 2.52 mmol), [1,1'-bis(diphenylphosphino)ferrocene]dichloropalladium dichloromethane complex (90 mg, 0.11 mmol) and potassium carbonate (870 mg, 6.30 mmol) were added. The mixture was evacuated and backfilled with $N_2$ (3 times). The reaction mixture was stirred and brought to reflux at 100° C. and reacted for 4 hours until the starting material was completely converted, as monitored by TLC. The reaction solution was directly purified by column chromatography (petroleum ether:ethyl acetate=5:1-2:1) to give 10a (0.50 g, yield 76%).

Synthesis of Intermediate 10b 10a (0.30 g, 0.96 mmol) was dissolved in N,N-dimethylformamide (30 mL), and then (1S,3R)-3-[(tert-butyloxycarbonyl)amino]cyclohexanecarboxylic acid (0.25 g, 1.01 mmol), 2-(7-azabenzotriazol-1-yl)-N,N,N',N'-tetramethyluronium hexafluorophosphate (0.43 g, 1.15 mmol) and N,N-diisopropylethylamine (0.25 g, 1.92 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=10:1-2:1) to give 10b (0.30 g, yield 58%).

Synthesis of Intermediate 10c 10b (0.30 g, 0.56 mmol) was dissolved in dichloromethane (30 mL), and then trifluoroacetic acid (2 mL) was added in an ice-water bath. The reaction mixture was stirred at room temperature for 2 hours until no starting material was detected by TLC. To the reaction solution was added water (100 mL). Then the mixture was adjusted with an aqueous saturated sodium bicarbonate solution to a pH of 9-10. The mixture was extracted with dichloromethane (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-8:1) to give 10c (0.20 g, yield 82%).

Synthesis of Final Product 10

10c (0.20 g, 0.46 mmol) was dissolved in dichloromethane (10 mL), and then acetic anhydride (94 mg, 0.92 mmol) and triethylamine (93 mg, 0.92 mmol) were added. The reaction mixture was reacted at room temperature for 1.5 hours, and the starting material was completely converted, as monitored by TLC (ethyl acetate). To the reaction solution was added saturated sodium bicarbonate solution (30 mL). The mixture was extracted with dichloromethane (20 mL×3). The organic phases were combined, washed with saturated sodium chloride solution (20 mL×2), and dried over anhydrous sodium sulfate. The solvent was removed under reduced pressure. The crude product was purified by column chromatography (dichloromethane:methanol=50:1-20:1) to give the final product 10 (150 mg, yield 68%).

MS m/z (ESI): 480.2 $[M+H]^+$.

$^1H$ NMR (600 MHz, DMSO-$d_6$) δ 10.56 (s, 1H), 8.32 (s, 1H), 8.14 (d, J=5.4 Hz, 1H), 7.76 (d, J=7.8 Hz, 1H), 7.37 (dd, J=7.8 Hz, J=7.2 Hz, 1H), 7.32-7.27 (m, 5H), 7.16 (d, J=11.4 Hz, 1H), 6.92 (dd, J=8.4 Hz, J=8.4 Hz, 1H), 5.15 (s, 2H), 3.55-3.54 (m, 1H), 2.58-2.56 (m, 1H), 1.86-1.84 (m, 1H), 1.75-1.70 (m, 6H), 1.33-1.15 (m, 4H).

Example 11

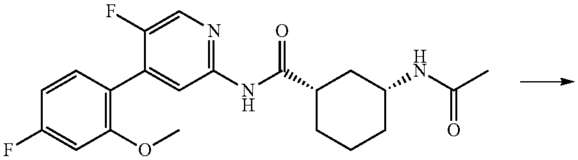

-continued

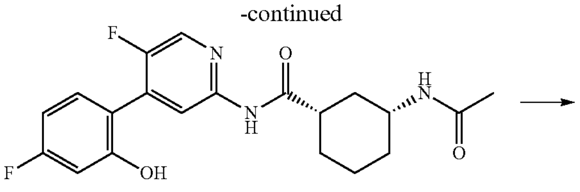

11a

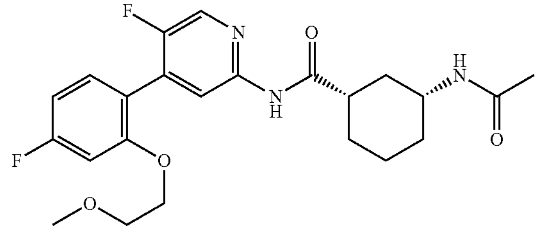

11

Synthesis of Intermediate 11a 5 (0.10 g, 0.25 mmol) was dissolved in dichloromethane (20 mL), and boron tribromide (0.12 g, 0.50 mmol) was added. The reaction mixture was reacted at room temperature for 4 hours until no starting material was detected by TLC. The reaction solution was adjusted with an aqueous sodium bicarbonate solution to a pH of about 6, and the organic phase was dried over anhydrous sodium sulfate. The solvent was removed under reduced pressure to give 11a (0.08 g, yield 82%).

Synthesis of Final Product 11

11a (0.08 g, 0.21 mmol) was dissolved in N,N-dimethylformamide (10 mL), and 2-bromoethyl methyl ether (0.03 g, 0.25 mmol) and potassium carbonate (0.06 g, 0.42 mmol) were added. The reaction mixture was reacted at room temperature for 8 hours and no starting material was detected by TLC. To the reaction solution was added water (20 mL). The mixture was extracted with ethyl acetate (20 mL×3). The organic phases were combined and dried over anhydrous sodium sulfate. The organic phases were purified by column chromatography (dichloromethane:methanol=25:1) to give the final product 11 (0.05 g, yield 53%).

MS m/z (ESI): 448.2 $[M+H]^+$.

$^1H$ NMR (600 MHz, DMSO-$d_6$) δ 10.56 (s, 1H), 8.31 (s, 1H), 8.11-8.10 (m, 1H), 7.78-7.58 (m, 1H), 7.36-7.33 (m, 1H), 7.12-7.01 (m, 1H), 6.92-6.89 (m, 1H), 4.15-4.13 (m, 2H), 3.55-3.54 (m, 2H), 3.53-3.52 (m, 1H), 3.15 (s, 3H), 2.59-2.58 (m, 1H), 1.85 (s, 3H), 1.83-1.47 (m, 4H), 1.29-1.04 (m, 4H).

Example 12

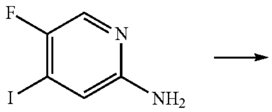

-continued

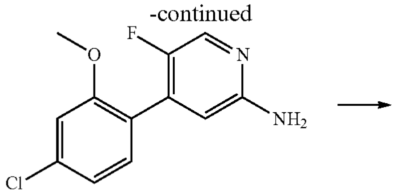

12a

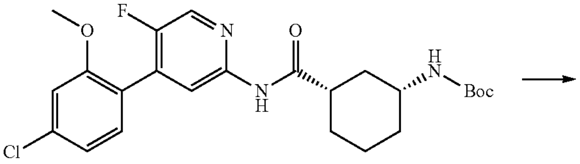

12b

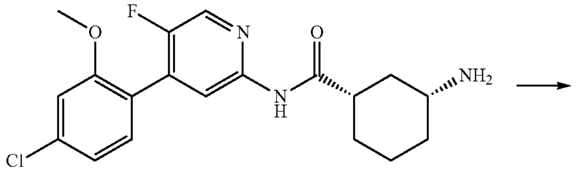

12c

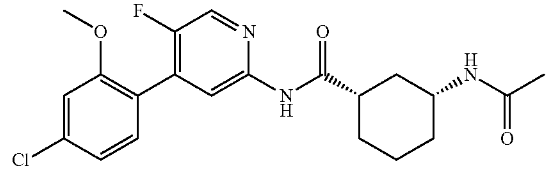

12

Synthesis of Intermediate 12a 2-amino-5-fluoro-4-iodopyridine (0.50 g, 2.10 mmol) and 5-chloro-2-methoxyphenylboronic acid (0.47 g, 2.50 mmol) were dissolved in ethylene glycol dimethyl ether (10 mL), and [1,1-bis(diphenylphosphino)ferrocene]dichloropalladium (73 mg, 0.10 mmol), potassium carbonate (0.87 g, 6.3 mmol) and water (2 mL) were added. The mixture was evacuated and backfilled with $N_2$ (3 times). The reaction mixture was reacted at 100° C. for 2 hours until no starting material was detected by TLC. The mixture was cooled and then concentrated to remove the solvent. The crude product was purified by column chromatography (petroleum ether: ethyl acetate=10:1-2:1) to give 12a (0.50 g, yield 95%).

Synthesis of Intermediate 12b (1S,3R)-3-[(tert-butyloxycarbonyl)amino]cyclohexanecarboxylic acid (0.29 g, 1.20 mmol) was dissolved in dichloromethane (10 mL), and pyridine (0.40 g, 5.00 mmol) and thionyl chloride (0.20 g, 1.70 mmol) were added in an ice bath. The reaction mixture was reacted at room temperature for 2 hours and concentrated. Then dichloromethane (10 mL) and the compound 12a (0.25 g, 1.00 mmol) were added. The reaction mixture was reacted at room temperature overnight. After no starting material was detected by TLC, the reaction mixture was concentrated. The crude product was purified by column chromatography (petroleum ether: ethyl acetate=10:1-1:1) to give 12b (0.10 g, yield 21%).

Synthesis of Intermediate 12c 12b (48 mg, 0.10 mmol) was dissolved in dichloromethane (5 mL), and trifluoroacetic acid (2 mL) was added. The reaction was conducted at room temperature for 1 hour until no starting material was detected by TLC. The mixture was concentrated to give 12c (50 mg, crude product). The product was not further purified and directly used in the next step reaction.

Synthesis of final product 12

12c (50 mg, 0.10 mmol) was dissolved in dichloromethane (2 mL), and triethylamine (20 mg, 0.20 mmol) and acetic anhydride (20 mg, 0.20 mmol) were added. The reaction mixture was conducted at room temperature for 1 hour until no starting material was detected by TLC. The reaction mixture was concentrated. The resulting crude product was purified by thin-layer chromatography (dichloromethane:methanol=10:1) to give the final product 12 (30 mg, yield 72%).

MS:(m/z, ESI): 420.1 $[M+H]^+$.

$^1H$ NMR (600 MHz, DMSO-$d_6$) δ 10.60 (s, 1H), 8.34 (s, 1H), 8.08 (d, J=5.4 Hz, 1H), 7.78 (d, J=7.8 Hz, 1H), 7.33 (d, J=8.4 Hz, 1H), 7.27 (s, 1H), 7.20-7.15 (m, 1H), 3.80 (s, 3H), 3.65-3.55 (m, 1H), 2.68-2.62 (m, 1H), 1.90-1.85 (m, 1H), 1.76-1.55 (m, 6H), 1.28-1.23 (m, 3H), 1.15-1.10 (m, 1H).

Example 13

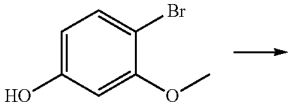

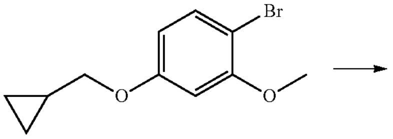

13a

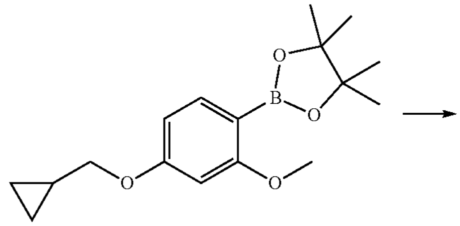

13b

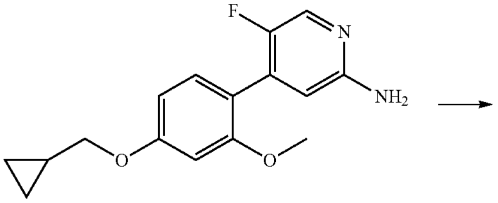

13c

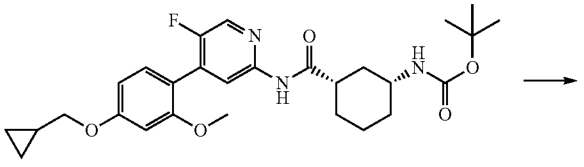

13d

-continued

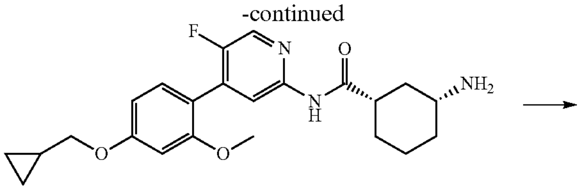

13e

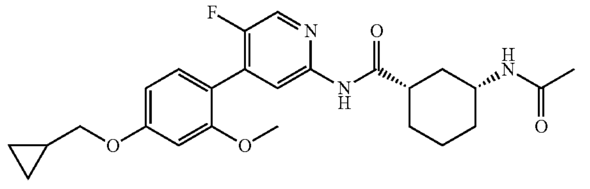

13

Synthesis of Intermediate 13a 3-methoxy-4-bromophenol (3.00 g, 14.80 mmol) was dissolved in acetone (50 mL), and then bromomethylcyclopropane (2.20 g, 16.30 mmol), sodium iodide (1.11 g, 7.40 mmol), and cesium carbonate (9.64 g, 29.60 mmol) were added. The reaction mixture was stirred under a reflux condition and reacted for 8 hours until no starting material was detected by TLC. The reaction mixture was cooled to room temperature. Acetone was removed under reduced pressure. To the residue was added water (50 mL). The mixture was extracted with ethyl acetate (30 mL×3). The organic phases were combined, washed with saturated sodium chloride solution (50 mL×2), and dried over anhydrous sodium sulfate. The solvent was removed under reduced pressure to give 13a (3.70 g, yield 97%).

Synthesis of Intermediate 13b 13a (3.20 g, 12.40 mmol) was dissolved in ethylene glycol dimethyl ether (50 mL), and then bis(pinacolato)diboron (3.79 g, 14.90 mmol), potassium acetate (3.65 g, 37.2 mmol) and [1,1'-bis(diphenylphosphino)ferrocene]dichloropalladium (0.88 g, 1.2 mmol) were added. The reaction mixture was heated to 100° C. under nitrogen gas protection and reacted for 8 hours, and no starting material was detected by TLC. The heating was stopped, and the mixture was cooled to room temperature. The solvent was removed under reduced pressure. The crude product was purified by column chromatography (n-hexane:ethyl acetate=5:1) to give 13b (2.50 g, yield 66%).

Synthesis of Intermediate 13c 13b (2.19 g, 7.20 mmol) was dissolved in dioxane (50 mL), and then 5-fluoro-4-iodo-pyridine-2-amine (1.38 g, 5.80 mmol), tetrakis(triphenylphosphine)palladium (0.46 g, 0.40 mmol) and potassium phosphate trihydrate (2.50 g, 9.40 mmol) were added. The reaction mixture was heated to 100° C. under nitrogen gas protection and reacted for 8 hours until no starting material was detected by TLC. The heating was stopped, and the reaction mixture was cooled to room temperature. The solvent was removed under reduced pressure. The crude product was purified by column chromatography (n-hexane:ethyl acetate=1:1) to give 13c (1.90 g, yield 92%).

Synthesis of Intermediate 13d 13c (0.60 g, 2.10 mmol) was dissolved in N,N-dimethylformamide (20 mL), and then (1S,3R)-3-[(tert-butyloxycarbonyl)amino]cyclohexanecarboxylic acid (0.51 g, 2.10 mmol), 2-(7-azabenzotriazol-1-yl)-N,N,N',N'-tetramethyluronium hexafluorophosphate (0.95 g, 2.50 mmol) and N,N-diisopropylethylamine (0.54 g, 4.20 mmol) were added. The reaction mixture was reacted at room temperature for 15 hours until no starting material was detected by TLC. To the reaction solution was added water (50 mL). The mixture was extracted with ethyl acetate (30 mL×3). The organic phases were combined, washed with saturated sodium chloride solution (50 mL×2), and dried over anhydrous sodium sulfate. The solvent was removed under reduced pressure. The crude product was purified by column chromatography (n-hexane:ethyl acetate=1:1) to give 13d (0.50 g, yield 46%).

Synthesis of Intermediate 13e 13d (0.50 g, 0.97 mmol) was dissolved in dichloromethane (20 mL), and trifluoroacetic acid (4 mL) was added. The reaction mixture was reacted at room temperature for 4 hours until no starting material was detected by TLC. The reaction solution was washed with water (30 mL×3), and the aqueous phases were combined. The combined aqueous phase was adjusted with sodium carbonate to a pH of 8-9 and extracted with dichloromethane (30 mL×3). The organic phases were combined, washed with saturated sodium chloride solution (50 mL×2), and dried over anhydrous sodium sulfate. The solvent was removed under reduced pressure to give 13e (0.35 g, yield 88%).

Synthesis of Final Product 13

13e (0.06 g, 0.14 mmol) was dissolved in dichloromethane (20 mL), and then acetic anhydride (0.03 g, 0.28 mmol) and triethylamine (0.03 g, 0.28 mmol) were added. The reaction mixture was reacted at room temperature for 2 hours until no starting material was detected by TLC. The reaction solution was directly purified by column chromatography (DCM:MeOH=25:1) to give the final product 13 (0.02 g, yield 31%).

MS m/z (ESI): 456.2 $[M+H]^+$.

$^1H$ NMR (600 MHz, DMSO-$d_6$) δ 10.52 (s, 1H), 8.28 (s, 1H), 8.06 (d, J=4.8 Hz, 1H), 7.78 (d, J=7.8 Hz, 1H), 7.18 (d, J=8.4 Hz, 1H), 6.71 (s, 1H), 6.63 (d, J=8.4 Hz, 1H), 3.89 (d, J=7.2 Hz, 2H), 3.76 (s, 3H), 3.57-3.55 (m, 1H), 2.61-2.60 (m, 1H), 1.88-1.86 (m, 1H), 1.77 (s, 3H), 1.76-1.75 (m, 3H), 1.31-1.23 (m, 4H), 1.09-1.04 (m, 1H), 0.60-0.59 (m, 2H), 0.35-0.34 (m, 2H).

Example 14

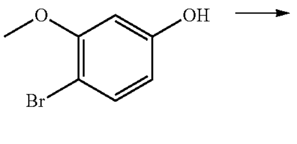

-continued

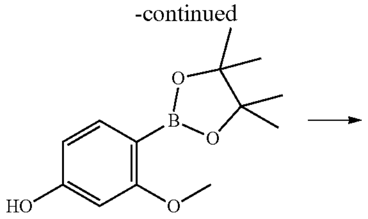

14a

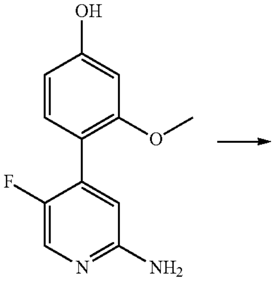

14b

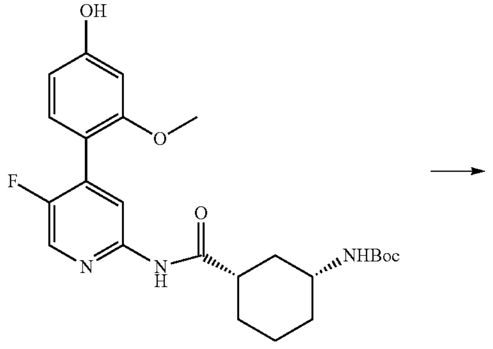

14c

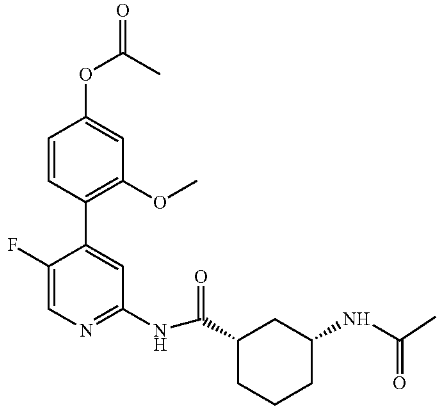

14

Synthesis of Intermediate 14a 4-bromo-3-methoxyphenol (0.40 g, 2.00 mmol) was dissolved in dioxane (50 mL), and then bis(pinacolato)diboron (0.60 g, 2.40 mmol), [1,1'-bis(diphenylphosphino)ferrocene] dichloropalladium (0.12 g, 0.16 mmol) and potassium acetate (0.59 g, 6.00 mmol) were added. The reaction mixture was stirred and reacted for 5 hours at 100° C. under nitrogen gas protection, and the starting material was completely converted, as monitored by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether-petroleum ether:ethyl acetate=4:1) to give 14a (0.36 g, yield 72%).

Synthesis of Intermediate 14b 14a (0.36 g, 1.44 mmol) was dissolved in diethylene glycol dimethyl ether (50 mL) and water (10 mL), and then 5-fluoro-4-iodo-pyridine-2-amine (0.29 g, 1.20 mmol), [1,1'-bis(diphenylphosphino)ferrocene]dichloropalladium (0.44 g, 0.60 mmol) and potassium carbonate (0.50 g, 3.60 mmol) were added. The reaction mixture was stirred at 80° C. for 5 hours until no starting material was detected by TLC. To the reaction solution was added water (100 mL). The mixture was extracted with ethyl acetate (100 mL×3). The organic phases were combined, washed with saturated sodium chloride solution (100 mL×2), and dried over anhydrous sodium sulfate. The solvent was removed under reduced pressure. The crude product was purified by column chromatography (petroleum ether:ethyl acetate=4:1-2:3) to give 14b (0.25 g, yield 74%).

Synthesis of Intermediate 14c 14b (0.15 g, 0.64 mmol) was dissolved in N,N-dimethylformamide (50 mL), and then (1S,3R)-3-[(tert-butyloxycarbonyl)amino]cyclohexanecarboxylic acid (0.18 g, 0.72 mmol), 2-(7-azabenzotriazol-1-yl)-N,N,N',N'-tetramethyluronium hexafluorophosphate (0.58 g, 0.72 mmol) and diisopropylethylamine (0.20 mL, 1.20 mmol) were added. The reaction mixture was stirred and reacted at 25° C. for 15 hours until no starting material was detected by TLC. To the reaction solution was added water (100 mL). The mixture was extracted with ethyl acetate (100 mL×3). The organic phases were combined, washed with saturated sodium chloride solution (100 mL×2), and dried over anhydrous sodium sulfate. The solvent was removed under reduced pressure. The crude product was purified by column chromatography (petroleum ether:ethyl acetate=4:1-2:1) to give 14c (0.15 g, yield 51%).

Synthesis of Final Product 14

14c (0.15 g, 0.32 mmol) was dissolved in dichloromethane (50 mL), and then trifluoroacetic acid (2 mL) was added. The mixture was stirred at room temperature for 4 hours until no starting material was detected by TLC. To the mixture was added an aqueous saturated sodium carbonate solution. The pH value of the reaction mixture was adjusted to 9-10. The reaction mixture was extracted with dichloromethane (50 mL×3). The organic phases were combined and concentrated to a volume of about 50 mL. Triethylamine (2 mL) and acetic anhydride (2 mL) were added. The mixture was reacted at room temperature for 30 minutes. An aqueous sodium carbonate solution was added to wash the organic phase. The aqueous phase was separated and then extracted with dichloromethane (50 mL×3). The organic phases were combined and concentrated under reduced pressure. The resulting crude product was purified by column chromatography (ethyl acetate) to give the final product 14 (90 mg, yield 63%).

MS m/z (ESI): 444.2 $[M+H]^+$.

$^1$H NMR (600 MHz, $CD_3OD$) δ 8.16 (s, 1H), 8.10 (s, 1H), 7.29 (d, J=7.8 Hz, 1H), 6.87 (s, 1H), 6.78 (t, J=7.8 Hz, 1H), 3.79 (s, 3H), 3.78-3.73 (m, 1H), 2.72 (t, J=12.0 Hz, 1H), 2.31-2.29 (m, 1H), 2.20-2.10 (m, 1H), 2.00-1.80 (m, 6H), 1.51-1.38 (m, 3H), 1.27-1.21 (m, 2H).

Example 15

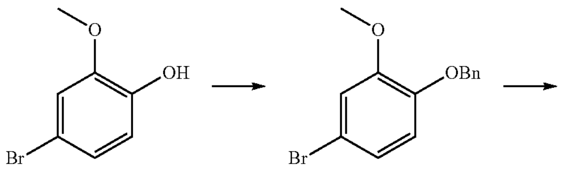

15a

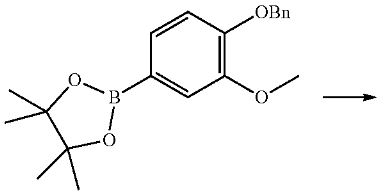

15b

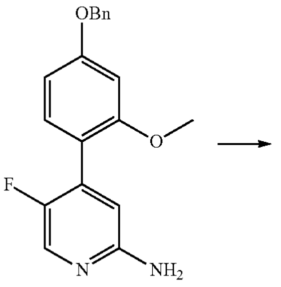

15c

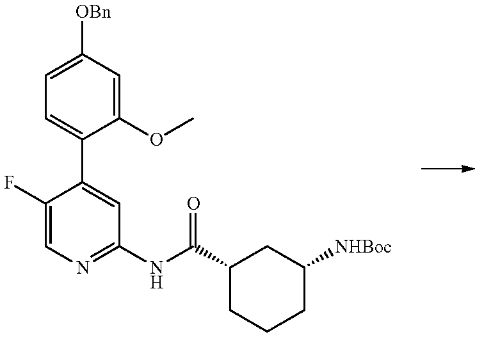

15d

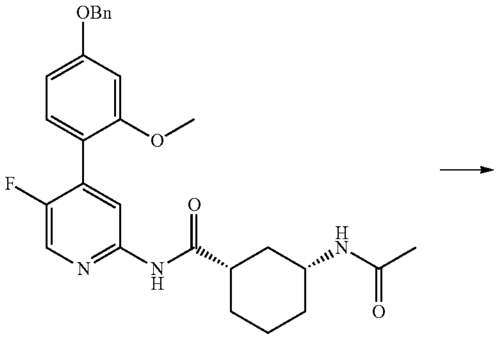

15e

-continued

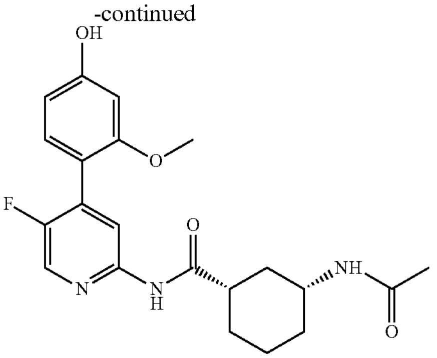

15

Synthesis of Intermediate 15a 3-methoxy-4-bromophenol (540 mg, 2.66 mmol) was dissolved in N,N-dimethylformamide (50 mL), and then potassium carbonate (735 mg, 5.32 mmol) and benzyl bromide (910 mg, 5.32 mmol) were added. The reaction mixture was stirred and reacted at room temperature for 15 hours until no starting material was detected by TLC. To the reaction mixture was added water (50 mL). The mixture was extracted with ethyl acetate (50 mL×3). The organic phases were combined, washed with an aqueous saturated sodium chloride solution (50 mL×2), and dried over anhydrous sodium sulfate. The mixture was concentrated under reduced pressure. The crude product was purified by column chromatography (petroleum ether-petroleum ether:ethyl acetate=4:1) to give 15a (662 mg, yield 85%).

Synthesis of Intermediate 15b

The compound 15a (662 mg, 2.27 mmol), bis(pinacolato) diboron (1.15 g, 4.54 mmol), potassium acetate (667 mg, 6.81 mmol) and [1,1'-bis(diphenylphosphino)ferrocene]dichloropalladium (146 mg, 0.20 mmol) were dissolved in anhydrous 1,4-dioxane (100 mL). The reaction mixture was reacted under nitrogen gas protection at 100° C. for 4 hours until no starting material was detected by TLC. To the reaction mixture was added water (100 mL). The mixture was extracted with ethyl acetate (100 mL×3). The organic phases were combined and dried over anhydrous sodium sulfate. The solvent was removed under reduced pressure. The crude product was purified by column chromatography (petroleum ether-petroleum ether:ethyl acetate=4:1) to give 15b (510 mg, yield 65%).

Synthesis of Intermediate 15c 15b (510 mg, 1.50 mmol) was dissolved in diethylene glycol dimethyl ether (150 mL). 5-fluoro-4-iodopyridine-2-amine (536 mg, 2.25 mmol), [1,1'-bis(diphenylphosphino) ferrocene]dichloropalladium (110 mg, 0.15 mmol) and potassium carbonate (621 mg, 4.50 mmol) were added at room temperature. The reaction mixture was stirred at 80° C. for 4 hours until no starting material was detected by TLC. To the reaction mixture was added water (100 mL). The mixture was extracted with ethyl acetate (100 mL×3). The organic phases were combined and dried over anhydrous sodium sulfate. The solvent was removed under reduced pressure. The crude product was purified by column chromatography (petroleum ether-petroleum ether:ethyl acetate=1:1) to give 15c (263 mg, yield 54%).

Synthesis of Intermediate 15d 15c (263 mg, 0.81 mmol) and (1S,3R)-3-[(tert-butyloxycarbonyl)amino]cyclohexanecarboxylic acid (290 mg, 1.23 mmol) were dissolved in N,N-dimethylformamide (20 mL). 2-(7-azabenzotriazol-1-yl)-N,N,N',N'-tetramethyluronium hexafluorophosphate (470 mg, 1.23 mmol) and diisopropylethylamine (480 mg, 3.69 mmol) were successively added. The reaction mixture was reacted at room temperature for 4 hours until no starting material was detected by TLC. To the reaction mixture was added water (100 mL). The mixture was extracted with ethyl acetate (100 mL×3). The organic phases were combined and dried over anhydrous sodium sulfate. The solvent was removed under reduced pressure. The crude product was purified by column chromatography (petroleum ether:ethyl acetate=4:1-2:1) to give 15d (250 mg, yield 56%).

Synthesis of Intermediate 15e 15d (250 mg, 0.45 mmol) was dissolved in dichloromethane (50 mL), and then trifluoroacetic acid (5 mL) was added. The reaction mixture was stirred at room temperature for 4 hours until no starting material was detected by TLC. To the mixture was added an aqueous saturated sodium carbonate solution. The pH value of the reaction mixture was adjusted to 9-10. The aqueous phase was separated and then extracted with dichloromethane (100 mL×3). The organic phases were combined and concentrated to a volume of about 50 mL. Triethylamine (2 mL) and acetic anhydride (2 mL) were added. The reaction mixture was reacted at room temperature for 30 minutes. An aqueous sodium carbonate solution was added to wash the organic phase, and the mixture was extracted with dichloromethane (20 mL×3). The organic phases were combined and dried over anhydrous sodium sulfate. The solvent was removed under reduced pressure. The crude product was purified by column chromatography (ethyl acetate) to give 15e (176 mg, yield 79%).

Synthesis of Final Product 15

15e (175 mg,0.36 mmol) was dissolved in methanol (20 mL), and palladium/carbon (10 mg) was added. The reaction mixture was reacted at room temperature under the protection of hydrogen gas for 10 hours until no starting material was detected by LC-MS. The palladium/carbon was filtered off, and the reaction solution was concentrated under reduced pressure to give the final product 15 (117 mg, yield 81%).

MS m/z (ESI): 402.2 $[M+H]^+$.

$^1$H NMR (600 MHz, DMSO-$d_6$) δ 10.49 (s, 1H), 10.09 (s, 1H), 8.25 (s, 1H), 8.05 (s, J=5.4 Hz, 1H), 7.78 (d, J=7.8 Hz, 1H), 7.07 (d, J=8.4 Hz, 1H), 6.55 (d, J=2.4 Hz, 1H), 6.48 (s, 1H), 3.71 (s, 3H), 3.55-3.53 (m, 1H), 2.61-2.57 (m, 1H), 1.87 (d, J=11.4 Hz, 1H), 1.77 (s, 3H), 1.77-1.75 (m, 3H), 1.29-1.27 (m, 4H).

Example 16

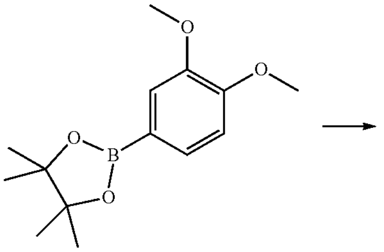

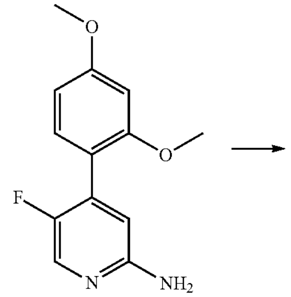

16a

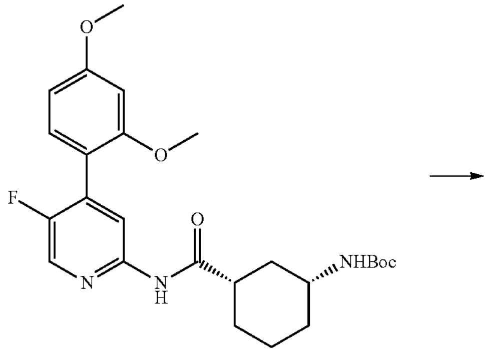

16b

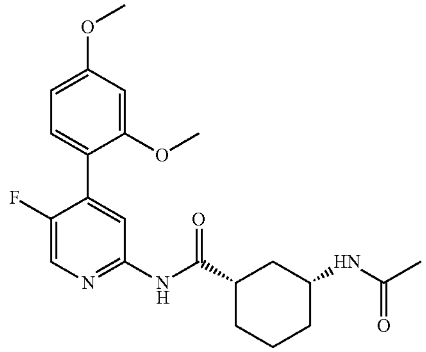

16

Synthesis of Intermediate 16a 2-(3,4-dimethoxyphenyl)-4,4,5,5-tetramethyl-1,3,2-dioxaborolane (150 mg, 0.57 mmol) and 5-fluoro-4-iodopyridin-2-amine (202 mg, 0.85 mmol) were dissolved in diethylene glycol dimethyl ether (50 mL), and [1,1'-bis(diphenylphosphino)ferrocene]dichloropalladium (37 mg, 0.05 mmol), potassium carbonate (117 mg, 0.85 mmol) and water (10 mL) were successively added. The reaction mixture was reacted at 80° C. under nitrogen gas protection for 4 hours until no starting material was detected by TLC. To the reaction solution was added water (50 mL). The mixture was extracted with ethyl acetate (100 mL×3). The organic phases were combined and dried over anhydrous sodium sulfate. The solvent was removed under reduced pressure. The crude product was purified by column chromatography (petroleum ether:ethyl acetate=4:1-1:1) to give 16a (124 mg, yield 88%).

Synthesis of Intermediate 16b

The compound 16a (36 mg, 0.15 mmol) was dissolved in N,N-dimethylformamide (10 mL), and then (1S,3R)-3-[(tert-butyloxycarbonyl)amino]cyclohexanecarboxylic acid (71 mg, 0.29 mmol), 2-(7-azabenzotriazol-1-yl)-N,N,N',N'-tetramethyluronium hexafluorophosphate (110 mg, 0.29 mmol) and diisopropylethylamine (57 mg, 0.44 mmol) were added. The reaction mixture was stirred and reacted at 25° C. for 15 hours until no starting material was detected by TLC. To the reaction solution was added water (15 mL). The mixture was extracted with ethyl acetate (20 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=4:1-2:1) to give 16b (35 mg, yield 49%).

Synthesis of Final Product 16

16b (35 mg, 0.074 mmol) was dissolved in dichloromethane (20 mL), and then trifluoroacetic acid (2 mL) was added. The reaction mixture was stirred at room temperature for 4 hours until no starting material was detected by TLC. To the mixture was added an aqueous saturated sodium carbonate solution. The pH value of the reaction mixture was adjusted to 9-10. The mixture was extracted with dichloromethane (50 mL×3). The organic phases were combined and concentrated to a volume of about 20 mL. Triethylamine (2 mL) and acetic anhydride (2 mL) were added. The reaction mixture was reacted at room temperature for 30 minutes. An aqueous sodium carbonate solution was added to wash the organic phase. The aqueous phase was extracted with dichloromethane (20 mL×3). The organic phases were combined, washed with saturated sodium chloride solution (50 mL×2), and dried over anhydrous sodium sulfate. The solvent was removed under reduced pressure. The crude product was purified by the silica-gel column chromatography (ethyl acetate) to give the final product 16 (15 mg, yield 49%).

MS m/z (ESI): 416.2 $[M+H]^+$.

$^1$H NMR (600 MHz, $CD_3OD$) δ 8.12 (s, 1H), 8.08 (d, J=5.4 Hz, 1H), 7.19 (d, J=8.4 Hz, 1H), 6.64 (s, 1H), 6.60 (s, 1H), 3.88 (s, 3H), 3.79 (s, 3H), 3.71 (t, J=4.8 Hz, 2H), 2.71-2.57 (m, 1H), 2.24-2.22 (m, 1H), 1.91 (s, 3H), 1.89 (s, 2H), 1.49-1.19 (m, 6H).

Example 17

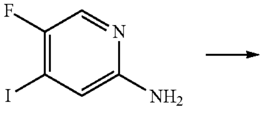

-continued

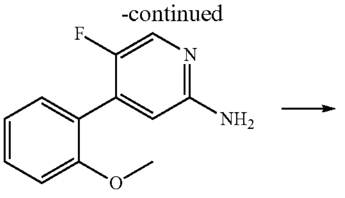

17a

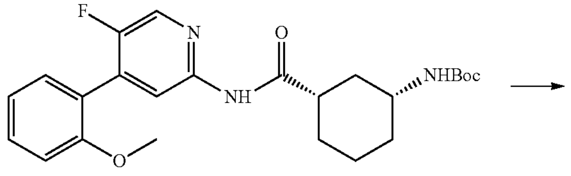

17b

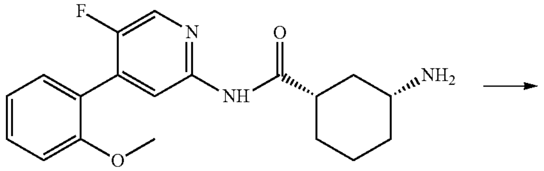

17c

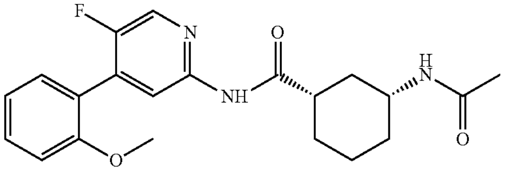

17

Synthesis of Intermediate 17a 2-methoxyphenylboronic acid (0.42 g, 2.77 mmol) was dissolved in diethylene glycol dimethyl ether (30 mL) and water (6 mL), and then 5-fluoro-4-iodopyridin-2-amine (0.60 g, 2.52 mmol), [1,1'-bis(diphenylphosphino)ferrocene] dichloropalladium (95 mg, 0.13 mmol) and potassium carbonate (1.04 g, 7.56 mmol) were added. The reaction mixture was stirred and reacted at 100° C. under nitrogen gas protection for 4 hours until no starting material was detected by TLC. To the reaction mixture was added water (50 mL). The mixture was extracted with ethyl acetate (50 mL×3). The organic phases were combined, washed with saturated sodium chloride (50 mL×2), and dried over anhydrous sodium sulfate. The solvent was removed under reduced pressure. The crude product was purified by column chromatography (petroleum ether:ethyl acetate=4:1-2:3) to give 17a (0.60 g, yield 99%).

Synthesis of Intermediate 17b 17a (0.60 g, 2.77 mmol) was dissolved in N,N-dimethylformamide (50 mL), and then (1S,3R)-3-[(tert-butyloxycarbonyl)amino]cyclohexanecarboxylic acid (0.79 g, 3.20 mmol), 2-(7-azabenzotriazol-1-yl)-N,N,N',N'-tetramethyluronium hexafluorophosphate (1.22 g, 3.20 mmol) and diisopropylethylamine (1.2 mL, 7.00 mmol) were added. The reaction mixture was stirred at room temperature for 15 hours until no starting material was detected by TLC. To the reaction mixture was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=4:1-2:3) to give 17b (0.60 g, yield 49%).

Synthesis of Intermediate 17c 17b (0.60 g, 1.35 mmol) was dissolved in dichloromethane (50 mL), and then trifluoroacetic acid (3 mL) was added. The reaction mixture was stirred and reacted at 25° C. until no starting material was detected by TLC. To the reaction solution was added an aqueous sodium carbonate solution (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product 17c can be directly used in the next step reaction.

Synthesis of Final Product 17

17c was dissolved in dichloromethane (50 mL), and then triethylamine (0.4 mL, 2.70 mmol) and acetic anhydride (0.3 mL, 2.70 mmol) were added. The reaction mixture was stirred at room temperature for 30 minutes, and the starting material was completely converted, as monitored by TLC. To the mixture was added an aqueous saturated sodium carbonate solution. The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=4:1-2:1) to give the final product 17 (0.35 g, yield 68%).

MS m/z (ESI): 386.2 $[M+H]^+$.

$^1H$ NMR (600 MHz, DMSO-$d_6$) δ 10.55 (s, 1H), 8.30 (s, 1H), 8.07 (d, J=5.4 Hz, 1H), 7.76 (d, J=7.8 Hz, 1H), 7.46 (t, J=7.8 Hz, 1H), 7.27 (d, J=7.2 Hz, 1H), 7.15 (d, J=8.4 Hz, 1H), 7.06 (t, J=7.8 Hz, 1H), 3.75 (s, 3H), 3.55-3.54 (m, 1H), 2.56-2.48 (m, 1H), 1.86-1.84 (m, 1H), 1.77-1.74 (m, 6H), 1.31-1.02 (m, 4H).

Example 18

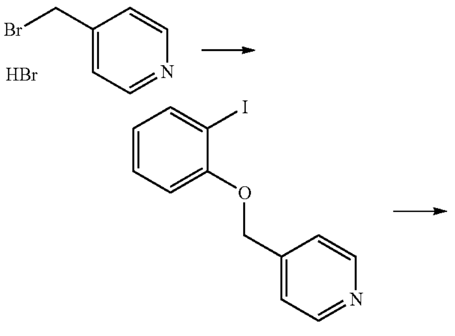

18a

-continued

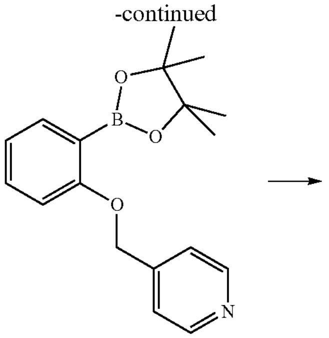

18b

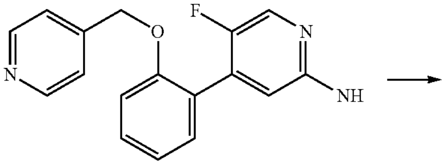

18c

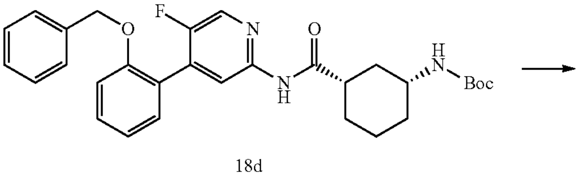

18d

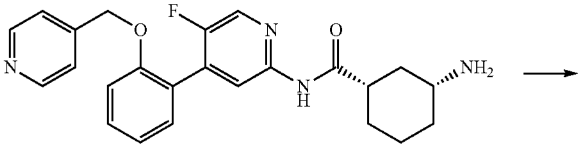

18e

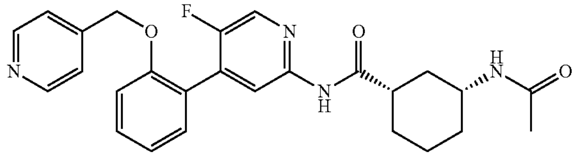

18

Synthesis of Intermediate 18a 4-(bromomethyl)pyridine hydrobromide (1.72 g, 6.81 mmol) was dissolved in N,N-dimethylformamide (20 mL), and then 2-iodophenol (1.50 g, 6.81 mmol), potassium carbonate (2.83 g, 20.45 mmol) and sodium iodide (1.02 g, 6.81 mmol) were added. The reaction mixture was stirred and reacted at room temperature for 4 hours until no starting material was detected by TLC. The reaction solution was directly purified by column chromatography (petroleum ether:ethyl acetate=2:1-petroleum ether:ethyl acetate=1:1) to give 18a (1.90 g, yield 90%).

Synthesis of Intermediate 18b 18a (1.00 g, 3.21 mmol) was dissolved in ethylene glycol dimethyl ether (15 mL), and then bis(pinacolato)diboron (980 mg, 3.85 mmol), [1,1'-bis(diphenylphosphino)ferrocene]dichloropalladium (234 mg, 0.32 mmol) and potassium acetate (0.95 g, 9.64 mmol) were added. The mixture was evacuated and backfilled with $N_2$ (3 times). The reaction mixture was stirred and reacted at 100° C. for 4 hours until no starting material was detected by TLC. The reaction solution was directly purified by column chromatography (petroleum ether:ethyl acetate=2:1-petroleum ether:ethyl acetate=1:1) to give the compound 18b (0.80 g, yield 80%).

Synthesis of Intermediate 18c 5-fluoro-4-iodopyridin-2-amine (802 mg, 3.37 mmol) was dissolved in ethylene glycol dimethyl ether (20 mL), and then 18b (700 mg, 2.25 mmol), [1,1'-bis(diphenylphosphino)ferrocene]dichloropalladium (168 mg, 0.23 mmol) and potassium carbonate (932 mg, 6.75 mmol) were added. The mixture was evacuated and backfilled with $N_2$ (3 times). The reaction mixture was stirred and reacted at 100° C. for 4 hours until no starting material was detected by TLC. The reaction solution was directly purified by column chromatography (dichloromethane:methanol=50:1-dichloromethane:methanol=10:1) to give 18c (220 mg, yield 33%).

Synthesis of Intermediate 18d 18c (220 mg, 0.75 mmol) was dissolved in N,N-dimethylformamide (10 mL), and then (1S,3R)-3-[(tert-butyloxycarbonyl)amino]cyclohexanecarboxylic acid (217 mg, 0.89 mmol), 2-(7-azabenzotriazol-1-yl)-N,N,N',N'-tetramethyluronium hexafluorophosphate (340 mg, 0.89 mmol) and N,N-dimethylethylamine (192 mg, 1.49 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-dichloromethane:methanol=20:1) to give 18d (300 mg, yield 77%).

Synthesis of Intermediate 18e 18d (0.30 g, 0.58 mmol) was dissolved in dichloromethane (30 mL) and then trifluoroacetic acid (2 mL) was added in an ice-water bath. The reaction mixture was stirred overnight at room temperature until no starting material was detected by TLC. To the reaction solution was added water (100 mL). Then the mixture was adjusted with an aqueous saturated sodium bicarbonate solution to a pH of 9-10. The mixture was extracted with dichloromethane (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-dichloromethane:methanol=8:1) to give 18e (0.16 g, yield 66%).

Synthesis of Final Product 18

18e (160 mg, 0.38 mmol) was dissolved in dichloromethane (5 mL), and then acetic anhydride (116 mg, 1.14 mmol) and triethylamine (115 mg, 1.14 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride solution (50 mL×2, and dried over anhydrous sodium sulfate. The solvent was removed under reduced pressure. The crude product was purified by column chromatography (petroleum ether:ethyl acetate=10:1-petroleum ether:ethyl acetate=2:1) to give the final product 18 (60 mg, yield 34%).

MS m/z (ESI): 463.2 $[M+H]^+$.

$^1$H NMR (600 MHz, DMSO-$d_6$) δ 10.61 (s, 1H), 8.50 (d, J=5.4 Hz, 2H), 8.36 (s, 1H), 8.20 (d, J=5.4 Hz, 1H), 7.80 (d, J=7.8 Hz, 1H), 7.47-7.44 (m, 1H), 7.35 (d, J=7.2 Hz, 1H), 7.30 (d, J=5.4 Hz, 2H), 7.18 (d, J=9.0 Hz, 1H), 7.15 (t, J=7.8 Hz, 1H), 5.22 (s, 2H), 3.58-3.57 (m, 1H), 2.62-2.53 (m, 1H), 1.89-1.75 (m, 7H), 1.30-1.04 (m, 4H).

Example 19

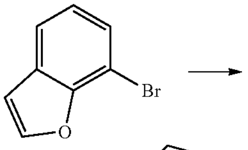

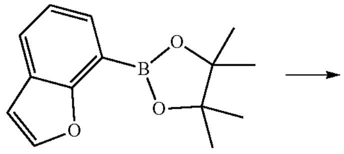

19a

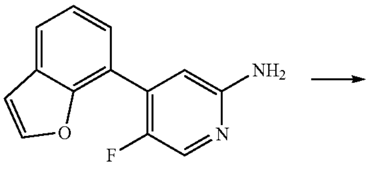

19b

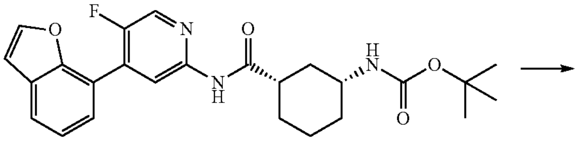

19c

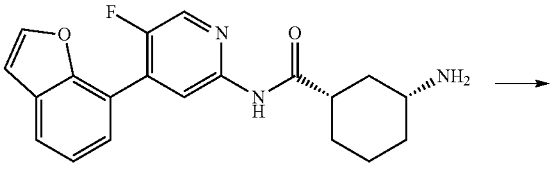

19d

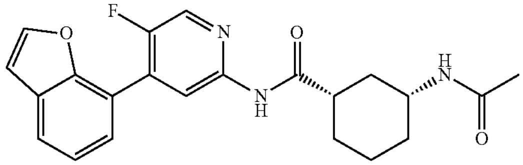

19

Synthesis of Intermediate 19a 7-bromobenzofuran (600 mg, 3.00 mmol) was dissolved in ethylene glycol dimethyl ether (50 mL), and then bis(pinacolato)diboron (928 mg, 3.70 mmol), [1,1'-bis(diphenylphosphino)ferrocene]dichloropalladium dichloromethane complex (163 mg, 0.20 mmol) and potassium acetate (892 mg, 9.10 mmol) were added. The reaction mixture was heated up to 100° C. under nitrogen gas protection and reacted for 4 hours. The starting material was completely converted, as monitored by TLC. The reaction solution was cooled down to room temperature. The crude product was purified by column chromatography (petroleum ether:ethyl acetate=100:1-50:1) to give 19a (450 mg, yield 62%).

Synthesis of Intermediate 19b 19a (450 mg, 1.84 mmol) was dissolved in ethylene glycol dimethyl ether (50 mL) and water (10 mL), and then 5-fluoro-4-iodopyridin-2-amine (350 mg, 1.47 mmol), [1,1'-bis(diphenylphosphino)ferrocene]dichloropalladium dichloromethane complex (110 mg, 0.15 mmol) and potassium carbonate (405 mg, 2.94 mmol) were added. The reaction mixture was heated up to 100° C. under nitrogen gas protection and reacted for 4 hours. The starting material was completely converted, as monitored by TLC. The reaction solution was cooled down to room temperature. The crude product was purified by column chromatography (petroleum ether:ethyl acetate=10:1-2:1) to give 19b (300 mg, yield 71%).

Synthesis of Intermediate 19c (1S,3R)-3-[(tert-butyloxycarbonyl)amino]cyclohexanecarboxylic acid (292 mg, 1.20 mmol) was dissolved in dichloromethane (50 mL), and then pyridine (474 mg, 6.00 mmol) and thionyl chloride (242 mg, 2.04 mmol) were added.

The reaction mixture was reacted at room temperature for 4 hours, and then 19b (300 mg, 1.32 mmol) was added to the above reaction solution. The reaction continued to proceed at room temperature overnight until no starting material was detected by TLC. The reaction solution was diluted with water (30 mL) and extracted. The organic phase was collected and concentrated under reduced pressure. The crude product was purified by column chromatography (petroleum ether:ethyl acetate=10:1-2:1) to give 19c (200 mg, yield 39%).

Synthesis of Intermediate 19d 19c (200 mg, 0.47 mmol) was dissolved in dichloromethane (10 mL), and then trifluoroacetic acid (1 mL) was added. The reaction mixture was reacted at room temperature for 1.5 hours until the starting material was completely converted, as monitored by TLC. To the reaction solution was added saturated sodium bicarbonate solution (30 mL). The mixture was extracted with dichloromethane (20 mL×3). The organic phases were combined, washed with saturated sodium chloride solution (20 mL×2), and dried over anhydrous sodium sulfate. The solvent was removed under reduced pressure to give 19d (128 mg, yield 83%).

Synthesis of Final Product 19

19d (128 mg, 0.39 mmol) was dissolved in dichloromethane (10 mL), and then acetic anhydride (48 mg, 0.47 mmol) and triethylamine (47 mg, 0.47 mmol) were added. The reaction mixture was reacted at room temperature for 1.5 hours until the starting material was completely converted, as monitored by TLC. To the reaction solution was added saturated sodium bicarbonate solution (30 mL). The mixture was extracted with dichloromethane (20 mL×3). The organic phases were combined, washed with saturated sodium chloride solution (20 mL×2), and dried over anhydrous sodium sulfate. The solvent was removed under reduced pressure. The crude product was purified by column chromatography (dichloromethane:methanol=50:1-20:1) to give the final product 19 (117 mg, yield 76%).

MS m/z (ESI): 396.2[M+H]$^+$.

$^1$H NMR (600 MHz, DMSO-$d_6$) δ 10.68 (s, 1H), 8.48 (s, 1H), 8.41 (d, J=5.4 Hz, 1H), 8.09 (s, 1H), 7.83-7.78 (m, 2H), 7.46 (d, J=7.2 Hz, 1H), 7.41 (dd, J=7.2 Hz, J=7.2 Hz, 1H), 7.09 (s, 1H), 3.58-3.56 (m, 1H), 2.64-2.60 (m, 1H), 1.90-1.84 (m, 1H), 1.78-1.76 (m, 6H), 1.31-1.25 (m, 3H), 1.10-1.06 (m, 1H).

Example 20

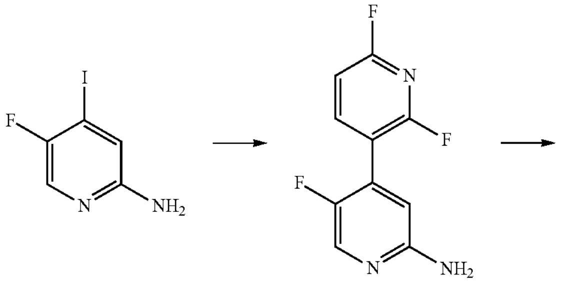

20a

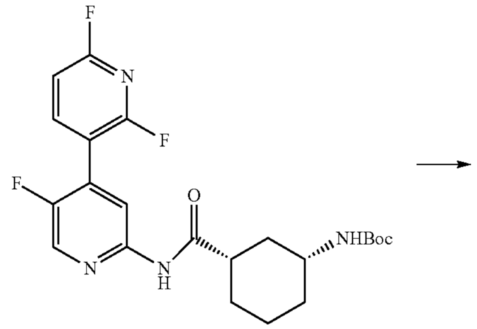

20b

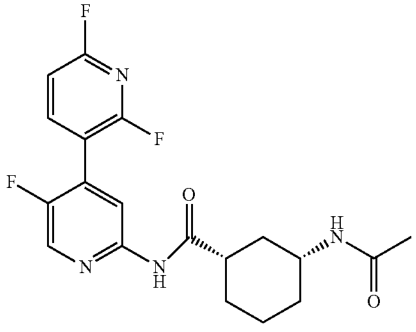

20

Synthesis of Intermediate 20a 2,6-difluoropyridine-3-boronic acid (550 mg, 3.14 mmol) and 5-fluoro-4-iodopyridin-2-amine (898 mg, 3.77 mmol) was dissolved in 1,4-dioxane (15 mL), [1,1'-bis(diphenylphosphino)ferrocene]dichloropalladium (219 mg, 0.30 mmol) and potassium carbonate (1.30 g, 9.42 mmol) were successively added, and then water (6 mL) was added. The reaction mixture was stirred and reacted for 5 hours at 100° C. under nitrogen gas protection until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=4:1-2:3) to give 20a (700 mg, yield 99%).

Synthesis of Intermediate 20b 20a (700 mg, 3.14 mmol) was dissolved in acetonitrile (50 mL), and then (1S,3R)-3-[(tert-butyloxycarbonyl)amino]cyclohexanecarboxylic acid (778 mg, 3.20 mmol), tetramethylchloroformamidinium hexafluorophosphate (898 mg, 3.20 mmol) and N-methyl imidazole (0.87 mL, 11.00 mmol) were added. The reaction mixture was stirred at room temperature for 15 hours until no starting material was detected by TLC. The solvent was removed by concentration, and the resulting crude product was purified by column chromatography (petroleum ether:ethyl acetate=4:1-2:3) to give 20b (1.40 g, yield 99%).

Synthesis of Final Product 20

20b (1.40 g, 3.14 mmol) was dissolved in dichloromethane (50 mL), and trifluoroacetic acid (5 mL) was added at room temperature. The reaction mixture was reacted for 4 hours until no starting material was detected by TLC. The reaction mixture was washed with an aqueous saturated sodium carbonate solution to weak alkalinity and extracted with dichloromethane (30 mL×3). The organic phases were combined and dried over anhydrous sodium sulfate. The solvent was concentrated to 50 mL, and then triethylamine (2 mL) and acetic anhydride (2 mL) were added. The reaction mixture was stirred at room temperature for 30 minutes until no starting material was detected by TLC. The mixture was washed with an anhydrous sodium carbonate solution and then extracted with dichloromethane (30 mL×3). The organic phases were combined. The solvent was removed under reduced pressure. The crude product was purified by column chromatography to give the final product 20 (750 mg, yield 61%).

MS m/z (ESI): 393.2[M+H]$^+$.

$^1$H NMR (600 MHz, DMSO-$d_6$) δ 10.74 (s, 1H), 8.50 (s, 1H), 8.40 (dd, J=16.8 Hz, J=7.8 Hz, 1H), 8.26 (d, J=6.0 Hz, 1H), 7.79 (d, J=7.8 Hz, 1H), 7.41 (dd, J=7.8 Hz, J=2.4 Hz, 1H), 3.60-3.55 (m, 1H), 2.64-2.60 (m, 1H), 1.91-1.88 (m, 1H), 1.78-1.76 (m, 6H), 1.29-1.27 (m, 3H), 1.09-1.06 (m, 1H).

Example 21

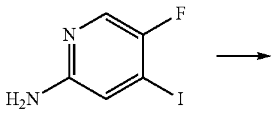

-continued

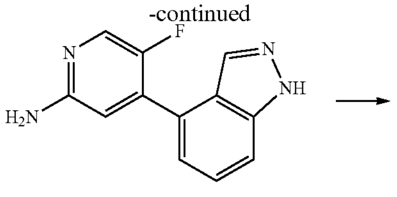

21a

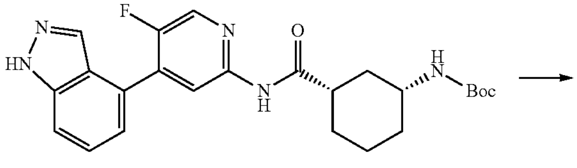

21b

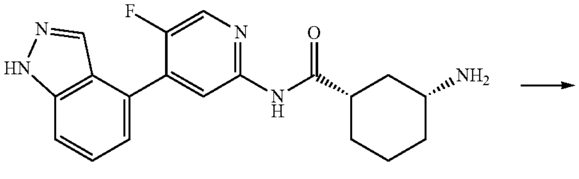

21c

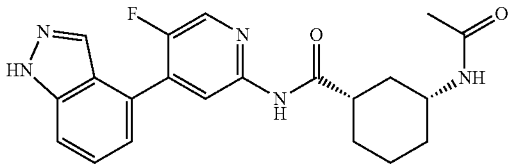

21

Synthesis of Intermediate 21a 5-fluoro-4-iodopyridin-2-amine (1.00 g, 4.20 mmol) was dissolved in ethylene glycol dimethyl ether (20 mL) and water (4 mL), and then indazole-4-boronic acid (0.68 g, 4.20 mmol), [1,1'-bis(diphenylphosphino)ferrocene]dichloropalladium (0.34 g, 0.42 mmol) and potassium carbonate (1.74 g, 12.60 mmol) were added. The mixture was evacuated and backfilled with $N_2$ (3 times). The reaction mixture was stirred and reacted at 100° C. for 4 hours until no starting material was detected by TLC. The mixture was concentrated under reduced pressure. The crude product was purified by column chromatography (dichloromethane:methanol=50:1-10:1) to give 21a (0.77 g, yield 80%).

Synthesis of Intermediate 21b 21a (0.75 g, 3.30 mmol) was dissolved in N,N-dimethylformamide (30 mL), and then (1S,3R)-3-[(tert-butyloxycarbonyl)amino]cyclohexanecarboxylic acid (0.80 g, 3.30 mmol), 2-(7-azabenzotriazol-1-yl)-N,N,N',N'-tetramethyluronium hexafluorophosphate (1.56 g, 4.10 mmol) and N,N-diisopropylethylamine (0.85 g, 6.60 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-20:1) to give 21b (0.91 g, yield 60%).

Synthesis of Intermediate 21c 21b (0.91 g, 2.00 mmol) was dissolved in dichloromethane (30 mL), and then trifluoroacetic acid (2 mL) was added in an ice-water bath. The reaction mixture was stirred overnight at room temperature until no starting material was detected by TLC. To the reaction solution was added water (100 mL). Then the mixture was adjusted with an aqueous saturated sodium bicarbonate solution to a pH of 9-10 and extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-8:1) to give 21c (0.61 g, yield 86%).

Synthesis of Final Product 21

21c (0.61 g, 1.72 mmol) was dissolved in dichloromethane (35 mL), and then acetic anhydride (0.53 g, 5.20 mmol) and triethylamine (0.52 g, 5.20 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=10:1-2:1) to give the final product 21 (0.32 g, yield 47%).

MS m/z (ESI): 396.1 $[M+H]^+$.

$^1H$ NMR (600 MHz, $CDCl_3$) δ 8.60 (s, 1H), 8.27 (s, 1H), 8.14 (s, 1H), 7.63 (d, J=7.8 Hz, 1H), 7.51 (d, J=7.8 Hz, 1H), 7.39 (d, J=6.6 Hz, 1H), 7.15 (d, J=7.2 Hz, 1H), 3.89-3.87 (m, 1H), 2.54-2.50 (m, 1H), 2.29 (d, J=12.0 Hz, 1H), 1.79-1.77 (m, 6H), 1.44-1.28 (m, 3H), 1.12-1.09 (m, 1H).

Example 22

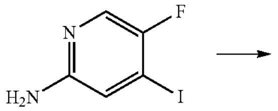

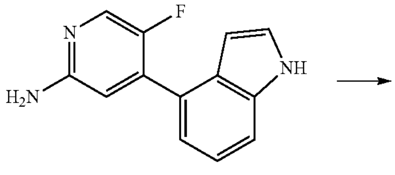

22a

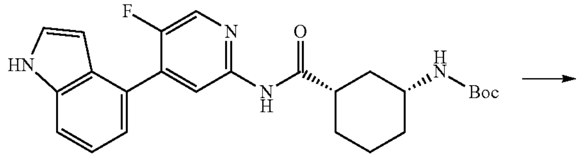

22b

-continued

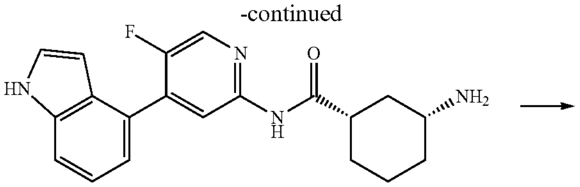

22c

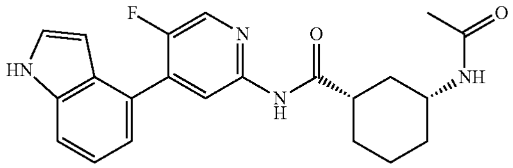

22

Synthesis of Intermediate 22a 5-fluoro-4-iodopyridin-2-amine (1.00 g, 4.20 mmol) was dissolved in ethylene glycol dimethyl ether (20 mL) and water (4 mL), and then indole-4-boronic acid (0.68 g, 4.20 mmol), [1,1'-bis(diphenylphosphino)ferrocene]dichloropalladium (0.34 g, 0.42 mmol) and potassium carbonate (1.74 g, 12.60 mmol) were added. The mixture was evacuated and backfilled with $N_2$ (3 times). The reaction mixture was stirred and reacted at 100° C. for 4 hours until no starting material was detected by TLC. The mixture was concentrated under reduced pressure. The crude product was purified by column chromatography (dichloromethane:methanol=50:1-10:1) to give 22a (0.78 g, yield 82%).

Synthesis of Intermediate 22b 22a (0.78 g, 3.40 mmol) was dissolved in N,N-dimethylformamide (30 mL), and then (1S,3R)-3-[(tert-butyloxycarbonyl)amino]cyclohexanecarboxylic acid (0.83 g, 3.40 mmol), 2-(7-azabenzotriazol-1-yl)-N,N,N',N'-tetramethyluronium hexafluorophosphate (1.56 g, 4.10 mmol) and N,N-diisopropylethylamine (0.88 g, 6.80 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-20:1) to give 22b (0.92 g, yield 59%).

Synthesis of Intermediate 22c 22b (0.92 g, 2.03 mmol) was dissolved in dichloromethane (30 mL), and then trifluoroacetic acid (2 mL) was added in an ice-water bath. The reaction mixture was stirred overnight at room temperature until no starting material was detected by TLC. To the reaction solution was added water (100 mL). Then the mixture was adjusted with an aqueous saturated sodium bicarbonate solution to a pH of 9-10 and extracted with dichloromethane (50 mL×3). The organic phases were combined, washed with saturated sodium chloride solution (50 mL×2), and dried over anhydrous sodium sulfate. The solvent was removed under reduced pressure.

The crude product was purified by column chromatography (dichloromethane:methanol=50:1-8:1) to give 22c (0.61 g, yield 85%).

Synthesis of Final Product 22

22c (0.61 g, 1.73 mmol) was dissolved in dichloromethane (35 mL), and then acetic anhydride (0.53 g, 5.20 mmol) and triethylamine (0.52 g, 5.20 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=10:1-2:1) to give the final product 22 (0.35 g, yield 51%).

MS m/z (ESI): 395.1 $[M+H]^+$.

$^1H$ NMR (600 MHz, DMSO-$d_6$) δ 11.38 (s, 1H), 10.59 (s, 1H), 8.42 (s, 1H), 8.36 (d, J=6.0 Hz, 1H), 7.77 (d, J=7.8 Hz, 1H), 7.54 (d, J=8.4 Hz, 1H), 7.46 (d, J=3.0 Hz, 1H), 7.23 (d, J=8.4 Hz, 1H), 7.15 (d, J=7.2 Hz, 1H), 6.41 (s, 1H), 3.60-3.54 (m, 1H), 2.64-2.60 (m, 1H), 1.89 (d, J=12.0 Hz, 1H), 1.77-1.76 (m, 6H), 1.34-1.23 (m, 3H), 1.10-1.08 (m, 1H).

Example 23

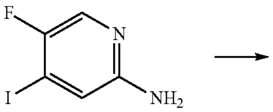

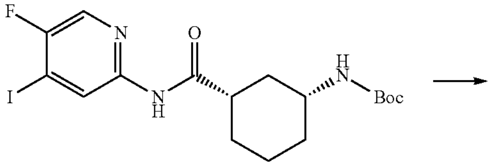

23a

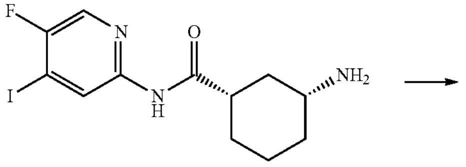

23b

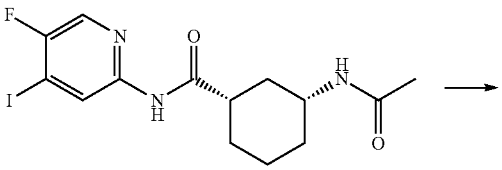

23c

-continued

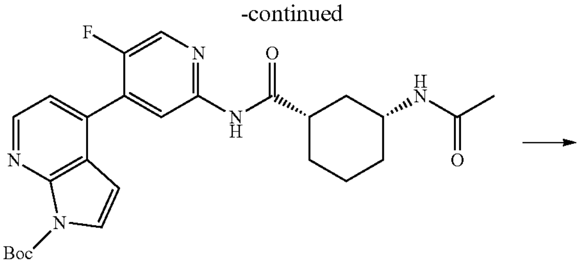

23d

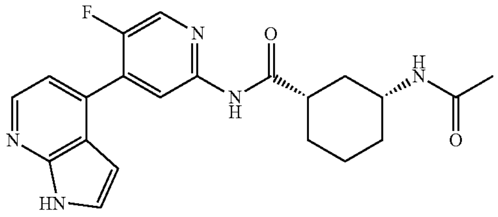

23

Synthesis of Intermediate 23a 5-fluoro-4-iodopyridin-2-amine (1.00 g, 4.20 mmol) was dissolved in N,N-dimethylformamide (20 mL), and then (1S,3R)-3-[(tert-butyloxycarbonyl)amino]cyclohexanecarboxylic acid (1.32 g, 5.40 mmol), 2-(7-azabenzotriazol-1-yl)-N,N,N',N'-tetramethyluronium hexafluorophosphate (2.39 g, 6.29 mmol) and N,N-dimethylethylamine (2.08 mL, 12.6 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-20:1) to give 23a (806 mg, yield 41%).

Synthesis of Intermediate 23b 23a (806 mg, 1.74 mmol) was dissolved in dichloromethane (10 mL), and then trifluoroacetic acid (5 mL) was added in an ice-water bath. The reaction mixture was stirred at room temperature for 2 hours until no starting material was detected by TLC. To the reaction solution was added water (100 mL). Then the mixture was adjusted with an aqueous saturated sodium bicarbonate solution to a pH of 9-10. The mixture was extracted with dichloromethane (50 mL×3). The organic phases were combined, washed with saturated sodium chloride solution (50 mL×2), and dried over anhydrous sodium sulfate. Then the solvent was removed under reduced pressure to give 23b (770 mg, crude product).

Synthesis of Intermediate 23c 23b (770 mg, crude product) was dissolved in dichloromethane (10 mL), and then triethylamine (883 μL, 6.35 mmol) and acetic anhydride (297 μL, 3.18 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (ethyl acetate) to give 23c (490 mg, yield 69%).

Synthesis of Intermediate 23d 23c (100 mg, 0.25 mmol) was dissolved in 1,4-dioxane (10 mL) and water (5 mL), and then tert-butyl 4-(4,4,5,5-tetramethyl-1,3,2-dioxaborolane-2-yl)-1H-pyrrolo[2,3-b]pyridine-1-carboxylate (167 mg, 0.49 mmol), [1,1'-bis(diphenylphosphino)ferrocene]dichloropalladium (15 mg, 0.02 mmol) and potassium carbonate (68 mg, 0.49 mmol) were added. The mixture was evacuated and backfilled with $N_2$ (3 times). The reaction mixture was stirred and reacted at 100° C. for 4 hours until no starting material was detected by TLC. The reaction solution was directly purified by column chromatography (dichloromethane:methanol=50:1-10:1) to give 23d (122 mg, yield 99%).

Synthesis of Final Product 23

23d (122 mg, 0.24 mmol) was dissolved in dichloromethane (10 mL), and then trifluoroacetic acid (5 mL) was added in an ice-water bath. The reaction mixture was stirred at room temperature for 2 hours until no starting material was detected by TLC. To the reaction solution was added water (100 mL). Then the mixture was adjusted with an aqueous saturated sodium bicarbonate solution to a pH of 9-10. The mixture was extracted with dichloromethane (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-10:1) to give the final product 23 (57 mg, yield 59%).

MS m/z (ESI): 396.2 $[M+H]^+$.

$^1H$ NMR (600 MHz, DMSO-$d_6$) δ 11.97 (s, 1H), 10.70 (s, 1H), 8.42 (s, 1H), 8.41 (s, 1H), 8.36 (d, J=4.8 Hz, 1H), 7.79 (d, J=7.8 Hz, 1H), 7.63-7.62 (m, 1H), 7.23 (d, J=4.2 Hz, 1H), 6.47 (s, 1H), 3.58-3.56 (m, 1H), 2.62-2.61 (m, 1H), 1.99 (d, J=4.8 Hz, 1H), 1.91-1.89 (m, 6H), 1.39-1.21 (m, 3H), 1.20-1.09 (m, 1H).

Example 24

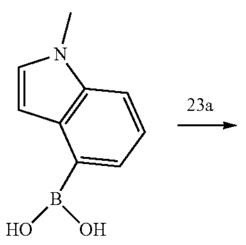

-continued

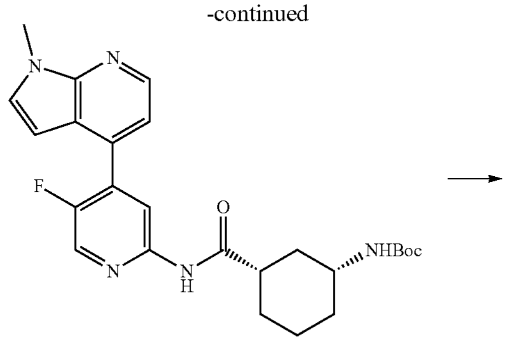

24a

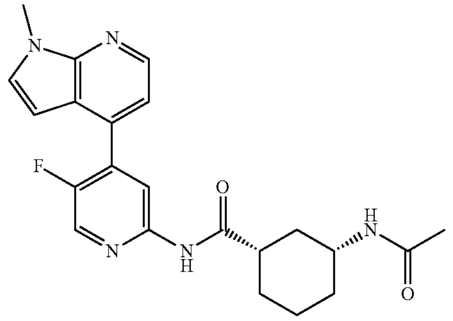

24

Synthesis of Intermediate 24a (1-methyl-1H-pyrrolo[2,3-b]pyridine-4-yl)boronic acid (176 mg, 1.00 mmol) and 23a (461 mg, 1.00 mmol) were dissolved in 1,4-dioxane (20 mL), and [1,1'-bis(diphenylphosphino)ferrocene]dichloropalladium (73 mg, 0.10 mmol) and potassium carbonate (414 mg, 3.00 mmol) were successively added. The reaction mixture was stirred and reacted at 100° C. under nitrogen gas protection for 4.5 hours, and the starting material was completely converted, as monitored by TLC. To the reaction mixture was added water (50 mL) and extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (petroleum ether:ethyl acetate=4:1-petroleum ether:ethyl acetate=1:1) to give 24a (400 mg, yield 86%).

Synthesis of Final Product 24

24a (400 mg, 0.86 mmol) was dissolved in dichloromethane (25 mL), and trifluoroacetic acid (3 mL) was added at room temperature. The reaction mixture was reacted at room temperature for 4 hours until no starting material was detected by TLC. The mixture was washed with a saturated sodium carbonate solution to weak alkalinity. The aqueous phase was extracted with dichloromethane (30 mL×3). The organic phases were combined and dried over anhydrous sodium sulfate. The solvent was concentrated to the volume of 15 mL. Triethylamine (2 mL) and acetic anhydride (2 mL) were added. The reaction mixture was reacted at room temperature for 30 minutes until no starting material was detected by TLC. The reaction mixture was washed with a saturated sodium carbonate solution, and the solvent was removed by concentration. The crude product was purified by the silica-gel column chromatography (dichloromethane: methanol=50:1-10:1) to give the final product 24 (169 mg, yield 48%).

MS m/z (ESI): 410.2 $[M+H]^+$.

$^1$H NMR (600 MHz, DMSO-$d_6$) δ 10.69 (s, 1H), 8.50 (s, 1H), 8.41 (s, 1H), 8.40 (s, 1H), 7.77 (d, J=7.8 Hz, 1H), 7.68 (d, J=3.6 Hz, 1H), 7.26 (d, J=4.8 Hz, 1H), 6.47 (d, J=2.4 Hz, 1H), 3.89 (s, 3H), 3.58-3.56 (m, 1H), 2.64-2.60 (m, 1H), 1.91-1.89 (m, 1H), 1.79-1.77 (m, 6H), 1.30-1.26 (m, 3H), 1.09-1.07 (m, 1H).

Example 25

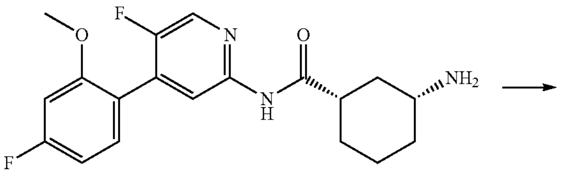

5b

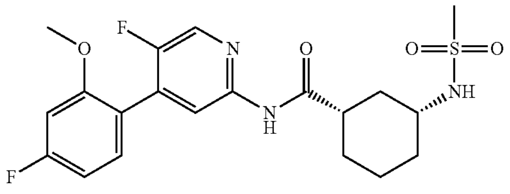

25

Synthesis of Final Product 25

5b (0.61 g, 1.69 mmol) was dissolved in dichloromethane (35 mL), and then methylsulfonyl chloride (0.29 g, 2.54 mmol) and triethylamine (0.34 g, 3.38 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=10:1-2:1) to give the final product 25 (0.41 g, yield 55%).

MS m/z (ESI): 440.1 $[M+H]^+$.

$^1$H NMR (600 MHz, DMSO-$d_6$) δ 10.60 (s, 1H), 8.33 (s, 1H), 8.08 (d, J=4.8 Hz, 1H), 7.34 (d, J=7.2 Hz, 1H), 7.10 (d, J=7.8 Hz, 2H), 6.92 (d, J=8.4 Hz, 1H), 3.80 (s, 3H), 3.13-3.11 (m, 1H), 2.92 (s, 3H), 2.62-2.57 (m, 1H), 2.03 (d, J=12 Hz, 1H), 2.25 (d, J=12 Hz, 1H), 1.77-1.73 (m, 2H), 1.36-1.11 (m, 4H).

Example 26

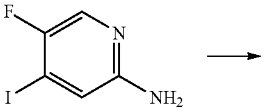

-continued

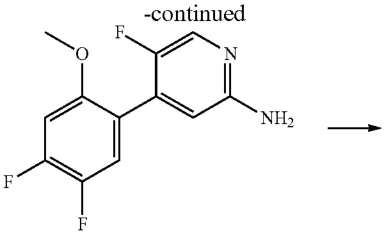

26a

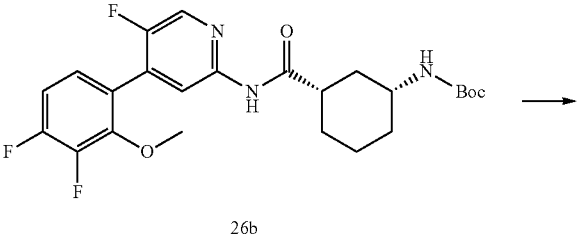

26b

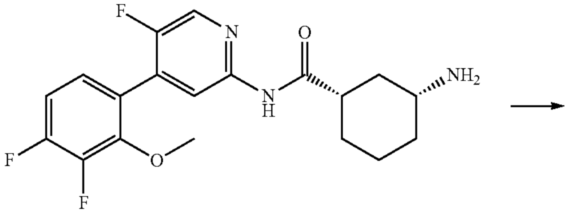

26c

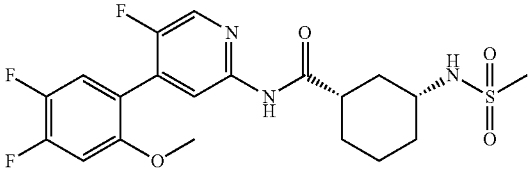

26

Synthesis of Intermediate 26a 5-fluoro-4-iodopyridin-2-amine (0.50 g, 2.10 mmol) was dissolved in ethylene glycol dimethyl ether (20 mL) and water (4 mL), and then 4,5-difluoro-2-methoxyphenylboronic acid (0.39 g, 2.10 mmol), [1,1'-bis(diphenylphosphino)ferrocene]dichloropalladium (0.15 g, 0.21 mmol) and potassium carbonate (0.87 g, 6.3 mmol) were added. The mixture was evacuated and backfilled with $N_2$ (3 times). The reaction mixture was stirred and reacted at 100° C. for 4 hours until no starting material was detected by TLC. The reaction solution was directly purified by column chromatography (dichloromethane:methanol=50:1-10:1) to give 26a (0.40 g, yield 75%).

Synthesis of Intermediate 26b 26a (0.30 g, 1.18 mmol) was dissolved in N,N-dimethylformamide (30 mL), and then (1S,3R)-3-[(tert-butyloxycarbonyl)amino]cyclohexanecarboxylic acid (0.35 g, 1.42 mmol), 2-(7-azabenzotriazol-1-yl)-N,N,N',N'-tetramethyluronium hexafluorophosphate (0.54 g, 1.42 mmol) and N,N-dimethylethylamine (0.30 g, 2.36 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-20:1) to give 26b (0.33 g, yield 58%).

Synthesis of Intermediate 26c 26b (0.20 g, 0.42 mmol) was dissolved in dichloromethane (30 mL), and then trifluoroacetic acid (2 mL) was added in an ice-water bath. The reaction mixture was stirred overnight at room temperature until no starting material was detected by TLC. To the reaction solution was added water (100 mL). Then the mixture was adjusted with an aqueous saturated sodium bicarbonate solution to a pH of 9-10 and extracted with dichloromethane (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-8:1) to give 26c (0.11 g, yield 70%).

Synthesis of Final Product 26

26c (0.11 g, 0.29 mmol) was dissolved in dichloromethane (35 mL), and then methylsulfonyl chloride (0.40 g, 0.35 mmol) and triethylamine (44 mg, 0.46 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=10:1-2:1) to give the final product 26 (40 mg, yield 30%).

MS m/z (ESI): 458.1 $[M+H]^+$.

$^1$H NMR (600 MHz, $CDCl_3$) δ 8.59 (s, 1H), 8.31 (s, 1H), 8.14 (d, J=10.8 Hz, 1H), 7.17 (d, J=9.0 Hz, 1H), 6.85-6.82 (m, 1H), 5.46 (s, 1H), 3.88 (s, 1H), 3.83 (s, 3H), 2.82 (s, 1H), 2.48 (s, 1H), 2.27-2.25 (m, 1H), 2.05-1.94 (m, 5H), 1.45-1.16 (m, 4H).

Example 27

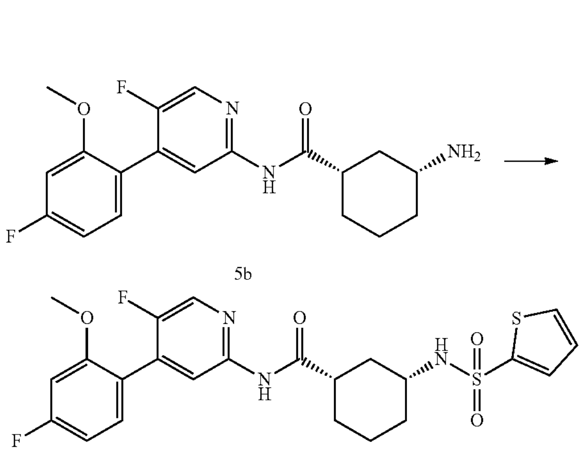

5b

27

Synthesis of Final Product 27

5b (0.61 g, 1.69 mmol) was dissolved in dichloromethane (35 mL), and then thiophene sulfonyl chloride (0.46 g, 2.53 mmol) and triethylamine (0.34 g, 3.38 mmol) were added. The reaction mixture was stirred at room temperature overnight until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=10:1-2:1) to give the final product 27 (0.52 g, yield 61%).

MS m/z (ESI): 508.1 $[M+H]^+$.

$^1$H NMR (600 MHz, DMSO-$d_6$) δ 10.55 (s, 1H), 8.31 (s, 1H), 8.03 (s, 1H), 7.96 (d, J=7.2 Hz, 1H), 7.89 (s, 1H), 7.57 (s, 1H), 7.32 (d, J=7.2 Hz, 1H), 7.15 (s, 1H), 7.08 (d, J=11.4 Hz, 1H), 6.89 (d, J=8.4 Hz, 1H), 4.02 (s, 3H), 3.04-3.03 (m, 1H), 1.78-1.62 (m, 5H), 1.17-1.08 (m, 4H).

Example 28

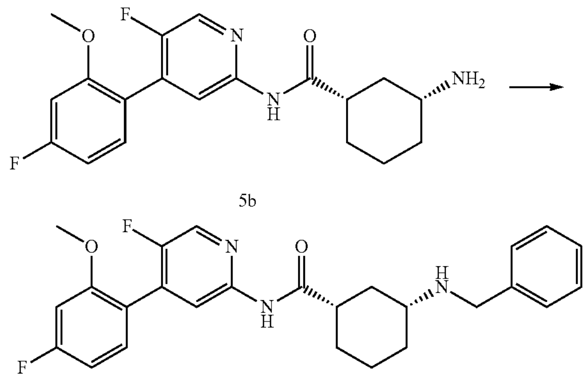

5b

28

Synthesis of Final Product 28

5b (79 mg, 0.22 mmol) was dissolved in acetonitrile (5 mL), and sodium carbonate (47 mg, 0.44 mmol) and benzyl bromide (37 mg, 0.22 mmol) were added. The reaction mixture was reacted at room temperature overnight until no starting material was detected by TLC. The solvent was removed by concentration. The crude product was purified by the thin layer chromatography (dichloromethane:methanol=10:1) to give the final product 28 (30 mg, yield 30%).

MS:(m/z, ESI): 451.2 $[M+H]^+$.

$^1$H NMR (600 MHz, $CD_3OD$) δ 8.16 (s, 1H), 8.09 (d, J=4.8 Hz, 1H), 7.37-7.32 (m, 4H), 7.30-7.26 (m, 2H), 6.93 (d, J=11.4 Hz, 1H), 6.80 (dd, J=8.4 Hz, 1H), 3.86 (s, 2H), 3.81 (s, 3H), 2.71-2.67 (m, 1H), 2.51-2.47 (m, 1H), 2.20-2.18 (m, 1H), 2.06-2.04 (m, 1H), 1.89-1.85 (m, 2H), 1.49-1.39 (m, 3H), 1.21-1.16 (m, 1H).

Example 29

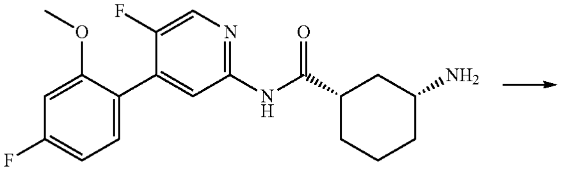

5b

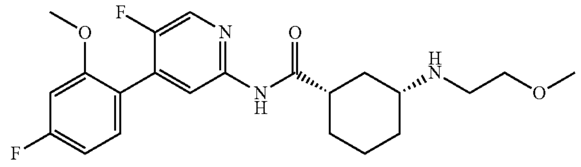

29

Synthesis of Final Product 29

5b (0.61 g, 1.69 mmol) was dissolved in N,N-dimethylformamide (35 mL), and then bromoethyl methyl ether (0.26 g, 1.86 mmol) and potassium carbonate (0.47 g, 3.38 mmol) were added. The reaction mixture was stirred at room temperature until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-20:1) to give the final product 29 (0.42 g, yield 59%).

MS m/z (ESI): 420.2 $[M+H]^+$.

$^1H$ NMR (600 MHz, $CDCl_3$) δ 8.25 (d, J=5.4 Hz, 1H), 8.12 (s, 1H), 7.25 (d, J=6.6 Hz, 1H), 6.75-6.70 (m, 2H), 3.80 (s, 3H), 3.57 (t, J=4.8 Hz, 2H), 3.36 (s, 3H), 2.90 (t, J=4.8 Hz, 2H), 2.70 (s, 1H), 2.37 (t, J=5.4 Hz, 1H), 2.26 (d, J=12.0 Hz, 1H), 2.05-1.90 (m, 3H), 1.52-1.22 (m, 4H).

Example 30

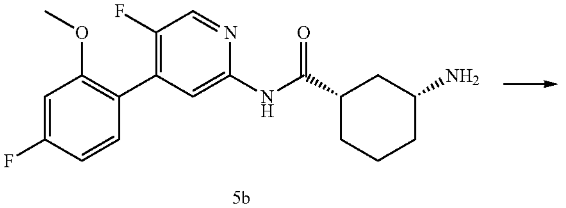

5b

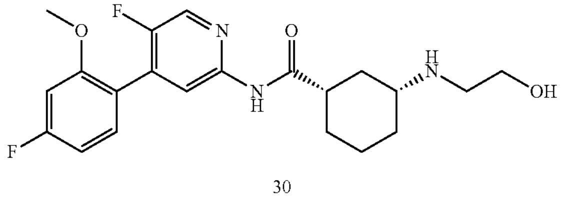

30

Synthesis of Final Product 30

5b (155 mg, 0.43 mmol) was dissolved in acetonitrile (5 mL), and triethylamine (86 mg, 0.86 mmol), bromoethanol (54 mg, 0.43 mmol) and sodium iodide (10 mg, 0.06 mmol) were added. The reaction mixture was reacted at 60° C. for 12 hours until no starting material was detected by TLC. The mixture was cooled and then concentrated to remove the solvent. The crude product was purified by the thin layer chromatography (dichloromethane:methanol:triethylamine=40:2:1) to give the final product 30 (30 mg, yield 17%).

MS m/z (ESI): 406.2 $[M+H]^+$.

$^1H$ NMR (600 MHz, $CD_3OD$) δ 8.18 (s, 1H), 8.08 (d, J=4.8 Hz, 1H), 7.28 (d, J=7.2 Hz, 1H), 6.92 (d, J=11.4 Hz, 1H), 6.79 (d, J=8.4, 1H), 3.82-3.80 (m, 5H), 3.20-3.25 (m, 1H), 3.20-3.18 (m, 2H), 2.65-2.62 (m, 1H), 2.31-2.29 (m, 1H), 2.18-2.16 (m, 1H), 1.99-1.91 (m, 2H), 1.70-1.64 (m, 1H), 1.53-1.34 (m, 3H).

Example 31

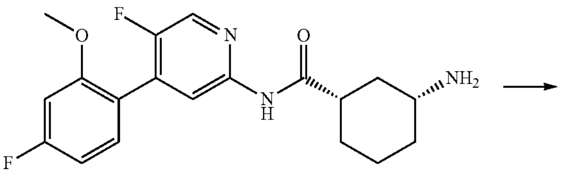

5b

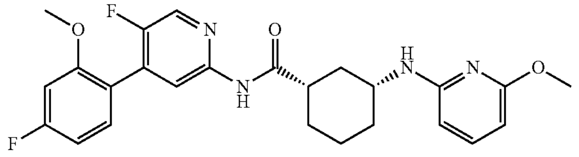

31

Synthesis of Final Product 31

5b (79 mg, 0.22 mmol) was dissolved in dioxane (5 mL), and then 2-bromo-6-methoxypyridine (40 mg, 0.22 mmol), tris(dibenzylideneacetone)dipalladium (20 mg, 0.022 mmol), 4,5-bis(diphenylphosphino)-9,9-dimethylxanthene (12.7 mg, 0.022 mmol) and cesium carbonate (215 mg, 0.66 mmol) were added. The mixture was evacuated and back-filled with $N_2$ (3 times). The reaction mixture was reacted at 120° C. for 2 hours until no starting material was detected by TLC. The mixture was cooled and then concentrated to remove the solvent. The crude product was purified by the thin layer chromatography (dichloromethane:methanol=10:1) to give the final product 31 (30 mg, yield 29%).

MS:(m/z, ESI): 469.2 $[M+H]^+$.

$^1H$ NMR (600 MHz, DMSO-$d_6$) δ 10.56 (s, 1H), 8.31 (s, 1H), 8.07 (d, J=5.4 Hz, 1H), 7.32 (d, J=7.2 Hz, 1H), 7.24 (d, J=7.8 Hz, 1H), 7.08 (d, J=11.4 Hz, 1H), 6.89 (d, J=8.4 Hz, 1H), 6.33 (d, J=7.2 Hz, 1H), 5.97 (d, J=7.8 Hz, 1H), 5.80 (d, J=7.8 Hz, 1H), 3.76 (s, 3H), 3.72 (s, 3H), 3.63-3.61 (m, 1H), 2.64-2.62 (m, 1H), 2.06-2.04 (m, 1H), 1.97-1.95 (m, 1H), 1.79-1.77 (m, 2H), 1.36-1.30 (m, 3H), 1.11-1.09 (m, 1H).

Example 32

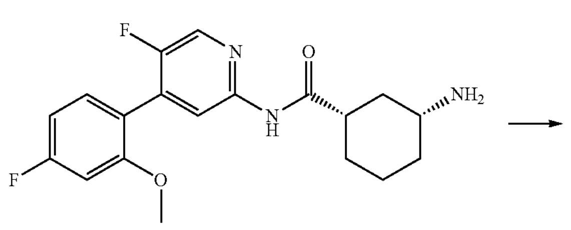

5b

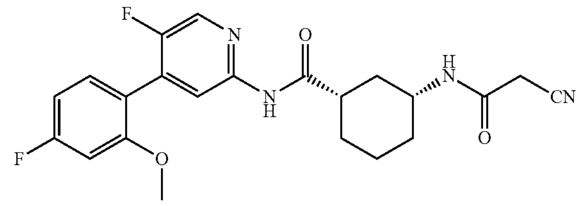

32

Synthesis of Final Product 32

5b (61 mg, 0.17 mmol) was dissolved in N,N-dimethylformamide (5 mL), and then cyanoacetic acid (16 mg, 0.18 mmol), 2-(7-azabenzotriazol-1-yl)-N,N,N',N'-tetramethyluronium hexafluorophosphate (69 mg, 0.18 mmol) and N,N-diisopropylethylamine (83 μL, 0.50 mmol) were added. The reaction mixture was stirred and reacted at room temperature for 10 hours until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=40:1-20:1) to give the final product 32 (50 mg, yield 71%).

MS m/z (ESI): 429.2[M+H]$^+$.

$^1$H NMR (600 MHz, DMSO-d$_6$) δ 10.58 (s, 1H), 8.31 (s, 1H), 8.20 (d, J=7.8 Hz, 1H), 8.06 (d, J=5.4 Hz, 1H), 7.32 (t, J=7.2 Hz, 1H), 7.08 (d, J=11.4 Hz, 1H), 6.90 (t, J=8.4 Hz, 1H), 3.77 (s, 3H), 3.56 (m, 3H), 2.61-2.57 (m, 1H), 1.89-1.76 (m, 4H), 1.30-1.07 (m, 4H).

Example 33

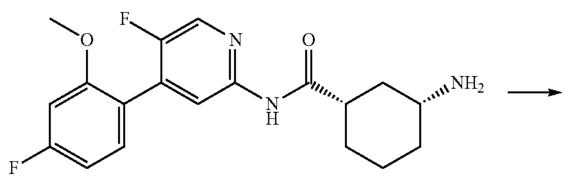

5b

-continued

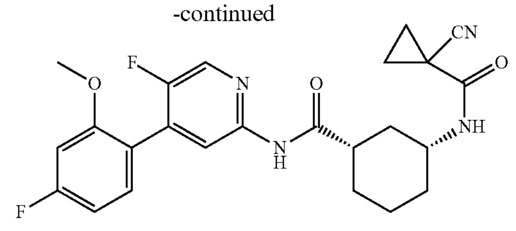

33

Synthesis of Final Product 33

5b (0.16 g, 0.43 mmol) was dissolved in N,N-dimethylformamide (30 mL), and then 1-cyano-1-cyclopropane carboxylic acid (72 mg, 0.65 mmol), 2-(7-azabenzotriazol-1-yl)-N,N,N',N'-tetramethyluronium hexafluorophosphate (178 mg, 0.47 mmol) and N,N-diisopropylethylamine (111 mg, 0.86 mmol) was added. The reaction mixture was stirred at room temperature overnight until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane: methanol=50:1-20:1) to give the final product 33 (96 mg, yield 49%).

MS m/z (ESI): 455.2 [M+H]$^+$.

$^1$H NMR (600 MHz, DMSO-d$_6$) δ 10.56 (s, 1H), 8.31 (s, 1H), 8.05 (d, J=4.8 Hz, 1H), 8.09 (d, J=7.8 Hz, 1H), 7.32 (dd, J=7.8 Hz, J=7.2 Hz, 1H), 7.09 (d, J=11.4 Hz, 1H), 6.90 (dd, J=8.4 Hz, J=7.8 Hz, 1H), 3.77 (s, 3H), 3.68-3.56 (m, 1H), 3.59-3.55 (m, 1H), 1.81-1.67 (m, 4H), 1.53-1.46 (m, 5H)), 1.28-1.23 (m, 3H).

Example 34

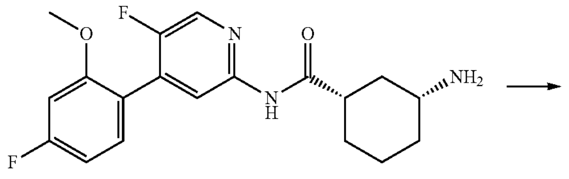

5b

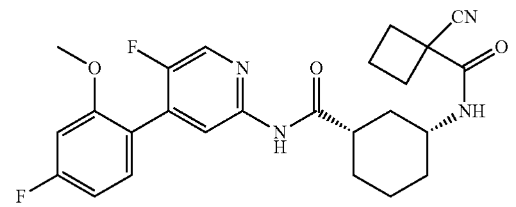

34

Synthesis of Final Product 34

5b (0.16 g, 0.43 mmol) was dissolved in N,N-dimethylformamide (30 mL), and then 1-cyanocyclobutane carboxylic acid (81 mg, 0.65 mmol), 2-(7-azabenzotriazol-1-yl)-

N,N,N',N'-tetramethyluronium hexafluorophosphate (178 mg, 0.47 mmol) and N,N-diisopropylethylamine (111 mg, 0.86 mmol) was added. The reaction mixture was stirred at room temperature overnight until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane: methanol=50:1-20:1) to give the final product 34 (119 mg, yield 59%).

MS m/z (ESI): 469.2 $[M+H]^+$.

$^1$H NMR (600 MHz, DMSO-d6) δ 10.56 (s, 1H), 8.31 (s, 1H), 8.05 (d, J=4.8 Hz, 1H), 8.09 (d, J=7.8 Hz, 1H), 7.34-7.31 (m, 1H), 7.09 (s, 1H), 6.91-6.88 (m, 1H), 3.77 (s, 3H), 3.68-3.56 (m, 1H), 2.59-2.55 (m, 1H), 1.81-1.67 (m, 4H), 1.53-1.46 (m, 5H), 1.30-1.23 (m, 5H).

Example 35

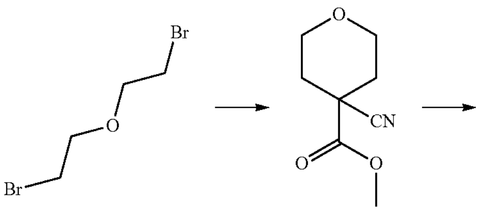

35a

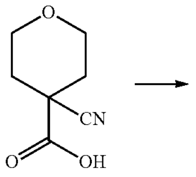

35b

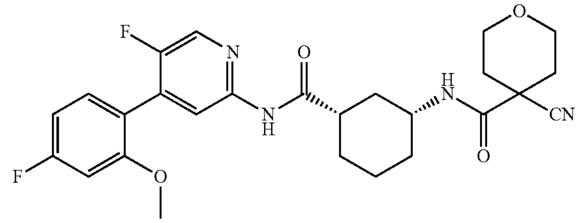

35

Synthesis of Intermediate 35a 2,2'-dibromo diethylether (12.85 g, 55.60 mmol) was dissolved in N,N-dimethylformamide (10 mL), and then methyl cyanoacetate (5.00 g, 50.45 mmol) and 1,8-diazabicyclo[5.4.0]undec-7-ene (11.50 g, 75.68 mmol) were added. The mixture was evacuated and backfilled with $N_2$ (3 times). The reaction mixture was stirred and reacted at 85° C. for 4 hours until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The crude product was purified by column chromatography (petroleum ether:ethyl acetate=1:1) to give 35a (5.00 g, yield 59%).

Synthesis of Intermediate 35b 35a (2.37 g, 14.00 mmol) was dissolved in ethanol (36 mL) and water (5 mL), and then sodium hydroxide (2.24 g, 56.00 mmol) was added. The reaction mixture was stirred at room temperature for 4 hours until no starting material was detected by TLC. To the reaction solution was added water (100 mL). The mixture was adjusted with an aqueous sodium bicarbonate solution to the pH of 8. The mixture was extracted with ethyl acetate (50 mL×3). The organic phases were combined, washed with saturated sodium chloride solution (50 mL×2), and dried over anhydrous sodium sulfate. The solvent was removed under reduced pressure to give 35b (1.50 g, yield 69%).

Synthesis of Final Product 35

35b (123 mg, 0.79 mmol) was dissolved in N,N-dimethylformamide (5 mL), and then (1S,3R)-3-amino-N-(5-fluoro-4-(4-fluoro-2-methoxyphenyl)pyridin-2-yl) cyclohexanecarboxamide (260 mg, 0.72 mmol), 2-(7-azabenzotriazol-1-yl)-N,N,N',N'-tetramethyluronium hexafluorophosphate (548 mg, 1.44 mmol) and N,N-diisopropylethylamine (357 μL, 2.16 mmol) were added. The reaction mixture was stirred and reacted at room temperature for 10 hours until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=40:1-20:1) to give the final product 35 (214 mg, yield 60%).

MS m/z (ESI): 499.2$[M+H]^+$.

$^1$H NMR (600 MHz, DMSO-$d_6$) δ 10.58 (s, 1H), 8.33 (s, 1H), 8.17 (d, J=7.8 Hz, 1H), 8.08 (d, J=6.0 Hz, 1H), 7.35-7.33 (m, 1H), 7.11-7.09 (m, 1H), 6.93-6.89 (m, 1H), 3.88-3.86 (m, 2H), 3.78 (s, 3H), 3.66-3.63 (m, 1H), 3.52-3.51 (m, 2H), 2.63 (m, 1H), 1.97-1.96 (m, 4H), 1.85-1.75 (m, 4H), 1.38-1.21 (m, 4H).

Example 36

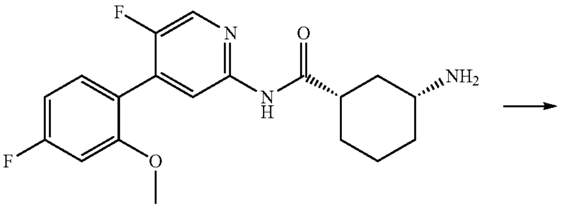

5b

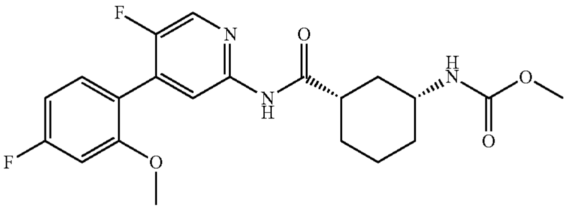

36

Synthesis of Final Product 36

Triphosgene (33 mg, 0.11 mmol) was dissolved in dichloromethane (2 mL), and then a solution of 5b (61 mg, 0.17 mmol) and triethylamine (22 mg, 0.22 mmol) dissolved in dichloromethane (2 mL) was added dropwise. The reaction mixture was stirred and reacted at room temperature for 2 hours, and then a methanol solution (2 mL) was added. The reaction continued to proceed for 3 hours until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane: methanol=40:1-20:1) to give the final product 36 (30 mg, yield 42%).

MS m/z (ESI): 420.2[M+H]$^+$.

$^1$H NMR (600 MHz, DMSO-$d_6$) δ 10.56 (s, 1H), 8.31 (s, 1H), 8.06 (d, J=5.4 Hz, 1H), 7.33 (d, J=7.8 Hz, 1H), 7.10-7.07 (m, 2H), 6.90 (d, J=8.4 Hz, 1H), 3.77 (s, 3H), 3.48 (s, 3H), 3.32 (m, 1H), 2.56 (m, 1H), 1.87-1.71 (m, 4H), 1.31-1.06 (m, 4H).

Example 37

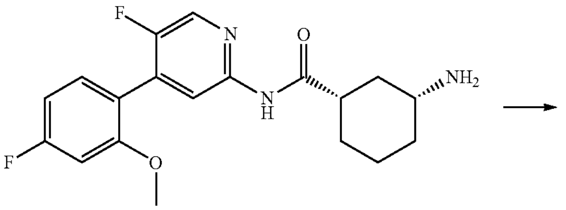

5b

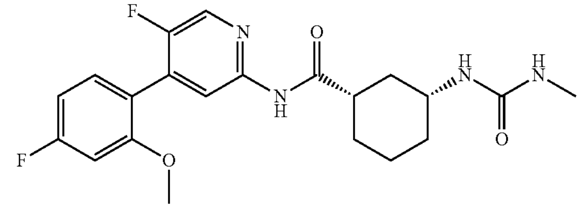

37

Synthesis of Final Product 37

Triphosgene (33 mg, 0.11 mmol) was dissolved in dichloromethane (2 mL), and then a solution of 5b (61 mg, 0.17 mmol) and triethylamine (22 mg, 0.22 mmol) dissolved in dichloromethane was added dropwise. The reaction mixture was stirred and reacted at room temperature for 2 hours, and then a solution of methylamine in ethanol (33%, 3 mL) was added. The reaction continued to proceed for 3 hours until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=40:1-20:1) to give the final product 37 (15 mg, yield 21%).

MS m/z (ESI): 419.2[M+H]$^+$.

$^1$H NMR (600 MHz, DMSO-$d_6$) δ 10.56 (s, 1H), 8.31 (s, 1H), 8.06 (d, J=5.4 Hz, 1H), 7.33 (t, J=8.4 Hz, 1H), 7.10-7.07 (m, 1H), 6.91-6.88 (m, 1H), 5.78 (d, J=8.4 Hz, 1H), 5.56 (d, J=4.8 Hz, 1H), 3.76 (s, 3H), 3.36-3.34 (m, 1H), 2.65-2.55 (m, 1H), 2.51 (s, 3H), 1.88-1.73 (m, 4H), 1.28-0.82 (m, 4H).

Example 38

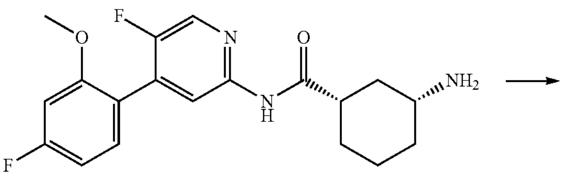

5b

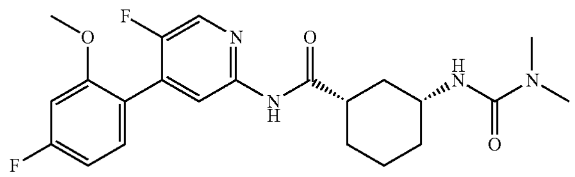

38

Synthesis of Final Product 38

5b (0.61 g, 1.69 mmol) was dissolved in dichloromethane (35 mL), and then dimethylcarbamic chloride (0.27 g, 2.54 mmol) and triethylamine (0.34 g, 3.38 mmol) were added. The reaction mixture was stirred overnight at room temperature until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=100:1-40:1) to give the final product 38 (0.38 g, yield 53%).

MS m/z (ESI): 433.1 [M+H]$^+$.

$^1$H NMR (600 MHz, $CDCl_3$) δ 8.28-8.25 (m, 2H), 8.11 (s, 1H), 7.27-7.24 (m, 2H), 6.76-6.70 (m, 2H), 3.81 (s, 3H), 3.76- 3.73 (m, 1H), 2.88 (s, 6H), 2.47-2.43 (m, 1H), 2.30 (d, J=12.0 Hz, 1H), 2.02-1.90 (m, 3H), 1.47-1.12 (m, 4H).

Example 39

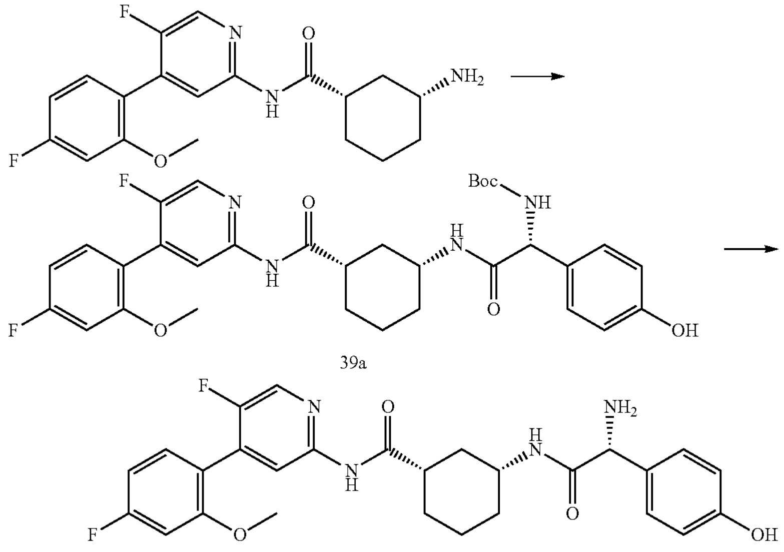

39a

39

Synthesis of Intermediate 39a 5b (0.12 g, 0.33 mmol) was dissolved in N,N-dimethylformamide (10 mL), and (S)-2-((tert-butyloxycarbonyl) amino)-2-(4-hydroxy phenyl) acetic acid (0.10 g, 0.36 mmol), 2-(7-azabenzotriazol-1-yl)-N,N,N',N'-tetramethyluronium hexafluorophosphate (0.15 g, 0.40 mmol), N,N-diisopropylethylamine (0.09 g, 0.66 mmol) were added. The reaction mixture was reacted at room temperature for 8 hours until no starting material was detected by TLC. To the reaction solution was added water (20 mL). The mixture was extracted with ethyl acetate (15 mL×3). The organic phases were combined and dried over anhydrous sodium sulfate. The organic phase was directly purified by column chromatography (dichloromethane:methanol=10:1) to give 39a (0.12 g, yield 60%).

Synthesis of Final Product 39

39a (0.12 g, 0.20 mmol) was dissolved in dichloromethane (20 mL), and trifluoroacetic acid (4 mL) was added. The reaction mixture was reacted at room temperature for 4 hours until no starting material was detected by TLC. The reaction solution was washed with water (20 mL×3), and the aqueous phases were combined. The combined aqueous phase was adjusted with sodium carbonate to a pH of 8-9 and extracted with dichloromethane (30 mL×3). The organic phases were combined and dried over anhydrous sodium sulfate. The organic phase was removed by evaporation under reduced pressure to give the final product 39 (0.04 g, yield 39%).

MS m/z (ESI): 511.2 $[M+H]^+$.

$^1$H NMR (600 MHz, DMSO-$d_6$) δ 10.56 (s, 1H), 9.23 (s, 1H), 8.32 (s, 1H), 8.08 (d, J=5.4 Hz, 1H), 7.90-7.89 (m, 1H), 7.36-7.34 (m, 1H), 7.17-7.15 (m, 2H), 7.12-7.10 (m, 1H), 6.93-6.91 (m, 1H), 6.68-6.66 (m, 2H), 4.19 (s, 1H), 4.04 (d, J=7.2 Hz, 2H), 3.80 (s, 3H), 3.58-3.57 (m, 1H), 2.59-2.57 (m, 1H), 1.80-1.76 (m, 4H), 1.33-1.25 (m, 4H).

Example 40

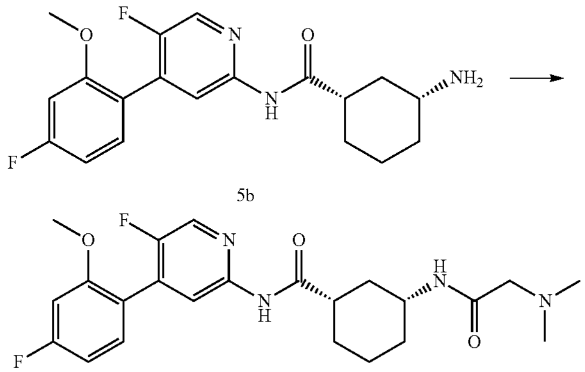

5b

40

Synthesis of Final Product 40

5b (0.20 g, 0.55 mmol) was dissolved in N,N-dimethylformamide (30 mL), and then N,N-dimethyl glycine (67 mg, 0.65 mmol), 2-(7-azabenzotriazol-1-yl)-N,N,N',N'-tetramethyluronium hexafluorophosphate (178 mg, 0.47 mmol) and N,N-diisopropylethylamine (111 mg, 0.86 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-20:1) to give the final product 40 (100 mg, yield 41%).

MS m/z (ESI): 447.2 $[M+H]^+$.

$^1H$ NMR (600 MHz, DMSO-$d_6$) δ 10.56 (s, 1H), 8.31 (s, 1H), 8.06 (d, J=4.2 Hz, 1H), 7.58 (d, J=8.4 Hz, 1H), 7.32 (dd, J=7.8 Hz, J=7.2 Hz, 1H), 7.08 (d, J=10.8 Hz, 1H), 6.90 (dd, J=7.8 Hz, J=7.8 Hz, 1H), 3.76 (s, 3H), 3.65-3.63 (m, 1H), 2.84-2.77 (m, 2H), 2.66-2.60 (m, 1H), 2.16 (s, 6H), 1.85-1.84 (m, 1H), 1.75-1.69 (m, 3H), 1.41-1.35 (m, 1H), 1.32-1.23 (m, 3H).

Example 41

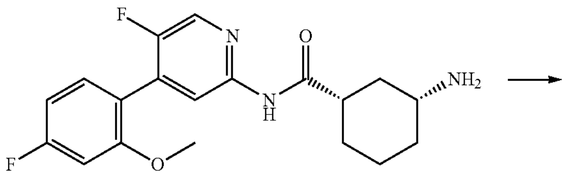

5b

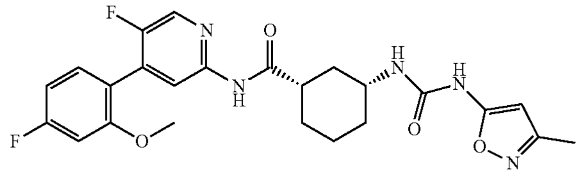

41

Synthesis of Compound 41

Triphosgene (0.027 g, 0.09 mmol) was dissolved in anhydrous tetrahydrofuran (20 mL), and a solution of 3-methylisoxazole-5-amine (0.027 g, 0.28 mmol) in tetrahydrofuran, and triethylamine (0.028 g, 0.28 mmol) were added. The reaction mixture was reacted at room temperature for 6 hours. To the reaction solution were added a solution of 5b (0.10 g, 0.28 mmol) in tetrahydrofuran, and triethylamine (0.028 g, 0.28 mmol). The reaction mixture was heated to 70° C. and reacted for 6 hours until no starting material was detected by TLC. The reaction mixture was cooled to room temperature. The reaction solution was purified by column chromatography (petroleum ether:ethyl acetate=1:1) to give the final product 41 (45 mg, yield 33%).

MS m/z (ESI): 486.2 $[M+H]^+$.

$^1H$ NMR (600 MHz, $CDCl_3$) δ 8.65 (s, 1H), 8.29 (s, 1H), 8.12 (s, 1H), 6.76-6.71 (m, 2H), 6.23 (s, 2H), 5.43 (s, 1H), 4.03-4.01 (m, 1H), 3.81 (s, 3H), 2.54-2.53 (m, 1H), 2.35 (s, 3H), 2.36-2.24 (m, 2H), 2.05-1.94 (m, 3H), 1.56-1.50 (m, 3H).

Example 42

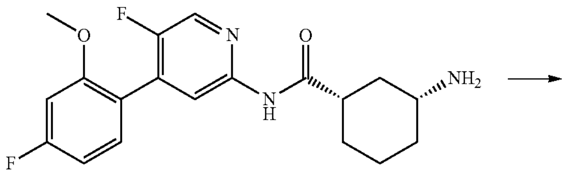

5b

-continued

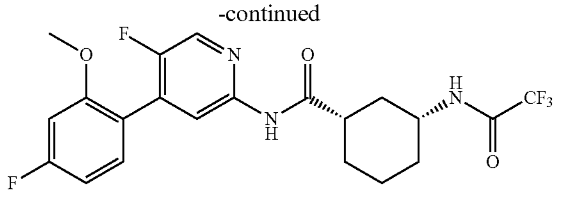

42

Synthesis of Final Product 42

5b (100 mg, 0.28 mmol) was dissolved in dichloromethane (10 mL), and then trifluoroacetic anhydride (56 mg, 0.55 mmol) and triethylamine (56 mg, 0.55 mmol) were added. The reaction mixture was reacted at room temperature for 1.5 hours until no starting material was detected by TLC. To the reaction solution was added saturated sodium bicarbonate solution (30 mL).

The mixture was extracted with dichloromethane (20 mL×3). The organic phases were combined, washed with saturated sodium chloride solution (20 mL×2), and dried over anhydrous sodium sulfate. The solvent was removed under reduced pressure. The crude product was purified by column chromatography (dichloromethane:methanol=50:1-20:1) to give the final product 42 (100 mg, yield 78%).

MS m/z (ESI): 458.1 $[M+H]^+$.

$^1H$ NMR (600 MHz, DMSO-$d_6$) δ 10.59 (s, 1H), 9.33 (d, J=8.4 Hz, 1H), 8.31 (s, 1H), 8.05 (d, J=6 Hz, 1H), 7.32 (dd, J=7.8 Hz, J=7.2 Hz, 1H), 7.08 (m, 1H), 6.89 (m, 1H), 3.76 (s, 3H), 3.70-3.68 (m, 1H), 2.63-2.59 (m, 1H), 1.86-1.83 (m, 1H), 1.80-1.76 (m, 2H), 1.51-1.44 (m, 1H), 1.33-1.24 (m, 4H).

Example 43

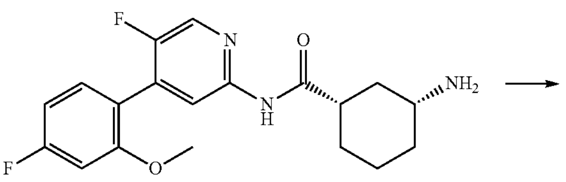

5b

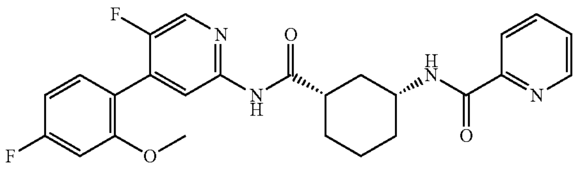

43

Synthesis of Compound 43

5b (0.11 g, 0.30 mmol) and 2-pyridinecarboxylic acid (0.04 g, 0.33 mmol) were dissolved in N,N-dimethylformamide (15 mL), and 2-(7-azabenzotriazol-1-yl)-N,N,N',N'-tetramethyluronium hexafluorophosphate (0.14 g, 0.36 mmol) and N,N-diisopropylethylamine (0.08 g, 0.6 mmol) were added. The reaction mixture was reacted at room temperature for 8 hours until no starting material was detected by TLC. To the reaction solution was added water (30 mL). A solid was precipitated and filtered to give the final product 43 (0.07 g, 50%).

MS m/z (ESI): 467.2 [M+H]$^+$.

$^1$H NMR (600 MHz, DMSO-$d_6$) δ 10.63 (s, 1H), 8.63-8.62 (m, 2H), 8.31 (s, 1H), 8.07 (d, J=5.4 Hz, 1H), 8.01 (d, J=7.8 Hz, 1H), 7.98-7.95 (m, 1H), 7.58-7.56 (m, 1H), 7.34-7.31 (m, 1H), 7.09-7.07 (m, 1H), 6.91-6.88 (m, 1H), 3.89-3.87 (m, 1H), 3.77 (s, 3H), 2.71-2.63 (m, 1H), 1.92-1.91 (m, 1H), 1.82-1.77 (m, 3H), 1.61-1.55 (m, 1H), 1.45-1.28 (m, 3H).

Example 44

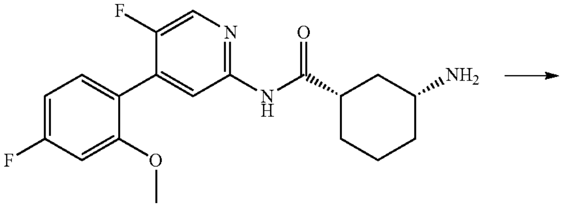

5b

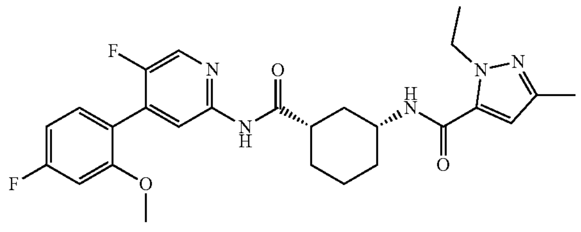

44

Synthesis of Final Product Compound 44

5b (188 mg, 0.52 mmol) and 1-ethyl-3-methyl-1H-pyrazole-4-carboxylic acid (161 mg, 1.04 mmol) were dissolved in N,N-dimethylformamide (5 mL). 2-(7-azabenzotriazol-1-yl)-N,N,N',N'-tetramethyluronium hexafluorophosphate (395 mg, 1.04 mmol) and diisopropylethylamine (0.26 mL, 1.56 mmol) were successively added. The reaction mixture was reacted at room temperature for 15 hours until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=4:1-2:1) to give the final product 44 (230 mg, yield 88%).

MS m/z (ESI): 498.2 [M+H]$^+$.

$^1$H NMR (600 MHz, DMSO-$d_6$) δ 10.63 (s, 1H), 8.34 (s, 1H), 8.22 (d, J=8.4 Hz, 1H), 8.09 (d, J=6.0 Hz, 1H), 7.35 (m, 1H), 7.11 (m, 1H), 6.92 (m, 1H), 6.59 (s, 1H), 4.38 (dd, J=7.2 Hz, J=3.0 Hz, 2H), 3.79 (s, 4H), 2.15 (s, 3H), 2.00 (d, J=11.4 Hz, 1H), 1.84-1.80 (m, 4H), 1.49-1.46 (m, 2H), δ 1.32-1.30 (m, 5H).

Example 45

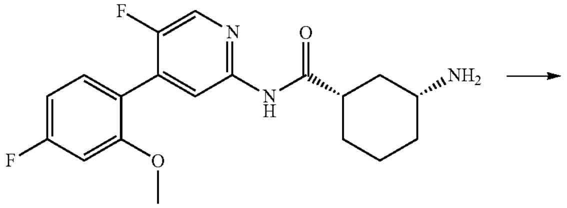

5b

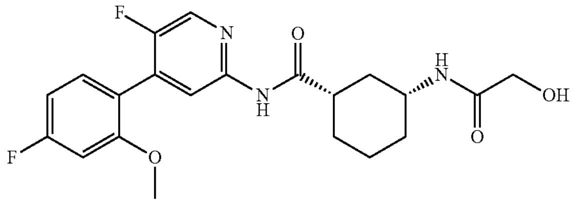

45

Synthesis of Final Product 45

5b (50 mg, 0.138 mmol) was dissolved in N,N-dimethylformamide (5 mL), and then hydroxylacetic acid (16 mg, 0.21 mmol), 2-(7-azabenzotriazol-1-yl)-N,N,N',N'-tetramethyluronium hexafluorophosphate (80 mg, 0.21 mmol) and N,N-diisopropylethylamine (69 μL, 0.42 mmol) were added. The reaction mixture was stirred and reacted at room temperature for 10 hours until no starting material was detected by TLC. To the reaction solution was added water (50 mL).

The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane: methanol=40:1-20:1) to give the final product 45 (30 mg, yield 52%).

MS m/z (ESI): 420.2[M+H]$^+$.

$^1$H NMR (600 MHz, DMSO-$d_6$) δ 10.56 (s, 1H), 8.31 (s, 1H), 8.06 (d, J=5.4 Hz, 1H), 7.56 (d, J=9.0 Hz, 1H), 7.34-7.31 (m, 1H), 7.09-7.07 (m, 1H), 6.91-6.88 (m, 1H), 5.38-5.36 (m, 1H), 3.77-3.75 (m, 5H), 3.66-3.63 (m, 1H), 2.61-2.57 (m, 1H), 1.83-1.68 (m, 4H), 1.34-1.26 (m, 4H).

Example 46

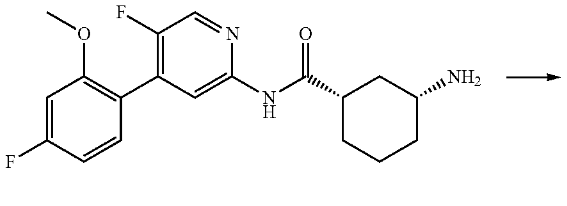

5b

-continued

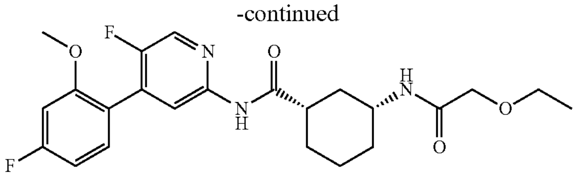

46

Synthesis of Final Product 46

5b (0.20 g, 0.55 mmol) was dissolved in N,N-dimethylformamide (30 mL), and then ethoxyacetic acid (68 mg, 0.65 mmol), 2-(7-azabenzotriazol-1-yl)-N,N,N',N'-tetramethyluronium hexafluorophosphate (178 mg, 0.47 mmol) and N,N-diisopropylethylamine (111 mg, 0.86 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-20:1) to give the final product 46 (96 mg, yield 39%).

MS m/z (ESI): 448.2 $[M+H]^+$.

$^1$H NMR (600 MHz, DMSO-$d_6$) δ 10.58 (s, 1H), 8.33 (s, 1H), 8.07 (d, J=5.4 Hz, 1H), 7.59 (d, J=8.4 Hz, 1H), 7.35-7.33 (m, 1H), 7.11-7.09 (m, 1H), 6.93-6.90 (m, 1H), 3.78-3.76 (m, 5H), 3.69-3.67 (m, 1H), 3.47-3.44 (m, 2H), 2.63-2.61 (m, 1H), 1.84-1.69 (m, 4H), 1.47-1.43 (m, 1H), 1.30-1.28 (m, 6H).

Example 47

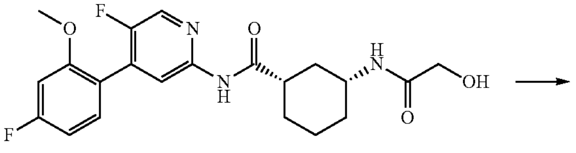

45

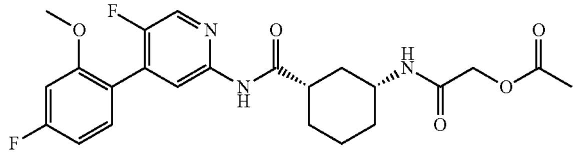

47

Synthesis of Final Product 47

45 (0.20 g, 0.48 mmol) was dissolved in dichloromethane (30 mL), and then acetyl chloride (45 mg, 0.57 mmol) and triethylamine (97 mg, 0.96 mmol) were added. The reaction mixture was stirred at room temperature for 1.5 hours until no starting material was detected by TLC. The solvent was removed under reduced pressure. The crude product was purified by column chromatography (dichloromethane: methanol=50:1-20:1) to give the final product 47 (100 mg, yield 45%).

MS m/z (ESI): 462.2 $[M+H]^+$.

$^1$H NMR (600 MHz, DMSO-$d_6$) δ 10.58 (s, 1H), 8.33 (s, 1H), 8.07 (d, J=5.4 Hz, 1H), 7.59 (d, J=8.4 Hz, 1H), 7.35-7.34 (m, 1H), 7.33-7.11 (m, 1H), 7.09-6.90 (m, 1H), 4.39 (s, 2H), 3.78 (s, 3H), 3.65-3.63 (m, 1H), 2.66-2.60 (m, 1H), 2.58 (s, 3H), 1.85-1.84 (m, 1H), 1.75-1.69 (m, 3H), 1.39-1.24 (m, 3H), 1.16-1.14 (m, 1H).

Example 48

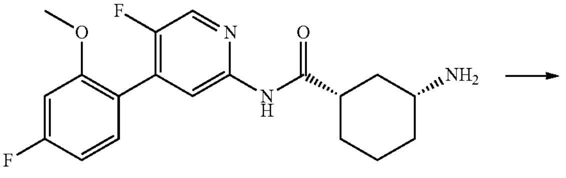

5b

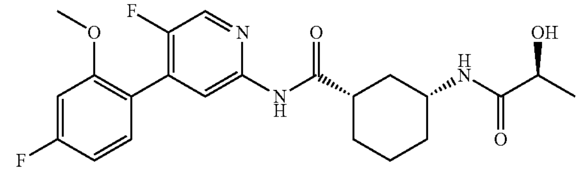

48

Synthesis of Final Product 48

5b (0.20 g, 0.55 mmol) was dissolved in N,N-dimethylformamide (30 mL), and then L-lactic acid (58.5 mg, 0.65 mmol), 2-(7-azabenzotriazol-1-yl)-N,N,N',N'-tetramethyluronium hexafluorophosphate (178 mg, 0.47 mmol) and N,N-diisopropylethylamine (111 mg, 0.86 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride (50 mL×2), and dried over anhydrous sodium sulfate. Then the solvent was removed under reduced pressure. The crude product was purified by column chromatography (dichloromethane:methanol=50:1-20:1) to give the final product 48 (96 mg, yield 40%).

MS m/z (ESI): 434.2 $[M+H]^+$.

$^1$H NMR (600 MHz, DMSO-$d_6$) δ 10.57 (s, 1H), 8.31 (s, 1H), 8.05 (d, J=6 Hz, 1H), 7.51 (d, J=8.4 Hz, 1H), 7.34-7.31 (m, 1H), 7.10-7.07 (m, 1H), 6.91-6.88 (m, 1H), 5.38 (d, J=5.4 Hz, 1H), 3.92-3.88 (m, 1H), 3.77 (s, 3H), 3.62-3.59 (m, 1H), 2.60-2.56 (m, 1H), 1.83-1.81 (m, 1H), 1.77-1.72 (m, 2H), 1.41-1.35 (m, 1H), 1.31-1.26 (m, 4H), 1.23 (d, J=13.2 Hz, 3H).

Example 49

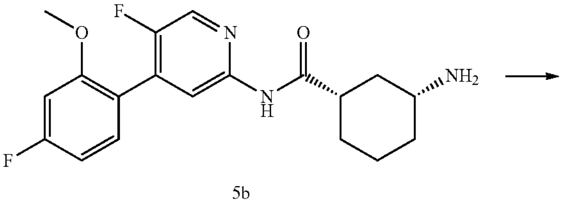

5b

-continued

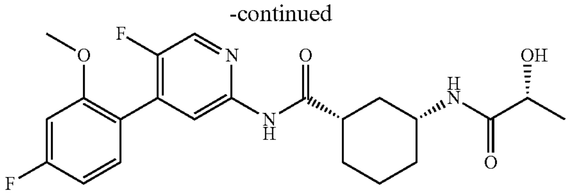

49

Synthesis of Final Product 49

5b (0.20 g, 0.55 mmol) was dissolved in N,N-dimethylformamide (30 mL), and then D-lactic acid (58.5 mg, 0.65 mmol), 2-(7-azabenzotriazol-1-yl)-N,N,N',N'-tetramethyluronium hexafluorophosphate (178 mg, 0.47 mmol) and N,N-diisopropylethylamine (111 mg, 0.86 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-20:1) to give the final product 49 (100 mg, yield 42%).

MS m/z (ESI): 434.2 $[M+H]^+$.

$^1$H NMR (600 MHz, DMSO-$d_6$) δ 10.57 (s, 1H), 8.30 (s, 1H), 8.05 (d, J=4.8 Hz, 1H), 7.51 (d, J=7.8 Hz, 1H), 7.33 (t, J=7.8 Hz, 1H), 7.08 (d, J=11.4 Hz, 1H), 6.89 (t, J=7.8 Hz, 1H), 5.38 (d, J=5.4 Hz, 1H), 3.92-3.88 (m, 1H), 3.77 (s, 3H), 3.62-3.59 (m, 1H), 2.60-2.56 (m, 1H), 1.81 (d, J=12 Hz, 1H), 1.77-1.72 (m, 2H), 1.67 (d, J=11.4 Hz, 1H), 1.41-1.35 (m, 1H), 1.31-1.25 (m, 4H), 1.23 (s, 3H).

Example 50

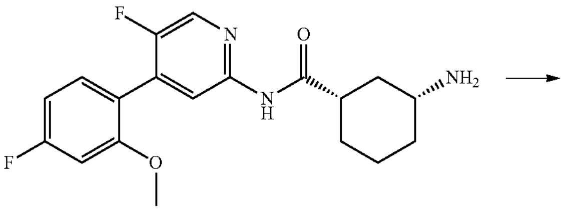

5b

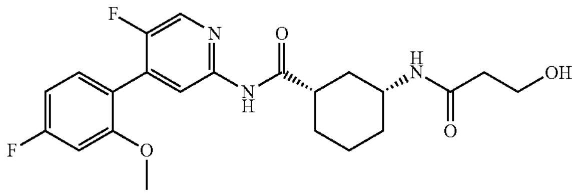

50

Synthesis of Final Product 50

5b (50 mg, 0.138 mmol) was dissolved in N,N-dimethylformamide (5 mL) and then 3-hydroxylpropionic acid (19 mg, 0.21 mmol), 2-(7-azabenzotriazol-1-yl)-N,N,N',N'-tetramethyluronium hexafluorophosphate (79 mg, 0.21 mmol) and N,N-diisopropylethylamine (69 μL, 0.42 mmol) were added. The reaction mixture was stirred and reacted at room temperature for 10 hours until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=40:1-20:1) to give the final product 50 (32 mg, yield 53%).

MS m/z (ESI): 434.2$[M+H]^+$.

$^1$H NMR (600 MHz, DMSO-$d_6$) δ 10.56 (s, 1H), 8.31 (s, 1H), 8.06-8.05 (d, J=5.4 Hz, 1H), 7.57-7.55 (d, J=9.0 Hz, 1H), 7.34-7.31 (m, 1H), 7.09-7.07 (m, 1H), 6.91-6.88 (m, 1H), 5.38-5.36 (t, J=5.4 Hz, 1H), 3.77-3.75 (m, 5H), 3.66-3.63 (m, 1H), 2.61-2.56 (m, 3H), 1.83-1.68 (m, 4H), 1.34-1.26 (m, 4H).

Example 51

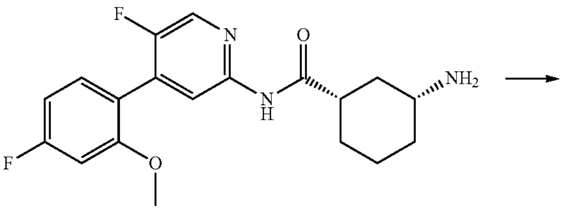

5b

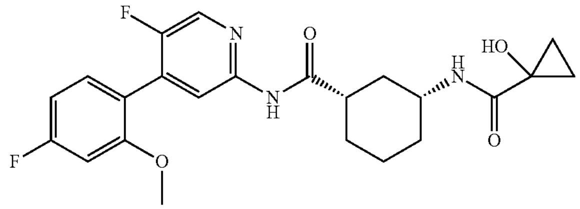

51

Synthesis of Final Product 51

5b (50 mg, 0.138 mmol) was dissolved in N,N-dimethylformamide (5 mL) and then 1-hydroxycyclopropane carboxylic acid (21 mg, 0.21 mmol), 2-(7-azabenzotriazol-1-yl)-N,N,N',N'-tetramethyluronium hexafluorophosphate (79 mg, 0.21 mmol) and N,N-diisopropylethylamine (69 μL, 0.42 mmol) were added. The reaction mixture was stirred and reacted at room temperature for 10 hours until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=40:1-20:1) to give the final product 51 (36 mg, yield 59%).

MS m/z (ESI): 446.2$[M+H]^+$.

$^1$H NMR (600 MHz, DMSO-$d_6$) δ 10.61 (s, 1H), 8.34 (s, 1H), 8.09-8.08 (m, 1H), 7.73-7.71 (m, 1H), 7.37-7.34 (m, 1H), 7.13-7.10 (m, 1H), 6.95-6.91 (m, 1H), 3.80 (s, 3H), 2.61-2.55 (m, 2H), 1.85-1.72 (m, 4H), 1.50-1.47 (m, 1H), 1.32-1.30 (m, 3H), 1.00-0.98 (m, 2H), 0.81-0.80 (m, 2H).

Example 52

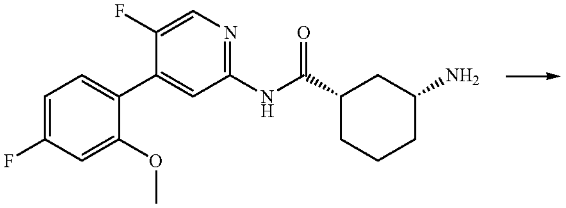

5b

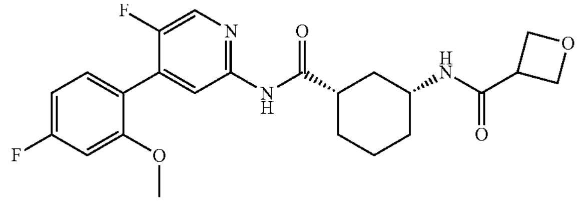

52

Synthesis of Final Product 52

5b (50 mg, 0.138 mmol) was dissolved in N,N-dimethylformamide (5 mL) and then 3-oxetanecarboxylic acid (21 mg, 0.21 mmol), 2-(7-azabenzotriazol-1-yl)-N,N,N',N'-tetramethyluronium hexafluorophosphate (79 mg, 0.21 mmol) and N,N-diisopropylethylamine (69 μL, 0.42 mmol) were added. The reaction mixture was stirred and reacted at room temperature for 10 hours until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=40:1-20:1) to give the final product 52 (36 mg, yield 59%).

MS m/z (ESI): 446.2$[M+H]^+$.

$^1H$ NMR (600 MHz, DMSO-$d_6$) δ 10.59 (s, 1H), 8.33 (s, 1H), 8.07-8.06 (m, 1H), 7.98-7.97 (m, 1H), 7.35-7.32 (m, 1H), 7.10-7.08 (m, 1H), 6.93-6.91 (m, 1H), 4.61-4.56 (m, 2H), 3.78 (s, 3H), 3.69-3.67 (m, 2H), 3.42-3.40 (m, 1H), 2.69-2.55 (m, 2H), 1.89-1.87 (m, 1H), 1.77-1.75 (m, 3H), 1.29-1.25 (m, 3H), 1.18-1.09 (m, 1H).

Example 53

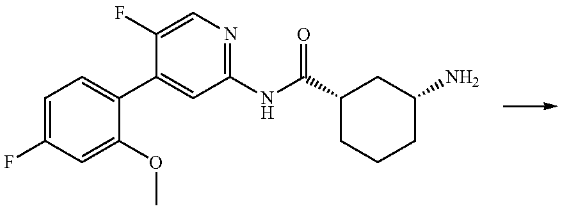

5b

-continued

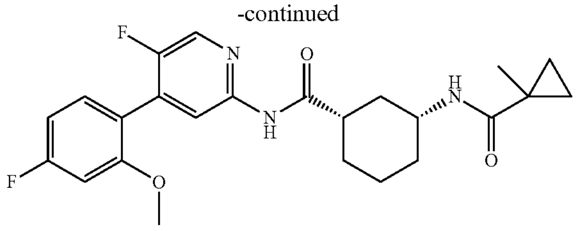

53

Synthesis of Final Product 53

5b (50 mg, 0.138 mmol) was dissolved in N,N-dimethylformamide (5 mL) and then 1-methylcyclopropane-1-carboxylic acid (21 mg, 0.21 mmol), 2-(7-azabenzotriazol-1-yl)-N,N,N',N'-tetramethyluronium hexafluorophosphate (79 mg, 0.21 mmol) and N,N-diisopropylethylamine (69 μL, 0.42 mmol) were added. The reaction mixture was stirred and reacted at room temperature for 10 hours until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=40:1-20:1) to give the final product 53 (40 mg, yield 65%).

MS m/z (ESI): 444.2$[M+H]^+$.

$^1H$ NMR (600 MHz, DMSO-$d_6$) δ 10.57 (s, 1H), 8.32 (s, 1H), 8.08-8.06 (m, 1H), 7.34-7.32 (m, 1H), 7.24-7.22 (m, 1H), 7.11-7.09 (m, 1H), 6.93-6.91 (m, 1H), 3.78 (s, 3H), 3.66-3.58 (m, 1H), 2.59-2.50 (m, 1H), 1.80-1.69 (m, 4H), 1.47-1.44 (m, 1H), 1.30-1.22 (m, 6H), 0.92-0.90 (m, 2H), 0.46-0.44 (m, 2H).

Example 54

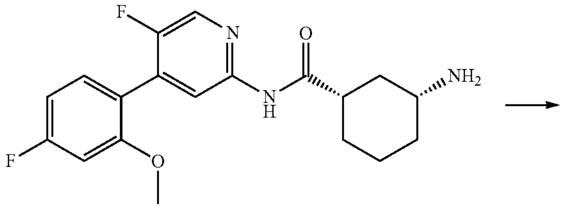

5b

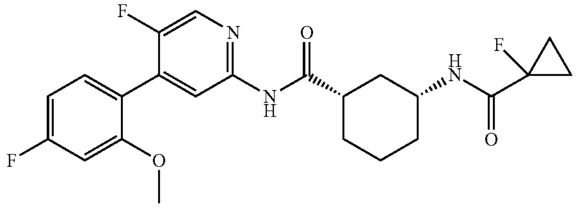

54

Synthesis of Final Product 54

5b (50 mg, 0.138 mmol) was dissolved in N,N-dimethylformamide (5 mL) and then 1-fluorocyclopropanecarboxylic acid (22 mg, 0.21 mmol), 2-(7-azabenzotriazol-1-yl)-N,N,N',N'-tetramethyluronium hexafluorophosphate (79 mg, 0.21 mmol) and N,N-diisopropylethylamine (69 μL, 0.42 mmol) were added. The reaction mixture was stirred and reacted at room temperature for 10 hours until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=40:1-20:1) to give the final product 54 (37 mg, yield 60%).

MS m/z (ESI): 448.2[M+H]$^+$.

$^1$H NMR (600 MHz, $CDCl_3$) δ 8.23-8.20 (m, 1H), 8.13 (s, 1H), 7.86 (s, 1H), 7.27-7.25 (m, 1H), 6.80-6.70 (m, 2H), 6.40- 6.25 (m, 1H), 4.00-3.85 (m, 1H), 3.82 (s, 3H), 2.50-2.40 (m, 1H), 2.35-2.25 (m, 1H), 2.10-1.90 (m, 3H), 1.55-1.45 (m, 3H), 1.40-1.30 (m, 2H), 1.25-1.15 (m, 3H).

Example 55

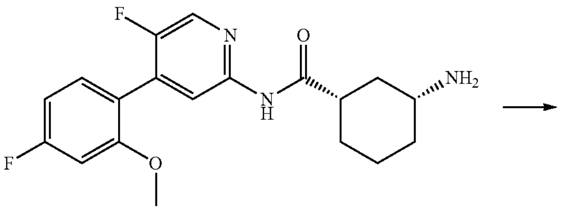

5b

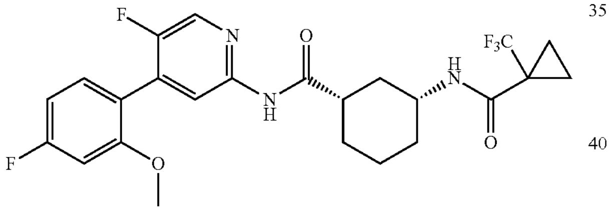

55

Synthesis of Final Product 55

5b (50 mg, 0.138 mmol) was dissolved in N,N-dimethylformamide (5 mL) and then 1-trifluoromethylcyclopropane-1-carboxylic acid (32 mg, 0.21 mmol), 2-(7-azabenzotriazol-1-yl)-N,N,N',N'-tetramethyluronium hexafluorophosphate (79 mg, 0.21 mmol) and N,N-diisopropylethylamine (69 μL, 0.42 mmol) were added. The reaction mixture was stirred and reacted at room temperature for 10 hours until no starting material was detected by TLC. To the reaction solution was added water (50 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=40:1-20:1) to give the final product 55 (45 mg, yield 65%).

MS m/z (ESI): 498.2[M+H]$^+$.

$^1$H NMR (600 MHz, $CDCl_3$) δ 8.23-8.20 (m, 1H), 8.13 (s, 1H), 7.86 (s, 1H), 7.27-7.25 (m, 1H), 6.79-6.69 (m, 2H), 6.05- 5.95 (m, 1H), 4.00-3.86 (m, 1H), 3.82 (s, 3H), 2.50-2.35 (m, 1H), 2.30-2.20 (m, 1H), 2.05-1.90 (m, 3H), 1.56-1.35 (m, 5H), 1.21-1.15 (m, 3H).

Example 56

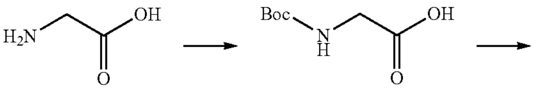

56a

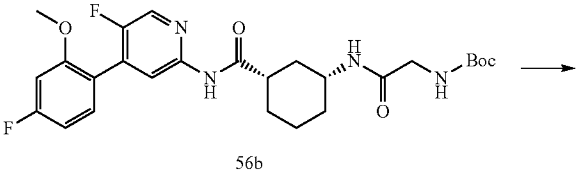

56b

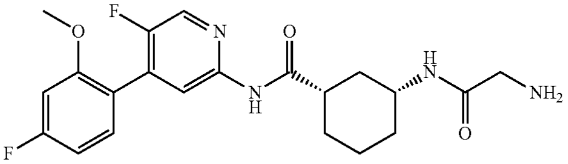

56

Synthesis of Intermediate 56a

Glycine (500 mg, 6.70 mmol) was dissolved in dioxane (10 mL) and water (10 mL), and triethylamine (1.40 g, 14.40 mmol) and di-tert-butyl dicarbonate (1.74 g, 8.00 mmol) were added. The reaction mixture was reacted at room temperature overnight. The starting material was completely converted, as monitored by TLC. The mixture was concentrated. An aqueous sodium carbonate solution (100 mL) was added. The mixture was washed with ethyl acetate (100 mL×3). The aqueous phase was adjusted with a diluted hydrochloric acid to the pH of 3 and extracted with ethyl acetate (100 mL×3). The organic phases were combined, dried over anhydrous sodium sulfate, and filtered. The filtrate was concentrated to give 56a (1.00 g, yield 85%).

Synthesis of Intermediate 56b 56a (46 mg, 0.26 mmol) was dissolved in N,N-dimethylformamide (3 mL), and 2-(7-azabenzotriazol-1-yl)-N,N,N',N'-tetramethyluronium hexafluorophosphate (125 mg, 0.33 mmol) and diisopropylethylamine (57 mg, 0.44 mmol) were added. The reaction mixture was stirred for 10 minutes, and then 5b (78 mg, 0.22 mmol) was added. The reaction mixture was reacted at room temperature overnight. The starting material was completely converted, as monitored by TLC. To the reaction mixture was added water (100 mL). The mixture was extracted with ethyl acetate (100 mL×3). The organic phases were combined, washed with a saturated saline solution (50 mL×3), dried over anhydrous sodium sulfate, and filtered. The filtrate was concentrated. The crude product was purified by thin-layer chromatography (dichloromethane:methanol=10:1) to give 56b (80 mg, yield 70%).

Synthesis of Final Product 56

56b (80 mg, 0.22 mmol) was dissolved in dichloromethane (4 mL), and trifluoroacetic acid (1 mL) was added. The reaction mixture was reacted at room temperature for 2 hours until the starting material was completely converted, as monitored by TLC. The reaction mixture was concentrated. The crude product was purified by the thin layer chromatography (dichloromethane:methanol=10:1) to give the final product 56 (40 mg, yield 43%).

MS m/z(ESI): 419.2 $[M+H]^+$.

$^1H$ NMR (600 MHz, DMSO-$d_6$) δ 10.59 (s, 1H), 8.31 (s, 1H), 8.05 (d, J=6.0 Hz, 1H), 7.94 (br, 2H), 7.32-7.30 (m, 1H), 7.09-7.07 (m, 1H), 6.91-6.88 (m, 1H), 3.76 (s, 3H), 3.64-3.59 (m, 1H), 3.15 (d, J=4.8 Hz, 2H), 2.62-2.59 (m, 1H), 1.89-1.87 (m, 1H), 1.79-1.77 (m, 3H), 1.34-1.28 (m, 3H), 1.18-1.10 (m, 1H).

Example 57

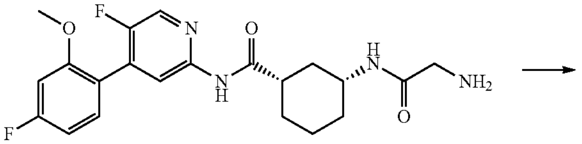

56

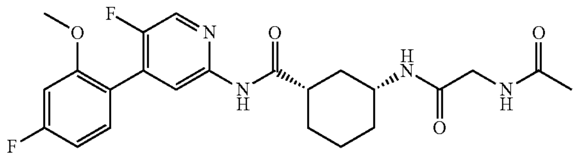

57

Synthesis of Final Product 57

The compound 56 (205 mg, 0.49 mmol) was dissolved in dichloromethane (35 mL), and then acetic anhydride (149 mg, 1.47 mmol) and triethylamine (148 mg, 1.47 mmol) were added. The reaction mixture was stirred at room temperature for 4 hours until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=10:1-2:1) to give the final product 57 (138 mg, yield 61%).

MS m/z (ESI): 461.2 $[M+H]^+$.

$^1H$ NMR (600 MHz, DMSO-$d_6$) δ 10.60 (s, 1H), 8.33 (s, 1H), 8.07 (d, J=6.0 Hz, 1H), 7.95-7.92 (m, 2H), 7.35-7.33 (m, 1H), 7.11 (d, J=1.8 Hz, 1H), 6.93-6.90 (m, 1H), 4.09 (s, 2H), 3.79 (s, 3H), 3.58-3.56 (m, 1H), 2.59-2.50 (m, 1H), 1.86-1.73 (m, 4H), 1.83 (s, 3H), 1.39-1.14 (m, 4H).

Example 58

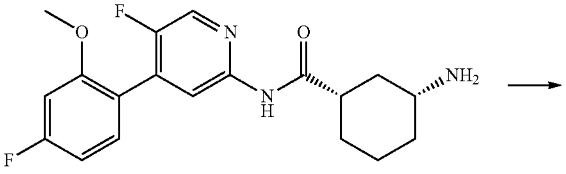

5b

-continued

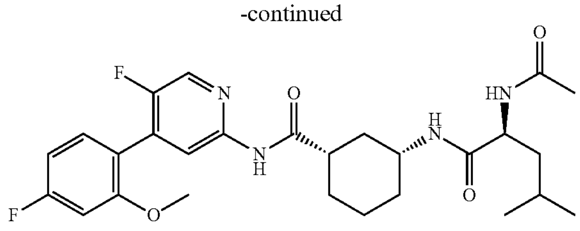

58

Synthesis of Final Product 58

5b (0.20 g, 0.55 mmol) was dissolved in N,N-dimethylformamide (30 mL), and then N-acetyl-L-leucine (112 mg, 0.65 mmol), 2-(7-azabenzotriazol-1-yl)-N,N,N',N'-tetramethyluronium hexafluorophosphate (178 mg, 0.47 mmol) and N,N-diisopropylethylamine (111 mg, 0.86 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-20:1) to give the final product 58 (190 mg, yield 67%).

MS m/z (ESI): 517.2 $[M+H]^+$.

$^1H$ NMR (600 MHz, DMSO-$d_6$) δ 10.60 (s, 1H), 8.33 (s, 1H), 8.07 (d, J=6.0 Hz, 1H), 7.94 (dd, J=10.2, Hz, J=8.4 Hz, 2H), 7.35(dd, J=7.8 Hz, J=7.2 Hz, 1H), 7.11-7.10 (m, 1H), 6.93-6.90 (m, 1H), 4.24-4.23 (m, 1H), 3.79 (s, 3H), 3.58-3.56 (m, 1H), 2.59-2.50 (m, 1H), 1.83-1.71 (m, 7H), 1.53-1.51 (m, 1H), 1.38-1.36 (m, 2H), 1.31-1.28 (m, 6H), 0.91 (m, 6H).

Example 59

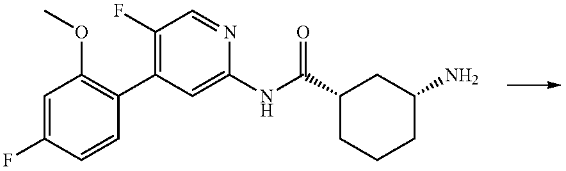

5b

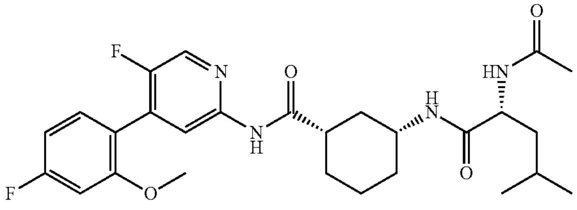

59

Synthesis of Final Product 59

5b (200 mg, 0.55 mmol) was dissolved in N,N-dimethylformamide (30 mL), and then N-acetyl-D-leucine (112 mg, 0.65 mmol), 2-(7-azabenzotriazol-1-yl)-N,N,N',N'-tetramethyluronium hexafluorophosphate (178 mg, 0.47 mmol) and N,N-diisopropylethylamine (111 mg, 0.86 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane: methanol=50:1-20:1) to give the final product 59 (181 mg, yield 64%).

MS m/z (ESI): 517.2 $[M+H]^+$.

$^1H$ NMR (600 MHz, DMSO-$d_6$) δ 10.59 (s, 1H), 8.33 (s, 1H), 8.07 (d, J=6.0 Hz, 1H), 7.93 (dd, J=10.2, Hz, J=8.4 Hz, 2H), 7.34 (dd, J=7.8 Hz, J=7.2 Hz, 1H), 7.11-7.10 (m, 1H), 6.92-6.89 (m, 1H), 4.24-4.23 (m, 1H), 3.80 (s, 3H), 3.57-3.55 (m, 1H), 2.59-2.50 (m, 1H), 1.83-1.71 (m, 7H), 1.53-1.51 (m, 1H), 1.38-1.36 (m, 2H), 1.30-1.27 (m, 6H), 0.91 (m, 6H).

Example 60

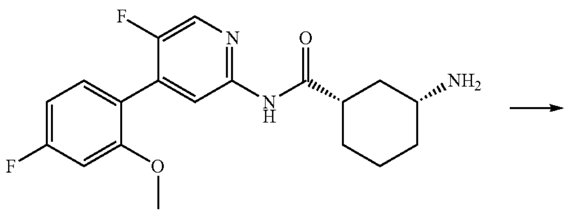

5b

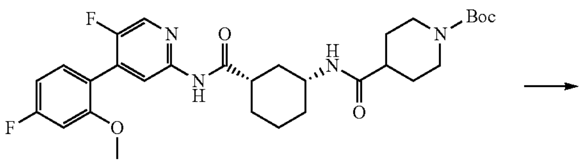

60a

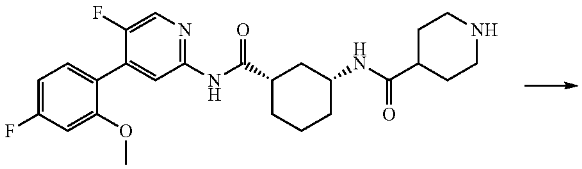

60b

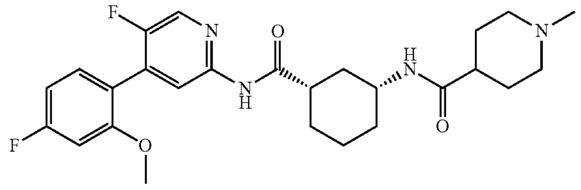

60

Synthesis of Intermediate 60a 5b (500 mg, 1.385 mmol) was dissolved in N,N-dimethylformamide (15 mL), and then 1-Boc-4-piperidinecarboxylic acid (380 mg, 1.66 mmol), 2-(7-azabenzotriazol-1-yl)-N,N,N',N'-tetramethyluronium hexafluorophosphate (787 mg, 2.07 mmol) and N,N-diisopropylethylamine (687 uL, 4.15 mmol) were added. The reaction mixture was stirred and reacted at room temperature for 10 hours until no starting material was detected by TLC. To the reaction solution was added water (50 mL). The mixture was stirred for 30 minutes, filtered, and dried over anhydrous sodium sulfate. Then the solvent was removed under reduced pressure to give 60a (623 mg, yield 79%).

Synthesis of Intermediate 60b 60a (623 mg, 1.09 mmol) was dissolved in dichloromethane (20 mL), and then trifluoroacetic acid (5 mL) was added. The reaction mixture was stirred at room temperature for 2 hours until no starting material was detected by TLC. To the reaction solution was added water (100 mL). The mixture was adjusted with sodium bicarbonate to a pH of 8 and extracted with ethyl acetate (50 mL×3). The organic phases were combined, washed with saturated sodium chloride solution (50 mL×2), and dried over anhydrous sodium sulfate. Then the solvent was removed under reduced pressure to give 60b (500 mg, yield 97%).

Synthesis of Final Product 60

60b (300 mg, 0.63 mmol) was dissolved in methanol (10 mL), and then an aqueous formaldehyde solution (1 mL), sodium triacetoxyborohydride (269 mg, 1.27 mmol), and one drop of acetic acid were added. The reaction mixture was stirred and reacted at room temperature for 10 hours until no starting material was detected by TLC. To the reaction solution was added water (50 mL). The mixture was adjusted with sodium bicarbonate to a pH of 8 and extracted with ethyl acetate (50 mL×3). The organic phases were combined, washed with saturated sodium chloride solution (50 mL×2), and dried over anhydrous sodium sulfate. The solvent was removed under reduced pressure to give the final product 60 (214 mg, yield 70%).

MS m/z (ESI): 487.2$[M+H]^+$.

$^1H$ NMR (600 MHz, DMSO-$d_6$) δ 10.59 (s, 1H), 8.34 (s, 1H), 8.08 (d, J=4.8 Hz, 1H), 7.68 (d, J=7.8 Hz, 1H), 7.35 (d, J=7.8 Hz, 1H), 7.11 (d, J=11.4 Hz, 1H), 6.93 (d, J=8.4 Hz, 1H), 3.79 (s, 3H), 3.58-3.56 (m, 1H), 2.76-2.74 (m, 2H), 2.62-2.58 (m, 1H), 2.51 (s, 3H), 1.99-1.96 (m, 1H), 1.86-1.84 (m, 1H), 1.81-1.72 (m, 5H), 1.57-1.53 (m, 4H), 1.31-1.24 (m, 3H), 1.18-1.08 (m, 1H).

Example 61

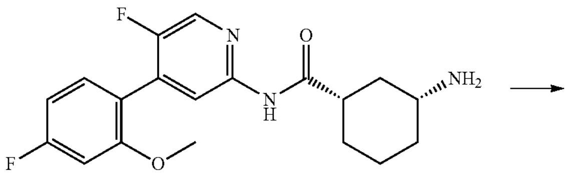

5b

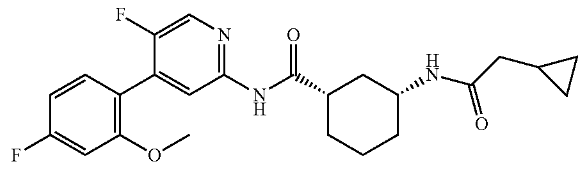

61

Synthesis of Final Product 61

5b (0.07 g, 0.19 mmol) was dissolved in N,N-dimethylformamide (10 mL), and cyclopropylacetic acid (0.02 g, 0.21 mmol), 2-(7-azabenzotriazol-1-yl)-N,N,N',N'-tetramethyluronium hexafluorophosphate (0.09 g, 0.23 mmol) and N,N-diisopropylethylamine (0.05 g, 0.38 mmol) were added. The reaction mixture was reacted at room temperature for 8 hours until no starting material was detected by TLC. To the reaction solution was added water (20 mL). The mixture was extracted with ethyl acetate (15 mL×3). The organic phases were combined and dried over anhydrous sodium sulfate. The mixture was concentrated under reduced pressure, and the crude product was purified by column chromatography (dichloromethane:methanol=20:1) to give the final product 61 (0.04 g, yield 47%).

MS m/z (ESI): 444.2 $[M+H]^+$.

$^1$H NMR (600 MHz, DMSO-$d_6$) δ 10.58 (s, 1H), δ 8.33 (s, 1H), 8.07 (d, J=5.4 Hz, 1H), 7.63 (d, J=8.4 Hz, 1H), 7.35-7.33 (m, 1H), 7.11-7.01 (m, 1H), 6.93-6.90 (m, 1H), 3.79 (s, 3H), 3.60-3.57 (m, 1H), 2.60-2.61 (m, 1H), 1.94-1.93 (m, 2H), 1.88-1.75 (m, 4H), 1.32-1.23 (m, 4H), 1.10-1.08 (m, 1H), 0.54-0.45 (m, 2H), 0.19-0.15 (m, 2H).

Example 62

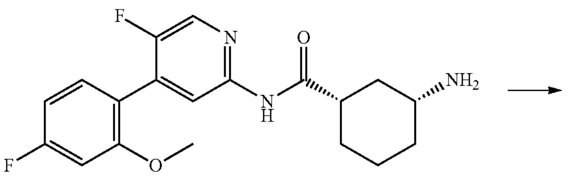

5b

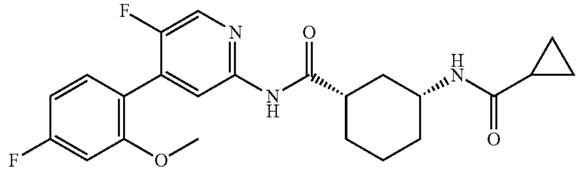

62

Synthesis of Final Product 62

5b (0.07 g, 0.19 mmol) was dissolved in dichloromethane (20 mL), and cyclopropylcarboxylic acid (0.02 g, 0.21 mmol), 1-(3-dimethylaminopropyl)-3-ethylcarbodiimide hydrochloride (0.07 g, 0.38 mmol) and 4-dimethylaminopyridine (2.3 mg, 0.019 mmol) were added. The reaction mixture was reacted at room temperature for 8 hours until no starting material was detected by TLC. The reaction solution was successively washed with water and an aqueous sodium bicarbonate solution and dried over anhydrous sodium sulfate. The organic phase was directly purified by column chromatography (dichloromethane:methanol=50:1) to give the final product 62 (0.04 g, yield 48%).

MS m/z (ESI): 430.2 $[M+H]^+$.

$^1$H NMR (600 MHz, DMSO-$d_6$) δ 10.58 (s, 1H), 8.32 (s, 1H), 8.08 (d, J=5.4 Hz, 1H), 7.99 (d, J=8.4 Hz, 1H), 7.36-7.33 (m, 1H), 7.11-7.09 (m, 1H), 6.93-6.90 (m, 1H), 3.79 (s, 3H), 3.60-3.58 (m, 1H), 2.59-2.50 (m, 1H), 1.89-1.77 (m, 4H), 1.50-1.47 (m, 1H), 1.34-1.26 (m, 3H), 1.10-1.08 (m, 1H), 0.64-0.60 (m, 4H).

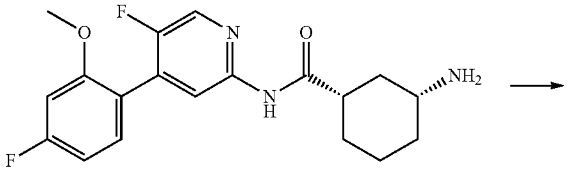

5b

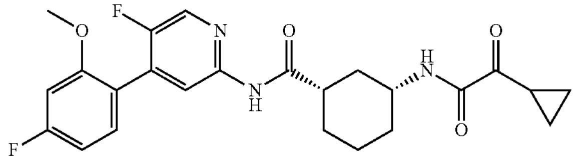

63

Synthesis of Final Product 63

5b (0.10 g, 0.28 mmol) was dissolved in N,N-dimethylformamide (25 mL), and then 2-cyclopropyl-2-carbonylacetic acid (35 mg, 0.31 mmol), 2-(7-azabenzotriazol-1-yl)-N,N,N',N'-tetramethyluronium hexafluorophosphate (118 mg, 0.31 mmol) and N,N-diisopropylethylamine (0.07 g, 0.55 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=100:1-40:1) to give the final product 63 (54 mg, yield 43%).

MS m/z (ESI): 458.1 $[M+H]^+$.

$^1$H NMR (600 MHz, $CDCl_3$) δ 8.55 (s, 1H), 8.32 (d, J=6.0 Hz, 1H), 8.11 (s, 1H), 7.28-7.25 (m, 1H), 6.94 (d, J=8.4 Hz, 1H), 6.77-6.71 (m, 2H), 3.86-3.82 (m, 1H), 3.81 (s, 3H), 3.10-3.08 (m, 1H), 2.48-2.46 (m, 1H), 2.25 (d, J=12.0 Hz, 1H), 2.04-1.95 (m, 3H), 1.53-1.47 (m, 3H), 1.26-1.24 (m, 1H), 1.18-1.15 (m, 4H).

Example 64

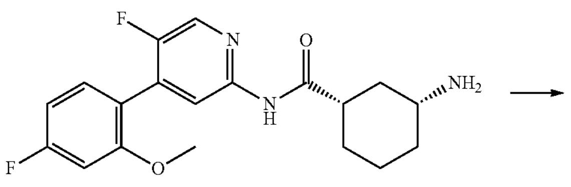

5b

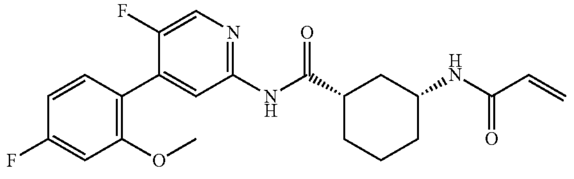

64

Synthesis of Final Product 64

5b (0.16 g, 0.44 mmol) was dissolved in dichloromethane (20 mL), and triethylamine (0.05 g, 0.53 mmol) was added. Acryloyl chloride (0.05 g, 0.53 mmol) was added in an ice bath. The reaction mixture was reacted at room temperature for 4 hours until no starting material was detected by TLC. To the reaction solution was added water (30 mL). The mixture was extracted with dichloromethane (20 mL×3). The organic phases were combined and dried over anhydrous sodium sulfate. The mixture was concentrated under reduced pressure. The crude product was purified by column chromatography (dichloromethane:methanol=50:1) to give the final product 64 (0.10 g, yield 55%).

MS m/z (ESI): 416.2 $[M+H]^+$.

$^1H$ NMR (600 MHz, DMSO-$d_6$) δ 10.59 (s, 1H), 8.31 (s, 1H), 8.06 (d, J=6.0 Hz, 1H), 8.02 (d, J=7.8 Hz, 1H), 7.34-7.31 (m, 1H), 7.10-7.07 (m, 1H), 6.91-6.89 (m, 1H), 6.18-6.14 (m, 1H), 6.06-6.03 (m, 1H), 5.55-5.53 (m, 1H), 3.77 (s, 3H), 3.65-3.63 (m, 1H), 2.61-2.60 (m, 1H), 1.90-1.77 (m, 4H), 1.34-1.08 (m, 4H).

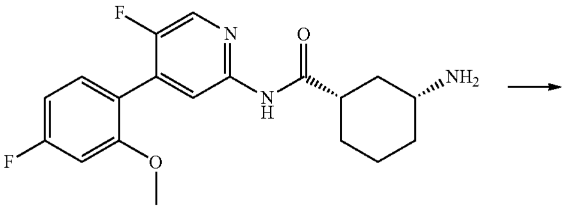

5b

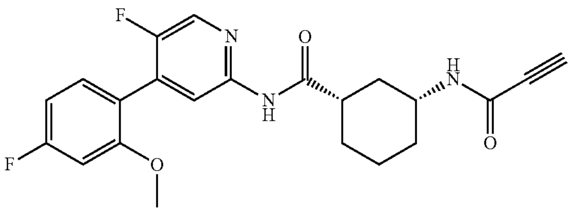

65

Synthesis of Final Product 65

5b (180 mg, 0.50 mmol) and propiolic acid (70 mg, 1.00 mmol) were dissolved in N,N-dimethylformamide (20 mL). 2-(7-azabenzotriazol-1-yl)-N,N,N',N'-tetramethyluronium hexafluorophosphate (380 mg, 1.00 mmol) and N,N-diisopropylethylamine (0.25 mL, 1.50 mmol) were successively added. The reaction mixture was reacted at room temperature for 15 hours until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (petroleum ether:ethyl acetate=4:1-2:1) to give the final product 65 (200 mg, yield 97%).

MS m/z (ESI): 414.2 $[M+H]^+$.

$^1H$ NMR (600 MHz, DMSO-$d_6$) δ 10.60 (s, 1H), 8.73 (d, J=7.8 Hz, 1H), 8.33 (s, 1H), 8.08 (d, J=5.4 Hz, 1H), 7.35 (dd, J=8.4 Hz, J=7.8 Hz, 1H), 7.11 (dd, J=11.4 Hz, J=2.4 Hz, 1H), 6.92-6.90 (m, 1H), 4.12 (s, 1H), 3.79 (s, 3H), 3.64-3.62 (m, 1H), 2.61-2.57 (m, 1H), 1.85-1.74 (m, 4H), 1.35-1.23 (m, 4H).

Example 66

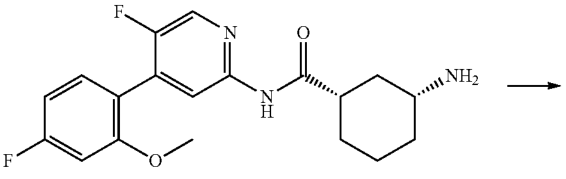

5b

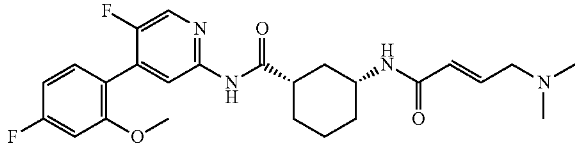

66

Synthesis of Final Product 66

5b (0.25 g, 0.69 mmol) was dissolved in N,N-dimethylformamide (20 mL), and trans-4-dimethylaminocrotonic acid hydrochloride (0.13 g, 0.76 mmol), 2-(7-azabenzotriazol-1-yl)-N,N,N',N'-tetramethyluronium hexafluorophosphate (0.32 g, 0.83 mmol), and N,N-diisopropylethylamine (0.27 g, 2.07 mmol) were added. The reaction mixture was reacted at room temperature for 8 hours until no starting material was detected by TLC. To the reaction solution was added water (30 mL). The mixture was extracted with ethyl acetate (20 mL×5). The organic phases were combined and dried over anhydrous sodium sulfate. The organic phase was directly purified by column chromatography (dichloromethane:methanol=10:1) to give the final product 66 (0.18 g, yield 55%).

MS m/z (ESI): 472.2 $[M+H]^+$.

$^1H$ NMR (600 MHz, DMSO-$d_6$) δ 10.61 (s, 1H), 8.33 (s, 1H), 8.08 (d, J=6.0 Hz, 1H), 8.01 (d, J=6.0 Hz, 1H), 7.35-7.33 (m, 1H), 7.11-7.09 (m, 1H), 6.93-6.90 (m, 1H), 6.56-6.51 (m, 1H), 6.04 (d, J=15.0 Hz, 1H), 3.78 (s, 3H), 3.66 (m, 1H), 3.14 (s, 2H), 2.64-2.60 (m, 1H), 2.25 (s, 6H), 1.91-1.90 (m, 1H), 1.84-1.78 (m, 3H), 1.35-1.13 (m, 4H).

Example 67

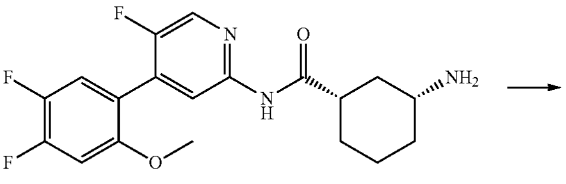

26c

-continued

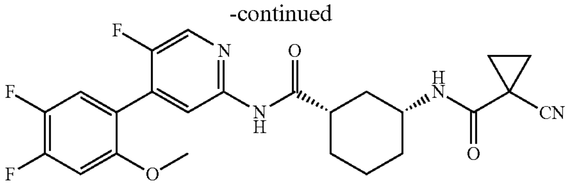

67

Synthesis of Final Product 67

26c (99 mg, 0.26 mmol) was dissolved in N,N-dimethylformamide (5 mL) and then 1-cyano-1-cyclopropane carboxylic acid (44 mg, 0.40 mmol), 2-(7-azabenzotriazol-1-yl)-N,N,N',N'-tetramethyluronium hexafluorophosphate (152 mg, 0.40 mmol) and N,N-diisopropylethylamine (131 μL, 0.79 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane: methanol=50:1-20:1) to give the final product 67 (50 mg, yield 41%).

MS m/z (ESI): 473.2 $[M+H]^+$.

$^1H$ NMR (600 MHz, $CDCl_3$) δ 8.32-8.31 (m, 1H), 8.13 (s, 1H), 7.18-7.15 (m, 1H), 6.84-6.81 (m, 1H), 6.38-6.37 (m, 1H), 3.90-3.85 (m, 1H), 3.79 (s, 3H), 2.49-2.47 (m, 1H), 2.27-2.25 (m, 1H), 2.01-1.94 (m, 3H), 1.70-1.62 (m, 2H), 1.60-48 (m, 5H), 1.32-1.23 (m, 1H).

Example 68

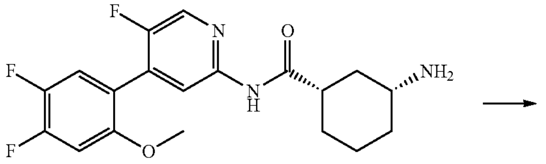

26c

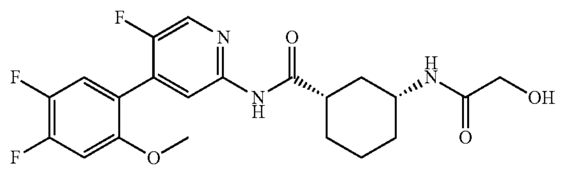

68

Synthesis of Final Product 68

26c (99 mg, 0.26 mmol) was dissolved in N,N-dimethylformamide (5 mL) and then hydroxylacetic acid (20 mg, 0.26 mmol), 2-(7-azabenzotriazol-1-yl)-N,N,N',N'-tetramethyluronium hexafluorophosphate (152 mg, 0.40 mmol) and N,N-diisopropylethylamine (131 μL, 0.79 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=50:1-20:1) to give the final product 68 (50 mg, yield 44%).

MS m/z (ESI): 438.2 $[M+H]^+$.

$^1H$ NMR (600 MHz, DMSO-$d_6$) δ 10.60 (s, 1H), 8.35 (s, 1H), 8.08 (d, J=6.0 Hz, 1H), 7.58-7.56 (m, 1H), 7.53-7.51 (m, 1H), 7.37-7.34 (m, 1H), 5.38 (t, J=6.0 Hz, 1H), 3.82 (s, 5H), 3.74-3.63 (m, 1H), 2.69-2.61 (m, 1H), 1.85-1.70 (m, 4H), 1.33-1.22 (m, 4H).

Example 69

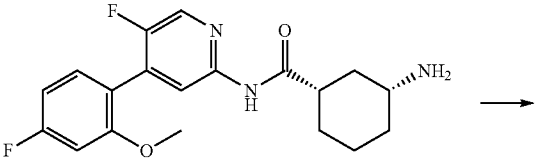

5b

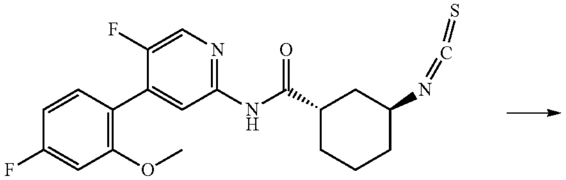

68a

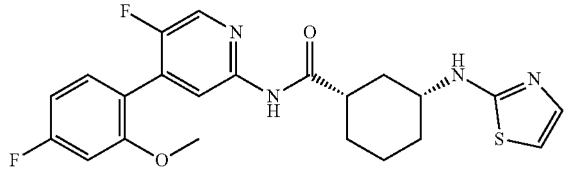

69

Synthesis of Intermediate 69a 5b (0.07 g, 0.19 mmol) was dissolved in absolute ethyl alcohol (20 mL), and triethylamine (0.02 g, 0.19 mmol) and carbon bisulfide (0.02 g, 0.26 mmol) were added. The reaction mixture was reacted at room temperature for 30 minutes. To the reaction solution were added di-tert-butyl dicarbonate (0.04 g, 0.19 mmol) and 4-dimethylaminopyridine (2.3 mg, 0.019 mmol). The reaction mixture was reacted at room temperature for 4 hours until no starting material was detected by TLC. Ethanol was removed under reduced pressure. The residue was directly purified by column chromatography (dichloromethane:methanol=50:1) to give 69a (0.03 g, yield 39%).

Synthesis of final product 69

69a (0.03 g, 0.07 mmol) was dissolved in absolute ethyl alcohol (10 mL), and an amine/ethanol solution (2.0 M, 0.004 g, 0.28 mmol) was added. The reaction mixture was heated to 90° C. and reacted for 4 hours in a sealed tube until no starting material was detected by TLC. The solvent was removed under reduced pressure. The residue was dissolved in absolute ethyl alcohol (10 mL). An aqueous dichloroacetaldehyde solution (40%, 0.005 g, 0.07 mmol) was added. The reaction mixture was heated to 90° C. and reacted for 8 hours until no starting material was detected by TLC. Absolute ethyl alcohol was removed under reduced pressure. The residue was directly purified by column chromatography (dichloromethane:methanol=25:1) to give the final product 69 (0.02 g, yield 64%).

MS m/z (ESI): 445.1 $[M+H]^+$.

$^1$H NMR (600 MHz, DMSO-$d_6$) δ 10.67 (s, 1H), 8.33 (s, 1H), 8.33-8.08 (m, 1H), 7.50 (d, J=7.8 Hz, 1H), 7.35-7.33 (m, 1H), 7.11 (d, J=2.4 Hz, 1H), 7.09 (d, J=2.4 Hz, 1H), 6.99-6.90 (m, 1H), 6.58 (d, J=4.2 Hz, 1H), 3.79 (s, 3H), 3.52-3.50 (m, 1H), 2.63 (m, 1H), 2.14-2.12 (m, 1H), 2.02-2.00 (m, 1H), 1.82-1.78 (m, 2H), 1.36-1.30 (m, 3H), 1.14-1.12 (m, 1H).

Example 70

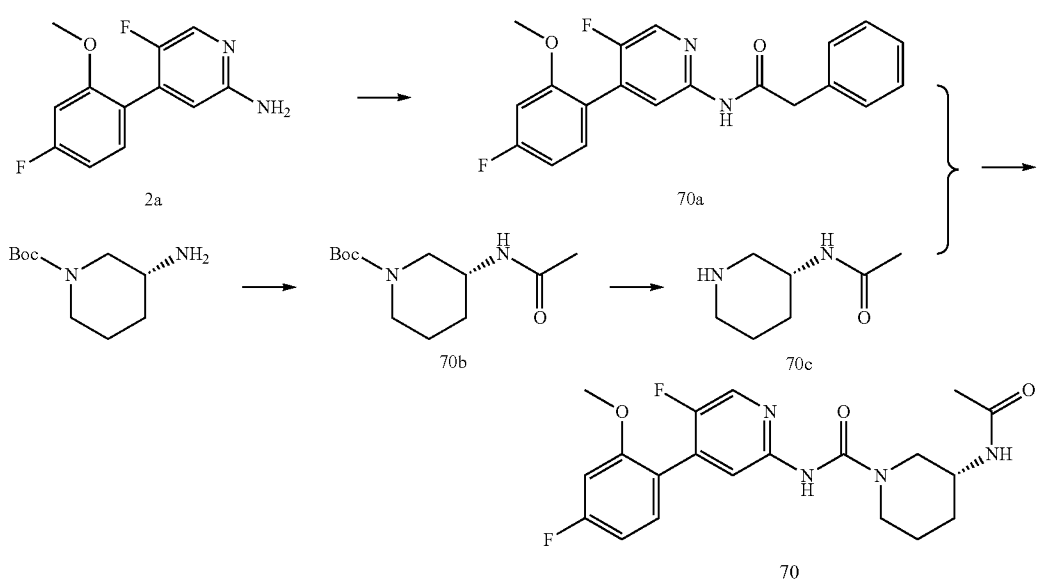

Synthesis of Intermediate 70a 2a (160 mg, 0.68 mmol) was dissolved in tetrahydrofuran (10 mL), and then phenyl chloroformate (191 mg, 1.22 mmol) and potassium carbonate (187 mg, 1.35 mmol) were added. The reaction mixture was stirred overnight until no starting material was detected by TLC. The reaction solution was directly purified by column chromatography (petroleum ether: ethyl acetate=10:1-2:1) to give 70a (200 mg, yield 83%).

Synthesis of Intermediate 70b (R)-1-tert-butyloxycarbonyl-3-aminopiperidine (1.00 g, 5.00 mmol) was dissolved in dichloromethane (30 mL), and then triethylamine (1.52 g, 15.0 mmol) and acetic anhydride (701 μL, 7.50 mmol) were added. The reaction mixture was stirred overnight at room temperature until no starting material was detected by TLC. To the reaction solution was added water (50 mL). The mixture was extracted with dichloromethane (50 mL×3). The organic phases were combined, washed with an aqueous saturated sodium chloride solution (50 mL×2), and dried over anhydrous sodium sulfate. The solvent was removed under reduced pressure to give 70b (1.17 g, yield 97%).

Synthesis of Intermediate 70c 70b (1.17 g, 4.83 mmol) was dissolved in dichloromethane (30 mL), and then trifluoroacetic acid (10 mL) was added in an ice-water bath. The reaction mixture was stirred at room temperature for 3 hours. The solvent was removed under reduced pressure to give 70c (1.50 g), which was directly used in the next step.

Synthesis of Final Product 70

70a (235 mg, 0.66 mmol) was dissolved in tetrahydrofuran (10 mL), and then 70c (339 mg, 1.32 mmol) and triethylamine (458 μL, 3.30 mmol) were added. The reaction mixture was stirred at room temperature for 10 hours until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure.

The crude product was purified by column chromatography (dichloromethane:methanol=40:1-20:1) to give the final product 70 (80 mg, yield 30%).

MS m/z (ESI): 405.2 $[M+H]^+$.

$^1$H NMR (600 MHz, DMSO-$d_6$) δ 9.22 (s, 1H), 8.25 (s, 1H), 7.84 (d, J=7.2 Hz, 1H), 7.75 (d, J=5.4 Hz, 1H), 7.33 (t, J=7.8 Hz, 1H), 7.10 (d, J=11.4 Hz, 1H), 6.92 (t, J=7.8 Hz, 1H), 3.93 (d, J=12.6 Hz, 1H), 3.83 (d, J=12.6 Hz, 1H), 3.80 (s, 3H), 3.64-3.59 (m, 1H), 2.98-2.93 (m, 1H), 2.79-2.76 (m, 1H), 1.82-1.79 (m, 4H), 1.71-1.69 (m, 1H), 1.45-1.36 (m, 2H).

Example 71

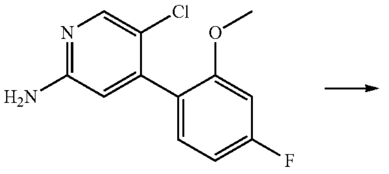

1a

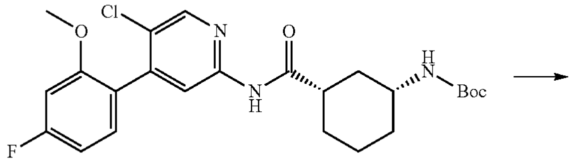

71a

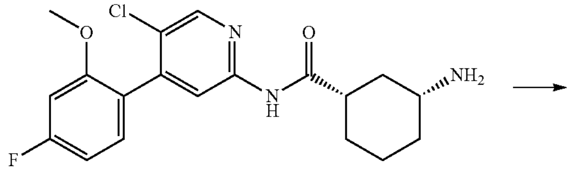

71b

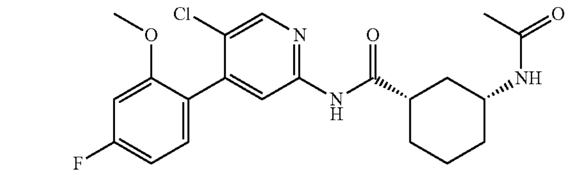

71

Synthesis of Intermediate 71a 1a (0.40 g, 1.58 mmol) was dissolved in N,N-dimethylformamide (30 mL), and then (1S,3R)-3-[(tert-butyloxycarbonyl)amino]cyclohexanecarboxylic acid (0.38 g, 1.58 mmol), 2-(7-azabenzotriazol-1-yl)-N,N,N',N'-tetramethyluronium hexafluorophosphate (0.72 g, 1.90 mmol) and N,N-diisopropylethylamine (0.41 g, 3.16 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-20:1) to give 71a (0.45 g, yield 60%).

Synthesis of Intermediate 71b 71a (0.45 g, 0.94 mmol) was dissolved in dichloromethane (30 mL), and then trifluoroacetic acid (2 mL) was added in an ice-water bath. The reaction mixture was stirred overnight at room temperature until no starting material was detected by TLC. To the reaction solution was added water (100 mL). Then the mixture was adjusted with an aqueous saturated sodium bicarbonate solution to a pH of 9-10 and extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-8:1) to give 71b (0.31 g, yield 87%).

Synthesis of Final Product 71

71b (0.31 g, 0.82 mmol) was dissolved in dichloromethane (35 mL), and then acetic anhydride (0.25 g, 2.47 mmol) and triethylamine (0.25 g, 2.47 mmol) were added. The reaction mixture was stirred at room temperature until no starting material was detected by TLC. To the reaction solution was added water (50 mL). The mixture was extracted with dichloromethane (50 mL×3). The organic phases were combined, washed with saturated sodium chloride solution (50 mL×2), and dried over anhydrous sodium sulfate. The solvent was removed under reduced pressure. The crude product was purified by column chromatography (dichloromethane:methanol=50:1-10:1) to give the final product 71 (0.18 g, yield 52%).

MS m/z (ESI): 420.1 $[M+H]^+$.

$^1$H NMR (600 MHz, $CDCl_3$) δ 10.69 (s, 1H), 8.41 (s, 1H), 8.05 (s, 1H), 7.78 (d, J=7.8 Hz, 1H), 7.25 (d, J=7.2 Hz, 1H), 7.09 (d, J=2.4 Hz, 1H), 6.91-6.88 (m, 1H), 3.76 (s, 3H), 3.57-3.54 (m, 1H), 2.62-2.59 (m, 1H), 1.86-1.84 (m, 1H), 1.76-1.74 (m, 6H), 1.31-1.23 (m, 3H), 1.07-1.05 (m, 1H).

Example 72

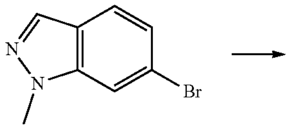

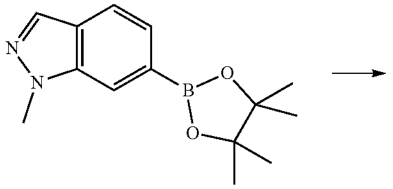

72a

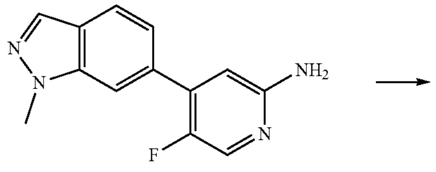

72b

-continued

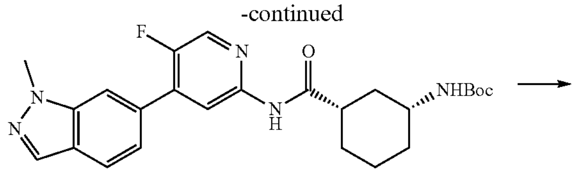

72c

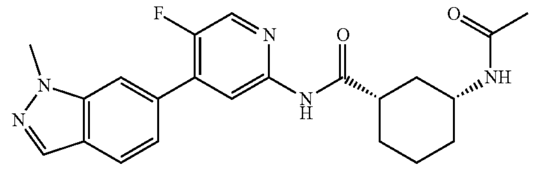

72

Synthesis of Intermediate 72a 6-bromo-1-methyl-1H-indazole (211 mg, 1.00 mmol), bis(pinacolato)diboron (508 mg, 2.00 mmol), potassium acetate (294 mg, 3.00 mmol) and [1,1'-bis(diphenylphosphino)ferrocene]dichloropalladium (73 mg, 0.10 mmol) were dissolved in 1,4-dioxane (20 mL). The reaction mixture was reacted under nitrogen gas protection at 100° C. for 4 hours. until no starting material was detected by TLC, the heating was stopped. To the reaction solution was added water (100 mL). The mixture was extracted with ethyl acetate (100 mL×3). The organic phases were combined, washed with saturated sodium chloride solution (100 mL×2), and dried over anhydrous sodium sulfate. The solvent was removed under reduced pressure. The crude product was purified by column chromatography (petroleum ether-petroleum ether:ethyl acetate=4:1) to give 72a (240 mg, yield 93%).

Synthesis of Intermediate 72b 72a (258 mg, 1.00 mmol) was dissolved in diethylene glycol dimethyl ether (40 mL), and 5-fluoro-4-iodopyridine-2-amine (286 mg, 1.20 mmol), [1,1'-bis(diphenylphosphino) ferrocene]dichloropalladium (73 mg, 0.10 mmol), potassium carbonate (414 mg, 3.00 mmol) and water (10 mL) were added at room temperature. The reaction mixture was stirred at 80° C. for 4 hours. until no starting material was detected by TLC, the reaction was stopped. To the reaction solution was added water (100 mL). The mixture was extracted with ethyl acetate (100 mL×3). The organic phases were combined, washed with saturated sodium chloride solution (100 mL×2), and dried over anhydrous sodium sulfate. The solvent was removed under reduced pressure. The crude product was purified by column chromatography (petroleum ether-petroleum ether:ethyl acetate=1:1) to give 72b (175 mg, yield 72%).

Synthesis of Intermediate 72c 72b (175 mg, 0.72 mmol) and (1S,3R)-3-[(tert-butyloxycarbonyl)amino]cyclohexanecarboxylic acid (350 mg, 1.44 mmol) were dissolved in N,N-dimethylformamide (20 mL). 2-(7-azabenzotriazol-1-yl)-N,N,N',N'-tetramethyluronium hexafluorophosphate (548 mg, 1.44 mmol) and diisopropylethylamine (0.36 mL, 2.16 mmol) were successively added. The reaction mixture was reacted at room temperature for 4 hours until no starting material was detected by TLC. To the reaction solution was added water (50 mL). The mixture was extracted with ethyl acetate (100 mL×3). The organic phases were combined, washed with saturated sodium chloride solution (100 mL×2), and dried over anhydrous sodium sulfate. The solvent was removed under reduced pressure. The crude product was purified by column chromatography (petroleum ether:ethyl acetate=4:1-2:1) to give 72c (200 mg, yield 56%).

Synthesis of Final Product 72

72c (200 mg, 0.40 mmol) was dissolved in dichloromethane (50 mL), and then trifluoroacetic acid (5.00 mL) was added. The reaction mixture was stirred at room temperature for 4 hours until no starting material was detected by TLC. To the reaction mixture was added an aqueous saturated sodium carbonate solution. The pH value of the reaction mixture was adjusted to the weak alkalinity. The aqueous phase was separated and extracted with dichloromethane (100 mL×3). The organic phases were combined and concentrated to a volume of about 50 mL. Triethylamine (2.00 mL) and acetic anhydride (2.00 mL) were added. The reaction mixture was reacted at room temperature for 30 minutes. An aqueous sodium carbonate solution was added to wash the organic phase. The aqueous phase was separated and then extracted with dichloromethane (20 mL×3). The organic phases were combined, washed with saturated sodium chloride solution (50 mL×2), and dried over anhydrous sodium sulfate. The solvent was removed under reduced pressure. The crude product was purified by column chromatography (ethyl acetate) to give the final product 72 (135 mg, yield 83%).

MS m/z (ESI): 410.2 $[M+H]^+$.

$^1H$ NMR (600 MHz, DMSO-$d_6$) δ 10.64 (s, 1H), 8.44 (s, 1H), 8.36 (s, 1H), 8.14 (s, 1H), 7.96 (s, 1H), 7.90 (s, 1H), 7.79 (d, J=7.8 Hz, 1H), 7.33 (d, J=7.8 Hz, 1H), 4.12 (s, 3H), 3.59-3.58 (m, 1H), 2.99-2.95 (m, 1H), 1.91 (s, 3H), 1.82-1.78 (m, 4H), 1.14-1.12 (m, 4H).

Example 73

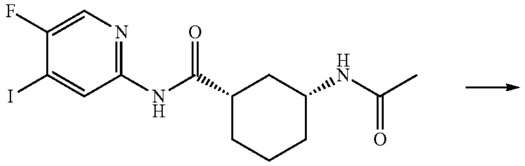

23c

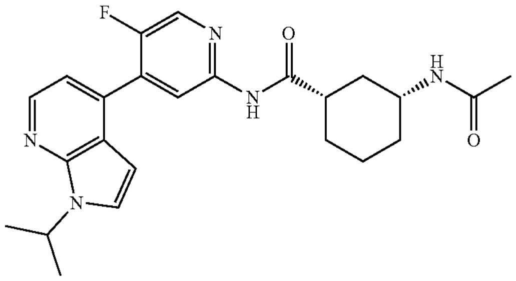

73

Synthesis of Final Product 73

23c (101 mg, 0.25 mmol) was dissolved in 1,4-dioxane (10 mL) and water (5 mL), and then 1-isopropyl-4-(4,4,5, 5-tetramethyl-1,3,2-dioxaborolane-2-yl)-1H-pyrrolo[2,3-b]pyridine (106 mg, 0.37 mmol), [1,1'-bis(diphenylphosphino)ferrocene]dichloropalladium (15 mg, 0.02 mmol) and potassium carbonate (68 mg, 0.49 mmol) were added. The mixture was evacuated and backfilled with $N_2$ (3 times). The reaction mixture was stirred and reacted under reflux at 100° C. for 4 hours until no starting material was detected by TLC. The reaction solution was directly purified by column chromatography (dichloromethane:methanol=50:1-10:1) to give the final product 73 (60 mg, yield 55%).

MS m/z (ESI): 438.2 $[M+H]^+$ $^1$H NMR (600 MHz, DMSO-d6) δ 10.70 (s, 1H), 8.51 (s, 1H), 8.41-8.38 (m, 2H), 7.83 (d, J=3.6 Hz, 1H), 7.79 (d, J=7.8 Hz, 1H), 7.25-7.24 (m, 1H), 6.50-6.49 (m, 1H), 5.17-5.15 (m, 1H), 3.58-3.56 (m, 1H), 2.64-2.60 (m, 1H), 1.90-1.88 (m, 1H), 1.77-1.76 (m, 6H), 1.51 (s, 3H), 1.49 (s, 3H), 1.40-1.25 (m, 3H), 1.15-1.05 (m, 1H).

Example 74

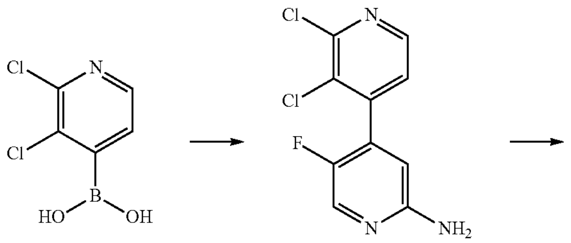

74a

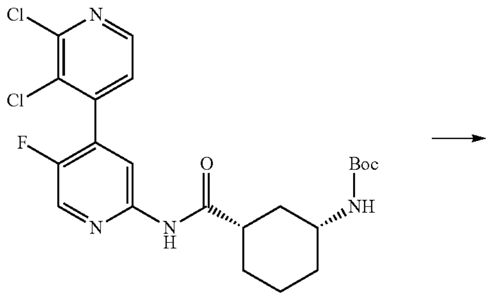

74b

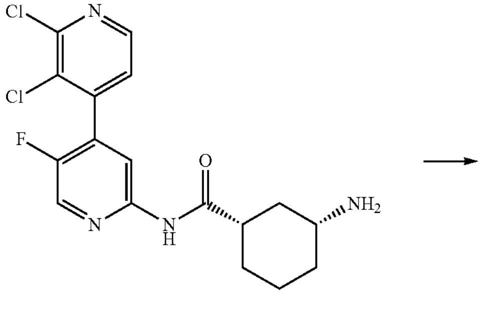

74c

-continued

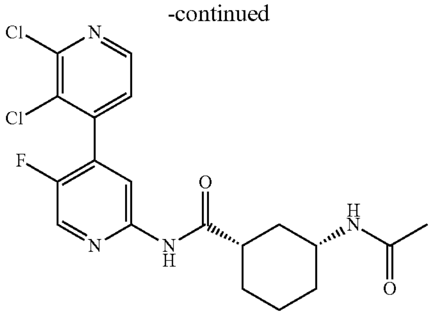

74

Synthesis of Intermediate 74a 2,3-dichloro-pyridine-4-boronic acid (1.05 g, 5.50 mmol) was dissolved in dioxane (30 mL) and water (5 mL), and then 5-fluoro-4-iodo-pyridine-2-amine (1.00 g, 4.20 mmol), [1,1'-bis(diphenylphosphino)ferrocene]dichloropalladium dichloromethane complex (0.34 g, 0.42 mmol), and potassium carbonate (1.74 g, 12.6 mmol) were added. The reaction mixture was heated to 100° C. under nitrogen gas protection and reacted for 8 hours until no starting material was detected by TLC. The reaction mixture was cooled to room temperature. The reaction solution was directly purified by column chromatography (n-hexane:ethyl acetate=1:1) to give the intermediate 74a (0.40 g, yield 37%).

Synthesis of Intermediate 74b 74a (0.13 g, 0.50 mmol) was dissolved in acetonitrile (10 mL), and then (1S,3R)-3-[(tert-butyloxycarbonyl)amino]cyclohexanecarboxylic acid (0.16 g, 0.65 mmol), N,N,N',N'-tetramethylchloroformamidinium hexafluorophosphate (0.17 g, 0.60 mmol) and N-methylimidazole (0.14 g, 1.75 mmol) were added. The reaction mixture was reacted at room temperature for 12 hours until no starting material was detected by TLC. The reaction solution was directly purified by column chromatography (n-hexane:ethyl acetate=2:1) to give 74b (0.12 g, yield 50%).

Synthesis of Intermediate 74c 74b (0.12 g, 0.25 mmol) was dissolved in dichloromethane (20 mL), and trifluoroacetic acid (4 mL) was added. The reaction mixture was reacted at room temperature for 4 hours until no starting material was detected by TLC. The reaction solution was washed with water (30 mL×3), and the aqueous phases were combined. The combined aqueous phase was adjusted with sodium carbonate to a pH of 8-9 and extracted with dichloromethane (30 mL×3). The organic phases were combined, washed with saturated sodium chloride solution (50 mL×2), and dried over anhydrous sodium sulfate. The solvent was removed under reduced pressure to give 74c (0.08 g, yield 84%).

Synthesis of Final Product 74

74c (0.08 g, 0.21 mmol) was dissolved in dichloromethane (20 mL), and then acetic anhydride (0.04 g, 0.42 mmol) and triethylamine (0.04 g, 0.42 mmol) were added. The reaction mixture was reacted at room temperature for 2 hours until no starting material was detected by TLC. The reaction solution was directly purified by column chromatography (dichloromethane:methanol=50:1) to give the final product 74 (0.02 g, yield 22%).

MS m/z (ESI): 426.2 $[M+H]^+$.

$^1H$ NMR (600 MHz, DMSO-d6) δ 10.81 (s, 1H), 8.55-8.54 (m, 2H), 8.18 (d, J=5.4 Hz, 1H), 7.80 (d, J=7.8 Hz, 1H), 7.6 (d, J=5.4 Hz, 1H), 3.60-3.54 (m, 1H), 2.64-2.60 (m, 1H), 1.90-1.88 (m, 1H), 1.77-1.76 (m, 6H), 1.40-1.20 (m, 3H), 1.19-1.05 (m, 1H).

Example 76

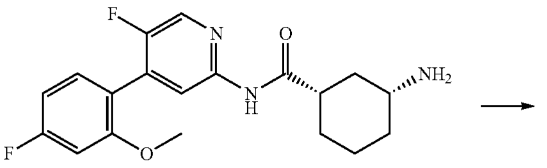

5b

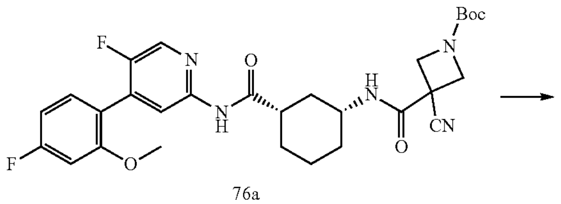

76a

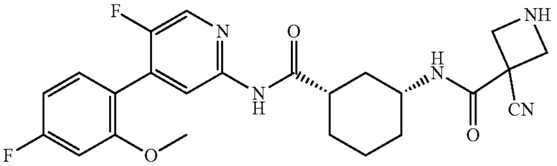

76

Synthesis of Intermediate 76a 5b (500 mg, 1.385 mmol) was dissolved in N,N-dimethylformamide (15 mL), and then 1-[(tert-butoxy)carbonyl]-3-cyanoazetidine-3-carboxylic acid (375 mg, 1.66 mmol), 2-(7-azabenzotriazol-1-yl)-N,N,N',N'-tetramethyluronium hexafluorophosphate (787 mg, 2.07 mmol) and N,N-diisopropylethylamine (687 μL, 4.15 mmol) were added. The reaction mixture was stirred and reacted at room temperature for 10 hours until no starting material was detected by TLC. To the reaction solution was added water (50 mL). The reaction mixture was stirred for 30 minutes, filtered, and dried over anhydrous sodium sulfate. Then the solvent was removed under reduced pressure to give 76a (497 mg, yield 63%).

Synthesis of Final Product 76

76a (497 mg, 0.87 mmol) was dissolved in dichloromethane (20 mL), and then trifluoroacetic acid (5 mL) was added. The reaction mixture was stirred at room temperature for 2 hours until no starting material was detected by TLC. To the reaction solution was added water (100 mL). The mixture was adjusted with sodium bicarbonate to a pH of 8 and extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=40:1) to give the final product 76 (396 mg, yield 97%).

MS m/z (ESI): 470.2 $[M+H]^+$.

$^1H$ NMR (600 MHz, $CD_3OD$) δ 8.38 (s, 1H), 7.75 (d, J=5.4 Hz, 1H), 7.50-7.42 (m, 1H), 7.04 (d, J=10.8 Hz, 1H), 6.96-6.86 (m, 1H), 4.60-4.32 (m, 4H), 3.93-3.76 (m, 4H), 2.70 (m, 1H), 2.23 (m, 1H), 2.00 (m, 3H), 1.71-1.46 (m, 3H), 1.43-1.27 (m, 1H).

Example 77

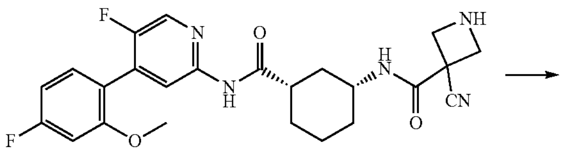

76

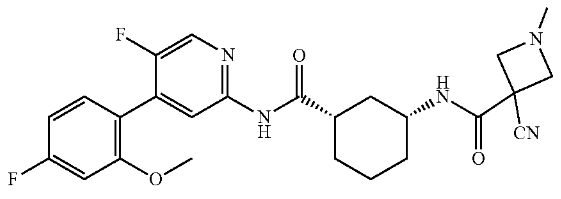

77

Synthesis of Final Product 77

76 (296 mg, 0.63 mmol) was dissolved in methanol (10 mL), and then an aqueous formaldehyde solution (1 mL), sodium triacetoxyborohydride (249 mg, 1.27 mmol), and one drop of acetic acid were added. The reaction mixture was stirred and reacted at room temperature for 10 hours until no starting material was detected by TLC. To the reaction solution was added water (50 mL). The mixture was adjusted with sodium bicarbonate to a pH of 8 and extracted with ethyl acetate (50 mL×3). The organic phases were combined, washed with saturated sodium chloride solution (50 mL×2), and dried over anhydrous sodium sulfate. The solvent was removed under reduced pressure to give the final product 77 (186 mg, yield 61%).

MS m/z (ESI): 484.2$[M+H]^+$ $^1H$ NMR (600 MHz, DMSO-$d_6$) δ 10.56 (s, 1H), 8.32 (s, 1H), 8.05 (d, J=4.8 Hz, 1H), 8.10 (d, J=7.8 Hz, 1H), 7.34-7.31 (m, 1H), 7.09 (s, 1H), 6.91-6.88 (m, 1H), 3.79 (s, 3H), 3.68-3.56 (m, 1H), 2.98-2.73 (m, 4H), 2.59-2.55 (m, 1H), 2.42 (s, 3H), 1.81-1.67 (m, 4H), 1.30-1.09 (m, 4H).

Example 78

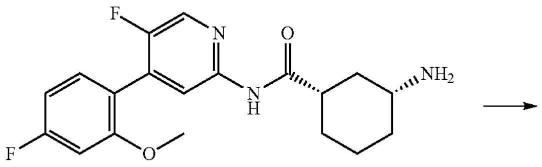

5b

-continued

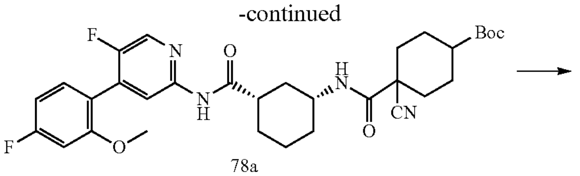

78a

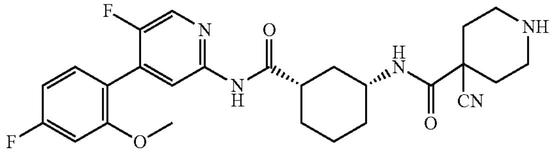

78

Synthesis of Intermediate 78a 5b (500 mg, 1.385 mmol) was dissolved in N,N-dimethylformamide (15 mL), and then 1-(tert-butoxycarbonyl)-4-cyanopiperidine-4-carboxylic acid (422 mg, 1.66 mmol), 2-(7-azabenzotriazol-1-yl)-N,N,N',N'-tetramethyluronium hexafluorophosphate (787 mg, 2.07 mmol) and N,N-diisopropylethylamine (687 μL, 4.15 mmol) were added. The reaction mixture was stirred and reacted at room temperature for 10 hours until no starting material was detected by TLC. To the reaction solution was added water (50 mL). The mixture was stirred for 30 minutes, filtered, and dried over anhydrous sodium sulfate to give 78a (504 mg, yield 61%).

Synthesis of Final Product 78

78a (504 mg, 0.84 mmol) was dissolved in dichloromethane (20 mL), and then trifluoroacetic acid (5 mL) was added. The reaction mixture was stirred at room temperature for 2 hours until no starting material was detected by TLC. To the reaction solution was added water (100 mL). The mixture was adjusted with sodium bicarbonate to a pH of 8 and extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane:methanol=40:1) to give the final product 78 (384 mg, yield 92%).

MS m/z (ESI): 498.7 $[M+H]^+$.

$^1$H NMR (600 MHz, $CD_3OD$) δ 8.32 (s, 1H), 8.07 (d, J=8.4 Hz, 1H), 7.35-7.33 (m, 1H), 7.11-7.10 (m, 1H), 7.08-6.91 (m, 1H), 3.78 (s, 3H), 3.78-3.66 (m, 1H), 3.30-3.28 (m, 2H), 2.99-2.97 (m, 2H), 2.62-2.52 (m, 1H), 2.30-2.22 (m, 4H), 1.79-1.77 (m, 4H), 1.46-1.43 (m, 1H), 1.29-1.26 (m, 3H).

Example 79

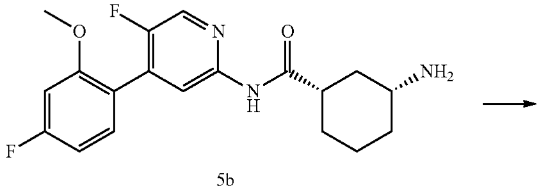

5b

-continued

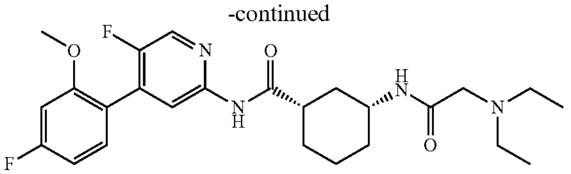

79

Synthesis of Final Product 79

5b (0.16 g, 0.43 mmol) was dissolved in N,N-dimethylformamide (30 mL), and then N,N-diethylglycine hydrochloride (109 mg, 0.65 mmol), 2-(7-azabenzotriazol-1-yl)-N,N,N',N'-tetramethyluronium hexafluorophosphate (178 mg, 0.47 mmol) and N,N-diisopropylethylamine (111 mg, 0.86 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane: methanol=50:1-20:1) to give the final product 79 (116 mg, yield 57%).

MS m/z (ESI): 475.3 $[M+H]^+$ $^1$H NMR (600 MHz, $CDCl_3$) δ 8.23 (d, J=7.8 Hz, 1H). 8.13 (s, 1H), 8.07 (s, 1H), 7.40 (m, 1H), 7.277.22 (m, 1H), 6.87-6.60 (m, 2H), 3.94-3.84 (m, 1H), 3.81 (s, 3H), 3.01 (s, 2H), 2.54 (m, 4H), 2.45 (m, 1H), 2.22 (m, 1H), 1.96 (m, 3H), 1.56-1.36 (m, 3H), 1.26-1.12 (m, 1H), 1.01 (m, 6H).

Example 80

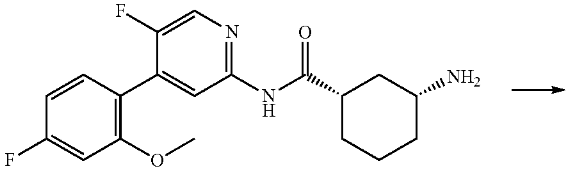

5b

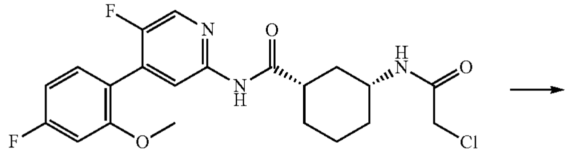

80a

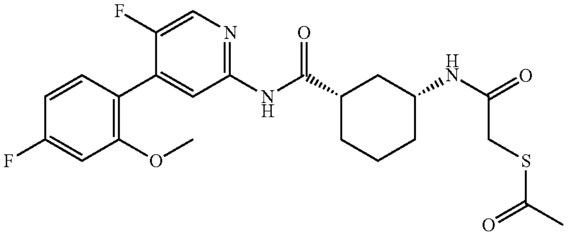

80

Synthesis of Intermediate 80a 5b (0.30 g, 0.83 mmol) was dissolved in dichloromethane (10 mL), and then triethylamine (420 mg, 4.15 mmol) and chloroacetyl chloride (186 mg, 1.66 mmol) were added at 0° C. The reaction mixture was stirred overnight at room temperature until no starting material was detected by TLC. To the reaction solution was added water (20 mL). The mixture was extracted with ethyl acetate (10 mL×3). The organic phases were combined, washed with saturated sodium chloride solution (10 mL×2), and dried over anhydrous sodium sulfate. Then the solvent was removed under reduced pressure. The crude product was purified by column chromatography (n-hexane:ethyl acetate=1:0-0:1) to give 80a (200 mg, yield 55%).

Synthesis of Final Product 80

80a (200 mg, 0.46 mmol) was dissolved in N,N-dimethylformamide (10 mL), and then potassium thioacetate (78.25 mg, 0.69 mmol) was added. The reaction mixture was reacted at room temperature for 2 hours until no starting material was detected by TLC. The reaction solution was added to an aqueous HCl solution (1M, 10 mL), and then water (10 mL) and dichloromethane (15 mL) were added. The mixture was extracted with dichloromethane (10 mL×3). The organic phases were combined, washed with saturated sodium chloride solution (10 mL×2), and dried over anhydrous sodium sulfate. Then the solvent was removed under reduced pressure. The crude product was purified by column chromatography (n-hexane:ethyl acetate=1:0-0:1) to give the final product 80 (200 mg, yield 91%).

MS m/z (ESI): 478.2 $[M+H]^+$ $^1H$ NMR (600 MHz, DMSO-$d_6$) δ 10.58 (s, 1H), 8.33 (s, 1H), 8.07 (d, J=5.4 Hz, 1H), 7.59 (d, J=8.4 Hz, 1H), 7.35-7.34 (m, 1H), 7.33-7.11 (m, 1H), 7.09-6.90 (m, 1H), 4.39 (s, 2H), 3.78 (s, 3H), 3.65-3.63 (m, 1H), 2.66-2.60 (m, 1H), 2.58 (s, 3H), 1.85-1.69 (m, 4H), 1.24-1.14 (m, 4H).

Example 81

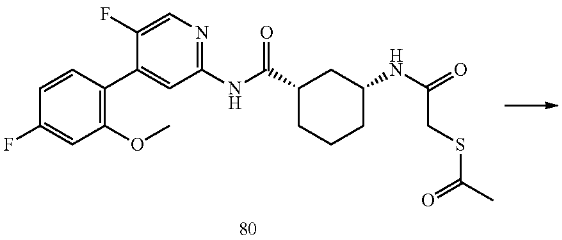

80

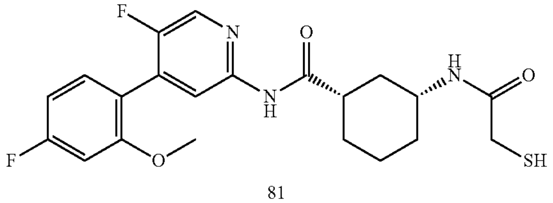

81

Synthesis of Final Product 81

80 (220 mg, 0.46 mmol) was dissolved in methanol (5 mL), and then potassium carbonate (317 mg, 2.30 mmol) was added. The reaction mixture was reacted at room temperature for 20 minutes, and then heated up to 55° C. and reacted for 40 minutes until no starting material was detected by TLC. To the reaction solution was added water (20 mL). The mixture was extracted with ethyl acetate (10 mL×3). The organic phases were combined, washed with saturated sodium chloride solution (10 mL×2), and dried over anhydrous sodium sulfate. Then the solvent was removed under reduced pressure. The crude product was purified by column chromatography (n-hexane:ethyl acetate=1:0-0:1) to give the final product 81 (41 mg, yield 20%).

MS m/z (ESI): 436.2 $[M+H]^+$ $^1H$ NMR (600 MHz, DMSO-$d_6$) δ 10.55 (s, 1H), 8.31 (s, 1H), 8.07 (d, J=5.4 Hz, 1H), 7.56 (d, J=9.0 Hz, 1H), 7.35-7.32 (m, 1H), 7.09-7.07 (m, 1H), 6.91-6.88 (m, 1H), 3.89-3.84 (m, 4H), 3.66-3.63 (m, 1H), 3.24-3.22 (m, 2H), 2.61-2.57 (m, 1H), 1.83-1.68 (m, 4H), 1.34-1.26 (m, 4H).

Example 82

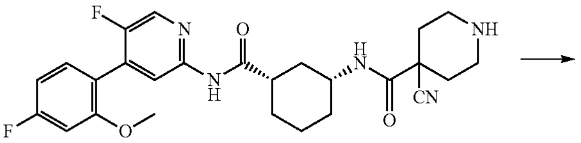

78

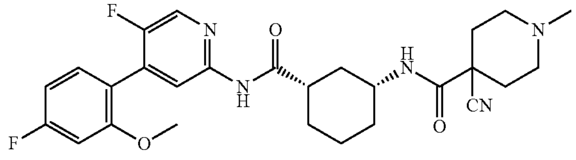

82

Synthesis of Final Product 82

78 (300 mg, 0.60 mmol) was dissolved in methanol (10 mL), and then an aqueous formaldehyde solution (1 mL), sodium triacetoxyborohydride (235 mg, 1.20 mmol), and one drop of acetic acid were added. The reaction mixture was stirred and reacted at room temperature for 10 hours until no starting material was detected by TLC. To the reaction solution was added water (50 mL). The mixture was adjusted with sodium bicarbonate to a pH of 8 and extracted with ethyl acetate (50 mL×3). The organic phases were combined, washed with saturated sodium chloride solution (50 mL×2), and dried over anhydrous sodium sulfate. The solvent was removed under reduced pressure to give the final product 82 (205 mg, yield 67%).

MS m/z (ESI): 512.2[M+H]+

$^1H$ NMR (600 MHz, DMSO-$d_6$) δ 10.28 (s, 1H), 8.28 (s, 1H), 8.22-8.09 (m, 1H), 8.05 (d, J=8.4 Hz, 1H), 7.32-7.30 (m, 1H), 7.09-7.02 (m, 1H), 6.91-6.87 (m, 1H), 3.80 (s, 3H), 3.75-3.66 (m, 1H), 3.57-3.52 (m, 1H), 3.16-2.96 (m, 2H), 2.81-2.59 (m, 4H), 2.50-2.48 (m, 2H), 2.43-2.31 (m, 3H), 2.00-1.74 (m, 4H), 1.52-1.48 (m, 1H), 1.41-1.22 (m, 3H).

Example 83

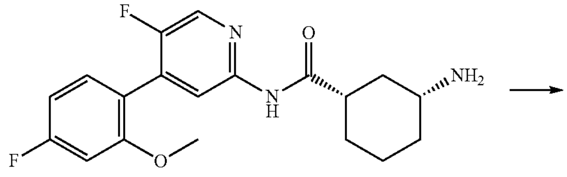

5b

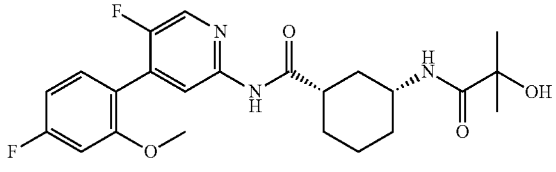

83

Synthesis of Final Product 83

5b (0.20 g, 0.55 mmol) was dissolved in N,N-dimethylformamide (30 mL), and then 2-hydroxyisobutyric acid (68 mg, 0.65 mmol), 2-(7-azabenzotriazol-1-yl)-N,N,N',N'-tetramethyluronium hexafluorophosphate (178 mg, 0.47 mmol) and N,N-diisopropylethylamine (111 mg, 0.86 mmol) were added. The reaction mixture was stirred overnight at room temperature until no starting material was detected by TLC. To the reaction solution was added water (100 mL). The mixture was extracted with ethyl acetate (50 mL×3). The organic phases were combined, washed with saturated sodium chloride solution (50 mL×2), and dried over anhydrous sodium sulfate. Then the solvent was removed under reduced pressure. The crude product was purified by column chromatography (dichloromethane: methanol=50:1-20:1) to give the final product 83 (81 mg, yield 33%).

MS m/z (ESI): 448.2 $[M+H]^+$ $^1$H NMR (600 MHz, $CDCl_3$) δ 8.31 (s, 1H), 8.24 (d, J=8.4 Hz, 1H), 8.12 (s, 1H), 7.26-7.24 (m, 1H), 6.76-6.73 (m, 2H), 6.63 (d, J=12.6 Hz, 1H), 3.90-3.82 (m, 1H), 3.81 (s, 3H), 2.65 (s, 1H), 2.56-2.42 (m, 1H), 2.26-2.23 (m, 1H), 2.00-1.89 (m, 3H), 1.61-1.49 (m, 2H), 1.45 (d, J=4.8 Hz, 6H), 1.30-1.18 (m, 1H).

Examples 75 and 84-90

According to the synthesis methods of Examples 1-72, the corresponding starting materials were selected to synthesize compounds 75 and 84-90, which had the following structures:

75

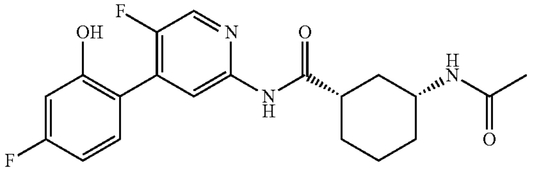

-continued

84

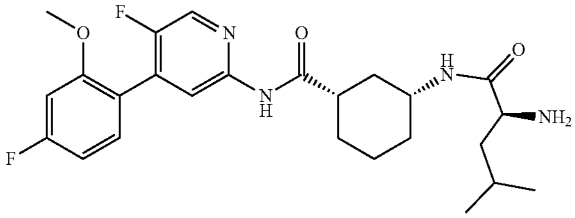

85

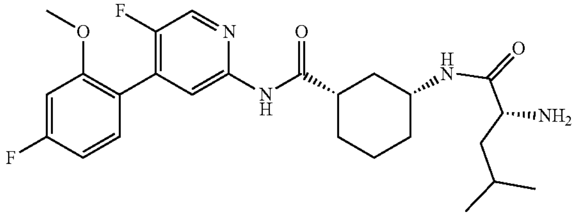

86

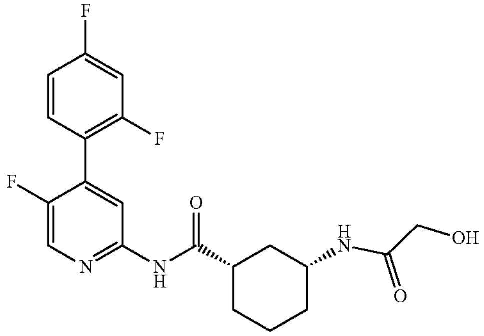

87

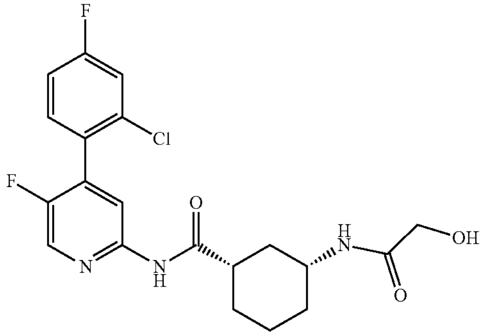

88

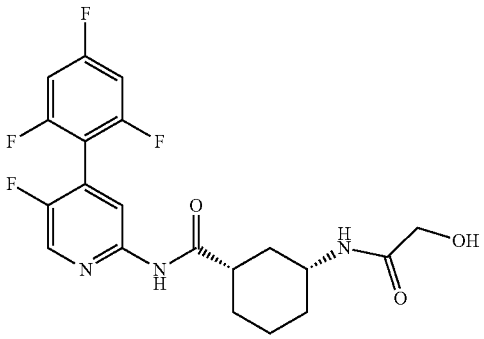

-continued

89

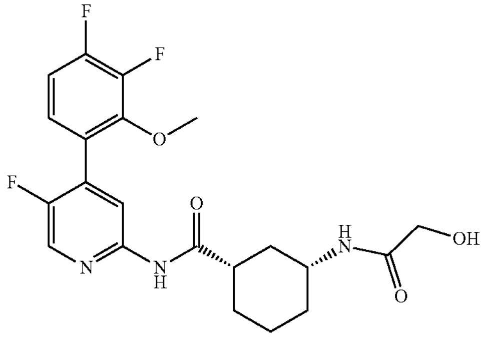

90

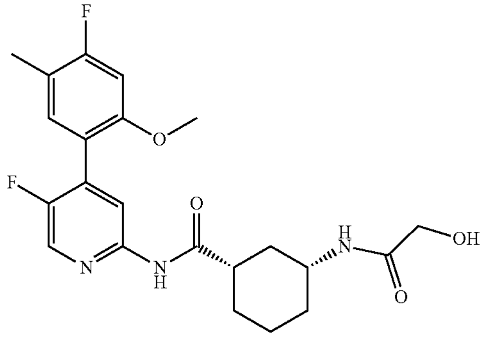

Assay Example 1: Inhibitory Effect Assay of the Compounds of the Present Disclosure on CDK9, CDK1, CDK2, CDK4, CDK5, CDK6, and CDK7

1. Assay Object

The inhibitory effects of the compounds on CDK 1/2/4/5/6/7/9 kinases were tested, and the effective $IC_{50}$ values were obtained by fitting and calculation.

2. CDKs Test Family

CDK1/CDK2/CDK4/CDK5/CDK6/CDK7/CDK9

TABLE 1

Information of kinases, substrates, and ATP in the in vitro assay

| Kinases | Kinase concentration in reaction solution (ng/well) | Substrates | Substrate concentration in reaction solution(μM) | ATP concentration in reaction solution (μM) |
|---|---|---|---|---|
| CDK1 | 11 | Rb(ser780)-biotin | 0.7 | 20 |
| CDK2 | 5 | ATF2-biotin | 0.5 | 5 |
| CDK4 | 12 | Rb(ser780)-biotin | 1 | 70 |
| CDK5 | 6 | ATF2-biotin | 0.1 | 40 |
| CDK6 | 12 | Rb(ser780)-biotin | 0.3 | 50 |
| CDK7 | 20 | Rb(ser780)-biotin | 0.6 | 20 |
| CDK9 | 13 | Rb(ser780)-biotin | 0.4 | 5 |

3. Test Procedure 3.1 Compound Dilution

Compounds were diluted with DMSO to 11 concentrations by 3-fold dilution, wherein the highest concentration of the reference compound staurosporine was 1 μM, and the highest concentration of the compounds to be tested was 10 μM.

3.2 Kinase Reaction

A compound dissolved in DMSO (50 nL) was transferred to the kinase reaction plate by using acoustic technology (Echo). 5 μL of a CDK kinase dilution solution was added to the kinase reaction plate and incubated at room temperature for 10 minutes after centrifugation. 5 μL of a substrate premix solution was added to the plate, and the final concentrations of the substrate and the ATP in each well were shown in Table 1. After centrifugation, the reaction was performed at 30° C. for 120 minutes.

3.3 Reaction Termination and Signal Detection

10 μL of a stop solution was added to each well, and after centrifugation, the plate was incubated at room temperature for 120 minutes, and then incubated at 4° C. overnight. Signal values were read on an Envision instrument using the HTRF program and data analysis was performed. $IC_{50}$ (the inhibitory concentration at 50% maximal effect) values were expressed in nM. The results were shown in Table 2.

TABLE 2

Inhibitory effect of the compounds of the present disclosure on CDKs 1, 2, 4, 5, 6, 7 and 9

| Compound No. | CDK1 | CDK2 | CDK4 | CDK5 | CDK6 | CDK7 | CDK9 |
|---|---|---|---|---|---|---|---|
| 3 | 262.30 | 2125.25 | 1072.71 | 721.37 | 1386.48 | 6206.50 | 16.76 |
| 5 | 124.66 | 475.36 | 429.08 | 452.07 | 1122.94 | 2748.45 | 7.90 |
| 7 | 225.33 | 1050.81 | 576.76 | 909.78 | 2357.11 | 6436.19 | 7.15 |
| 8 | 214.01 | 990.57 | 272.58 | 613.63 | 1772.62 | >9901 | 7.21 |
| 12 | 151.50 | 533.23 | 585.34 | 297.25 | 2742.71 | >9901 | 7.44 |
| 17 | 193.43 | 1434.89 | 474.43 | 356.71 | 3170.28 | 5479.89 | 7.12 |
| 19 | 87.06 | 638.35 | 196.33 | 292.83 | 296.51 | 1170.59 | 7.65 |
| 25 | 264.88 | 2049.19 | 810.74 | 716.35 | 2358.61 | 4358.69 | 7.54 |
| 32 | 86.66 | 1070.98 | 353.47 | 329.06 | 2446.37 | 1647.21 | 6.86 |
| 33 | 78.76 | 760.62 | 395.17 | 168.27 | 1763.34 | 1258.25 | 6.68 |
| 36 | 96.95 | 557.80 | 629.91 | 209.32 | 3374.38 | 3716.69 | 6.88 |
| 37 | 82.02 | 688.01 | 361.17 | 248.35 | 2637.75 | 2653.96 | 6.44 |
| 41 | 196.36 | 1248.20 | 628.81 | 361.31 | 4977.69 | 1083.06 | 7.65 |
| 42 | 72.60 | 252.85 | 184.31 | 139.53 | 1013.52 | 992.14 | 6.66 |
| 43 | 79.97 | 822.98 | 581.91 | 296.00 | 3077.51 | 2406.88 | 7.17 |
| 45 | 93.21 | 563.61 | 784.82 | 283.52 | 2795.36 | 4443.59 | 6.92 |
| 48 | 132.89 | 775.90 | 766.94 | 300.93 | 3628.37 | 2151.13 | 6.84 |
| 67 | 67.56 | 391.94 | 267.98 | 82.90 | 599.52 | 1425.15 | 5.45 |
| 68 | 73.57 | 273.81 | 402.22 | 161.76 | 2034.21 | 2629.18 | 5.55 |

The above assay indicated that the compounds evaluated in the present disclosure displayed selectivity for CDK9 and had a potent inhibitory effect on CDK9.

Assay Example 2: In Vitro Inhibitory Effect of CDK9 Inhibitor on MV4;11 Cell Proliferation 1. Assay Object The in vitro inhibitory effect of the synthesized compounds on cell proliferation was investigated.

2. Assay Principle

The trade name of MTT was thiazole blue, which was a tetrazolium salt of a dye that could accept hydrogen atoms. The succinate dehydrogenase in the mitochondria of living cells could reduce exogenous MTT to insoluble blue-purple crystals and deposited in cells, but dead cells did not have this function. Dimethyl sulfoxide could dissolve blue-purple complexes in cells, and its light absorption value could be measured at 490-550 nm wavelength with an enzyme-linked immunosorbent detector, which could indirectly reflect the number of cells. Within a certain range of the cell number, the amount of MTT crystals formed was proportional to the number of cells. The drug to be tested was successively diluted to different concentrations and added to a 96-well plate. The OD value was determined after the drug acted for a certain time. The size of the OD value could reflect the number of living cells, and its $IC_{50}$ value was calculated with SPSS19.0.

3. Assay Apparatus

Model 371 $CO_2$ Incubator: Thermo

Model IX70-142 Inverted Fluorescence Microscope: Olympus

HFsafe-1500 Type biological safety cabinet: Shanghai Lishen Scientific Instrument Co., Ltd.

Varloskan flash Microplate reader: Thermo Company

Precision electronic balance: Mettler AL204 Type

4. Assay Material:

4.1 Cell and Culture Medium

| Cell name | cell source | culture medium | Culture medium manufacturer |
|---|---|---|---|
| MV4; 11 | Shanghai Cell Bank | 10% IMDM | gibco |

4.2 Assay Material

| name | Specification | Manufacturer |
|---|---|---|
| fetal bovine serum | 500 mL/bottle | Cellmo |
| PBS | 2 L/bag | Solarbio |
| DMSO | 500 mL/bottle | Guangfu |
| MTT | 5 g/bottle | Amresco |

4.3 Reagent Preparation 5 mg/mL MTT working solution: 0.5 g of MTT was dissolved in 100 mL of PBS, sterilized by filtration with a 0.22 μm microporous filter, and stored at 4° C. in a refrigerator (use within two weeks) or at −20° C. for long-term storage.

5. Assay Method 5.1 Plating

Suspension of cells: Cells were resuspended by centrifugation and counted. A certain density of cell suspension was formulated with a complete culture medium, blown evenly, inoculated on a 96-well plate, 100 μL per well, and then cultured in a $CO_2$ incubator.

5.2 Formulation of Drug

An appropriate amount of the drug was added to a calculated amount of DMSO and dissolved. The resulting mixture was dispensed and stored at −20° C. The formulation concentration was 10 mM.

5.3 Addition of Drug

The stock solution of the compound having a concentration of 10 mM was diluted into different concentrations (8 concentrations) of solutions of the compound in DMSO (3-fold dilution, 20×final concentration). Each concentration of solutions (10 μL) of the compound in DMSO was respectively diluted with cell culture media (90 μL) to formulate working solutions (2×final concentration). Each concentration of working solutions (100 μL) of the compound was added to the 96-well plate inoculated with cells (1×final concentration, the highest final concentration is 1000 nM). The resulting plate continued to be cultured in a $CO_2$ incubator.

6. Test

The 96-well plate was taken out, and the density of cells was observed under a microscope. The test was performed with the MTT method.

MTT method: 20 μL of MTT was added to each well; the plate was cultured for about 4 hours in the incubator; the liquid in the well was discarded; 150 μL of DMSO was added into each well; the plate was placed in a shaker and shaken for 5-10 minutes, and the test was performed with a microplate reader at a wavelength of 550 nm. 7. Data analysis: $IC_{50}$ value of the drug was calculated with SPSS19.0 statistical software.

The result of the compounds for cell proliferation inhibition was shown in Table 3:

TABLE 3

Assay data of the compounds of the present disclosure for cell proliferation inhibition

| Compound No. | $IC_{50}$ (μM) |
|---|---|
| 3 | 0.120 |
| 5 | 0.037 |
| 6 | 0.179 |
| 7 | 0.043 |
| 8 | 0.045 |
| 13 | 0.117 |
| 15 | 0.009 |
| 17 | 0.025 |
| 18 | 0.176 |
| 19 | 0.026 |
| 20 | 0.067 |
| 22 | 0.036 |
| 23 | 0.023 |
| 24 | 0.119 |
| 25 | 0.034 |
| 26 | 0.089 |
| 32 | 0.011 |
| 33 | 0.017 |
| 34 | 0.021 |
| 35 | 0.032 |
| 36 | 0.044 |
| 37 | 0.052 |
| 38 | 0.010 |
| 40 | 0.008 |
| 41 | 0.045 |
| 42 | 0.017 |
| 43 | 0.022 |
| 44 | 0.010 |
| 45 | 0.034 |
| 46 | 0.017 |

TABLE 3-continued

Assay data of the compounds of the present disclosure for cell proliferation inhibition

| Compound No. | $IC_{50}$ (μM) |
|---|---|
| 47 | 0.013 |
| 48 | 0.026 |
| 49 | 0.072 |
| 50 | 0.037 |
| 51 | 0.013 |
| 52 | 0.008 |
| 53 | 0.010 |
| 54 | 0.012 |
| 55 | 0.014 |
| 56 | 0.020 |
| 57 | 0.100 |
| 58 | 0.086 |
| 59 | 0.006 |
| 60 | 0.012 |
| 61 | 0.048 |
| 62 | 0.006 |
| 63 | 0.096 |
| 64 | 0.009 |
| 65 | 0.006 |
| 66 | 0.034 |
| 67 | 0.067 |
| 68 | 0.050 |
| 69 | 0.028 |
| 70 | 0.259 |
| 71 | 0.016 |
| 77 | 0.021 |
| 81 | 0.067 |
| 82 | 0.021 |
| 83 | 0.014 |

Assay conclusion: According to the data in the table, the compounds of the present disclosure had a relatively strong inhibitory effect on CDK9, and the in vitro cell inhibitory activity was substantially below 300 nM, and the optimal value could reach several nM.

Assay Example 3: Investigation of In Vitro hERG Inhibitory Activity

1. Assay Object:

Rapid delayed rectifier current (IKr) was mainly mediated by the hERG ion channel and involved in human cardiomyocyte repolarization. Inhibition of IKr was the leading cause of the clinical QT interval prolongation syndrome, even acute cardiac dysrhythmia, and even sudden death. By utilizing a whole-cell patch-clamp technology, the blocking effect of a compound on the hERG channel was detected on a CHO-K1 cell line stably expressing the hERG channel, and the half inhibition concentration $IC_{50}$ of the compound was determined. It was used as a part of the comprehensive cardiac safety assessment, and it was initially evaluated in the safety in vitro screen for cardiotoxicity.

2. Assay Method:

This assay included the following aspects:

The hERG current was recorded on the CHO-K1 cell line stably expressing the hERG channel by utilizing the manual patch-clamp technology;

The inhibition rate at each concentration was calculated according to the hERG tail current;

The measurement was performed at 5 concentrations for each compound to calculate the $IC_{50}$ value;

3 cells were tested at each concentration;

One positive control drug was provided.

The hERG current was recorded by utilizing a whole-cell patch-clamp technology. The cell suspension was added to a dish, and the dish was placed on the object stage of an upright microscope. After adhesion of the cells, perfusion was performed with an extracellular fluid at a flow rate of 1-2 m/min. A glass microelectrode was pulled with a micro-electrode puller via a two-step process and the pipette rip resistance was between 2-5 MΩ. After the whole-cell record was set up, the clamp potential was held at −80 mV. The cells were depolarized to +60 mV by applying a voltage stimulus and then repolarized to −50 mV to elicit the hERG tail current. All recordation was conducted after the current became stable. The extracellular perfusion administration was started from the lowest concentration, staying for 5-10 min at each concentration until the current was stable, and then conducted with the next concentration. The half inhibition concentration ($IC_{50}$) of the compound was obtained by best-fitting with the Logistic equation.

Amitriptyline was one of the most widely-used drugs for blocking the hERG current. Therefore, it was used as a positive control drug in the study.

3. The Result was Shown in Table 4:

TABLE 4

$IC_{50}$ values of the compounds on the hERG current recorded on the CHO-K1 stable cell line
The hERG inhibition of the compounds

| Compound No. | $IC_{50}$ (μM) | Number of the used cells | Slope |
|---|---|---|---|
| 3 | >30.00 | 3 | — |
| 5 | >30.00 | 3 | — |
| 7 | >30.00 | 3 | — |
| 8 | >30.00 | 3 | — |
| 12 | >30.00 | 3 | — |
| 17 | >30.00 | 3 | — |
| 19 | >30.00 | 3 | — |
| 25 | >30.00 | 3 | — |
| 32 | >30.00 | 3 | — |
| 33 | >30.00 | 3 | — |
| 36 | >30.00 | 3 | — |
| 37 | >30.00 | 3 | — |
| 43 | >30.00 | 3 | — |
| 45 | >30.00 | 3 | — |
| 48 | >30.00 | 3 | — |
| 68 | >30.00 | 3 | — |
| Amitriptyline | 3.51 | 3 | 1.10 |

The $IC_{50}$ of the positive control drug Amitriptyline on the hERG current inhibition was consistent with the historical results of the assay party and also consistent with the results reported in the literature, indicating that the results of this assay were credible. The results of the above assay showed that the tested compounds could not achieve the half inhibition to the hERG current at the highest test concentration, so $IC_{50}$ could not be determined, indicating that the compounds of the present disclosure had no obvious inhibitory effect on the hERG channel within the range of test concentrations in this assay. To a certain extent, it could reflect that the compounds of the present disclosure had lower or no cardiotoxicity and showed positive significance for the evaluation of drug safety.

Assay Example 4: Investigation of Antitumor Activity of Drugs In Vivo—Pharmacodynamics of the Compounds of the Present Disclosure in Human Acute Myelocytic Leukemia MV4;11 Cell Subcutaneous Xenograft Tumor Model Cell culture: IMDM culture medium containing 10% fetal bovine serum (FBS), 37° C., 5% $CO_2$.

NOD-SCID mice, female, 6-8 weeks(18-22 g), each mouse was subcutaneously inoculated with 0.1 mL ($1\times10^8$) MV4;11 cells on the right back of each mouse. When the average tumor volume reached 150 $mm^3$, drug administration was started. The dosage and route of administration were shown in the table below. The tumor volume was measured twice a week, and the volume was calculated in cubic millimeters. When the average tumor volume in the vehicle group reached more than 800 $mm^3$, the administration was terminated to compare the difference in the average tumor volume between the compound groups and the vehicle group. The antitumor efficacy of the compounds was evaluated by TGI (%). TGI (%) reflected the tumor growth inhibition rate.

Calculation of *TGI*(%):*TGI*(%)=[1−(average tumor volume at the end of the administration of the compound group−average tumor volume at the beginning of the compound group)/(average tumor volume at the end of the administration of the vehicle group−average tumor volume at the beginning of the vehicle group)]×100%.

The results were shown in Tables 5-8.

TABLE 5

In vivo antitumor assay data

| Group | Animal number | Administration route | Administration dosage | Administration days | TGI (%) |
|---|---|---|---|---|---|
| Vehicle group | 5 | qd, p.o. | — | 9 | — |
| Compound No. 33 of WO2011110612 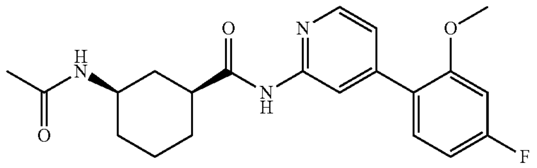 | 5 | q2d, p.o. | 20 mg/Kg | 9 | 51.5 |
| Compound No. 5 of the present disclosure | 5 | q2d, p.o. | 20 mg/Kg | 9 | 98.5 |

TABLE 6

In vivo antitumor assay data

| Group | Animal number | Administration route | Administration dosage | Administration days | TGI(%) |
|---|---|---|---|---|---|
| Vehicle group | 5 | qd, p.o. | — | 9 | — |
| Compound No. 33 of the present disclosure | 5 | qd, p.o. | 5 mg/Kg | 9 | 56.9 |
| Compound No. 67 of the present disclosure | 5 | qd, p.o. | 5 mg/Kg | 9 | 67.8 |

TABLE 7

In vivo antitumor assay data

| Group | Animal number | Administration route | Administration dosage | Administration days | TGI(%) |
|---|---|---|---|---|---|
| Vehicle group | 5 | qd, p.o. | — | 16 | — |
| Compound No. 45 of the present disclosure | 5 | qd, p.o. | 5 mg/Kg | 16 | 62.9 |

TABLE 8

In vivo antitumor assay data

| Group | Animal number | Administration route | Administration dosage | Administration days | TGI(%) |
|---|---|---|---|---|---|
| Vehicle group | 5 | qd, p.o. | — | 7 | — |
| Compound No. 68 of the present disclosure | 5 | qd, p.o. | 5 mg/Kg | 7 | 78.1 |

Assay Conclusion:

The compounds of the present disclosure showed good efficacy in human acute myelocytic leukemia MV4;11 cell subcutaneous xenograft tumor model in vivo, and had a significant antitumor effect.

Assay Example 5: Investigation of Antitumor Activity of Drugs In Vivo—Pharmacodynamics of the Compounds of the Present Disclosure in Human Acute Promyelocytic Leukemia HL-60 Cell Subcutaneous Xenograft Tumor Model Cell culture: IMDM culture medium containing 20% fetal bovine serum (FBS), 37° C., 5% $CO_2$; Nu/Nu mice, female, 6-8 weeks (18-22 g), each mouse was subcutaneously inoculated with 0.1 mL of HL-60 cell suspension (containing about $1\times10^7$ cells) in the axillary region of the right forelimb. When the average tumor volume reached 150 $mm^3$, drug administration was started. The dosage and route of administration were shown in the table below. The tumor volume was measured 2-3 times per week, and the volume was calculated in cubic millimeters. When the average tumor volume in the vehicle group reached more than 800 $mm^3$, the administration was terminated to compare the difference in the average tumor volume between the compound group and the vehicle group. The antitumor efficacy of the compounds was evaluated by TGI (%). TGI (%) reflected the tumor growth inhibition rate.

Calculation of *TGI*(%):*TGI*(%)=[1−(average tumor volume at the end of the administration of the compound group−average tumor volume at the beginning of the compound group)/(average tumor volume at the end of the administration of the vehicle control group−average tumor volume at the beginning of the vehicle control group)]×100%.

The results were shown in Table 9.

TABLE 9

In vivo antitumor assay data

| Group | Animal number | Administration route | Administration dosage | Administration days | TGI(%) |
|---|---|---|---|---|---|
| Vehicle group | 5 | qd, p.o. | — | 9 | — |
| Compound No. 45 of the present disclosure | 5 | qd, p.o. | 5 mg/Kg | 9 | 58.0 |
| Compound No. 67 of the present disclosure | 5 | qd, p.o. | 5 mg/Kg | 9 | 67.8 |
| Compound No. 68 of the present disclosure | 5 | qd, p.o. | 5 mg/Kg | 9 | 90.2 |

Assay Conclusion:

The compounds of the present disclosure showed good efficacy in human acute promyelocytic leukemia HL-60 cell subcutaneous xenograft tumor model in vivo. Nine days after the beginning of the administration, the compounds of the present disclosure showed a significant antitumor effect.

Although the foregoing disclosure has been described in considerable detail by description and examples for the purpose of clear understanding, it will be apparent from the teachings of the disclosure that those skilled in the art, in general, may make certain changes and modifications to the appended claims without departing from the spirit or scope of the appended claims.

The invention claimed is:

1. A compound or a pharmaceutically acceptable salt thereof, or a stereoisomer or isotope thereof, wherein the compound is selected from:

33

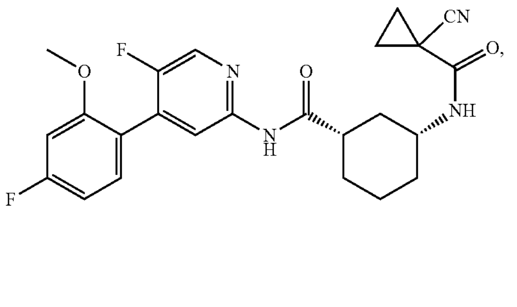

-continued

45

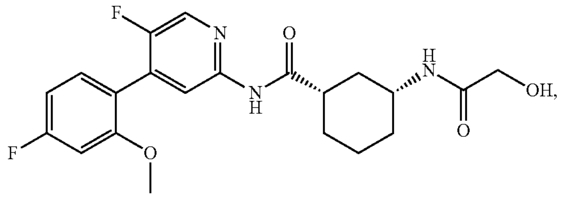

67

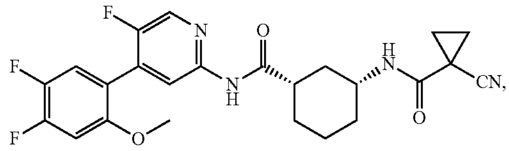

and

68

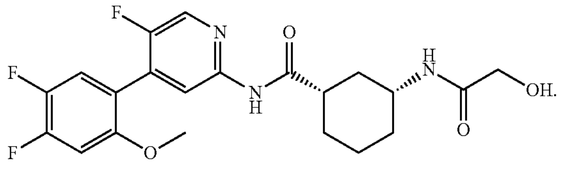

2. A pharmaceutical composition, comprising the compound or a pharmaceutically acceptable salt thereof, or a stereoisomer or isotope derivative thereof according to claim 1.

3. The compound or a pharmaceutically acceptable salt thereof, or a stereoisomer or isotope thereof according to claim 1, wherein the compound is

33

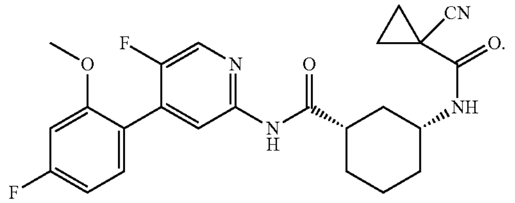

4. The compound or a pharmaceutically acceptable salt thereof, or a stereoisomer or isotope thereof according to claim 1, wherein the compound is

45

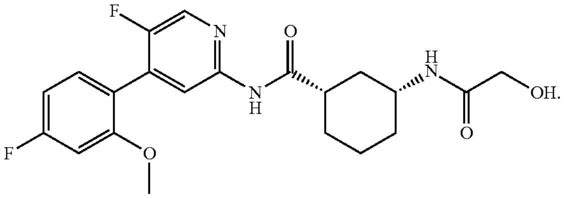

5. The compound of a pharmaceutically acceptable salt thereof, or a stereoisomer or isotope thereof according to claim 1, wherein the compound is

67

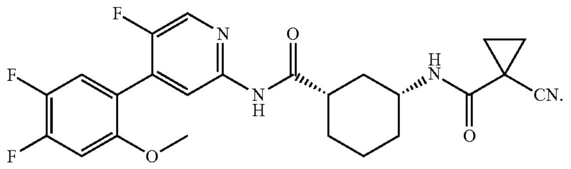

6. The compound or a pharmaceutically acceptable salt thereof, or a stereoisomer or isotope thereof according to claim 1, wherein the compound is

68

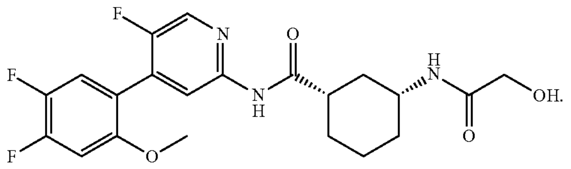

7. A method for treating a hematological tumor in a subject in need thereof comprising, administering to the subject an effective amount of the compound or a pharmaceutically acceptable salt thereof, or a stereoisomer or isotope derivative thereof according to claim 1, wherein the hematological tumor is leukemia.

8. The method according to claim 7, wherein the leukemia is acute myeloid leukemia.

* * * * *